United States Patent
Peterson et al.

(10) Patent No.: US 11,197,627 B2
(45) Date of Patent: Dec. 14, 2021

(54) CONTINUOUS GLUCOSE MONITORING SYSTEM AND METHOD

(71) Applicant: Sanvita Medical, LLC, Billerica, MA (US)

(72) Inventors: Thomas H. Peterson, Wilmington, MA (US); Handani Winarta, Nashua, NH (US); Anthony Florindi, Norfolk, MA (US)

(73) Assignee: SANVITA MEDICAL CORPORATION, Waltham, MA (US)

( * ) Notice: Subject to any disclaimer, the term of this patent is extended or adjusted under 35 U.S.C. 154(b) by 63 days.

(21) Appl. No.: 16/468,047

(22) PCT Filed: Dec. 22, 2016

(86) PCT No.: PCT/US2016/068196
§ 371 (c)(1),
(2) Date: Jun. 10, 2019

(87) PCT Pub. No.: WO2018/118061
PCT Pub. Date: Jun. 28, 2018

(65) Prior Publication Data
US 2020/0015720 A1  Jan. 16, 2020

(51) Int. Cl.
*A61B 5/145* (2006.01)
*A61B 5/1473* (2006.01)
(Continued)

(52) U.S. Cl.
CPC ........ *A61B 5/14532* (2013.01); *A61B 5/1473* (2013.01); *A61B 5/14865* (2013.01); *A61B 5/742* (2013.01)

(58) Field of Classification Search
None
See application file for complete search history.

(56) References Cited

U.S. PATENT DOCUMENTS

| 6,258,229 B1 | 7/2001 | Winarta et al. |
| 2008/0006530 A1* | 1/2008 | Winarta ........... G01N 33/54386 204/403.01 |

(Continued)

FOREIGN PATENT DOCUMENTS

| JP | H07286987 A | 10/1995 |
| WO | 2016-019192 A1 | 2/2016 |
| WO | 2016-036924 A1 | 3/2016 |

OTHER PUBLICATIONS

BR Preliminary Office Action in co-pending application BR 112019012600-7, dated Jul. 21, 2020.

*Primary Examiner* — Thaddeus B Cox
*Assistant Examiner* — Tyra Faith Bookhart
(74) *Attorney, Agent, or Firm* — Robert R. Deleault, Esq.; Hayes Soloway PC

(57) ABSTRACT

A continuous glucose monitoring system and method has an inserter assembly for inserting a sensor through the skin and into subcutaneous tissue where an inserter housing with the sensor remains on the skin after insertion, a sensor housing cover attachable to the sensor housing after insertion where the sensor housing cover has an electronic module and a battery, and an electronic device equipped with wireless communication for communicating with the electronic module of the sensor housing cover assembly, the electronic device configured for receiving input signals from the sensor, converting the input signals to analyte date, displaying the analyte data on a user interface of the electronic device, storing the data for recall, and creating and/or sending reports of the data.

9 Claims, 35 Drawing Sheets

(51) Int. Cl.
  *A61B 5/1486* (2006.01)
  *A61B 5/00* (2006.01)

(56) References Cited

U.S. PATENT DOCUMENTS

2011/0248184 A1* 10/2011 Shah .................... A61B 5/1459
                                                250/458.1
2012/0226122 A1   9/2012 Meuniot et al.

* cited by examiner

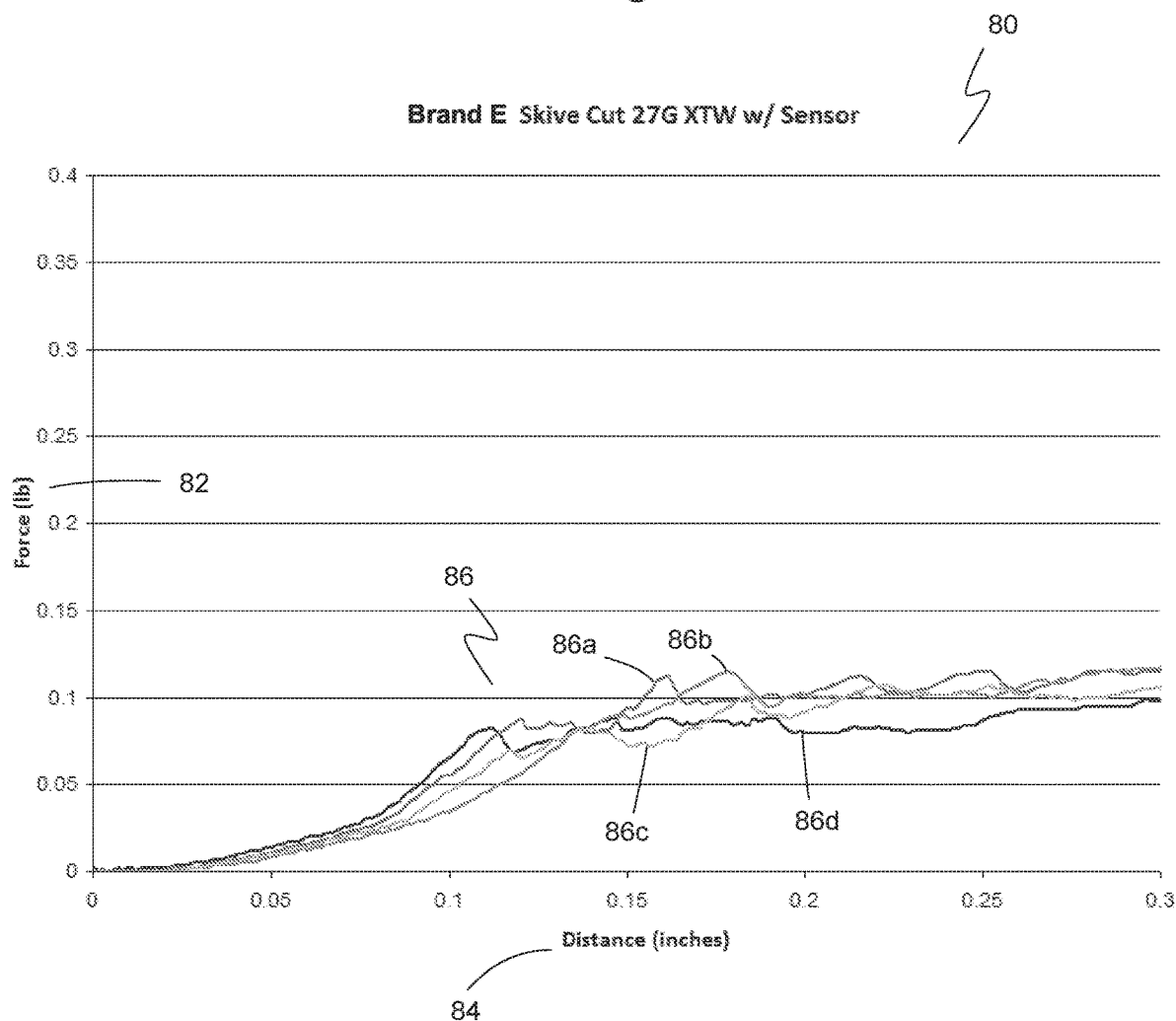

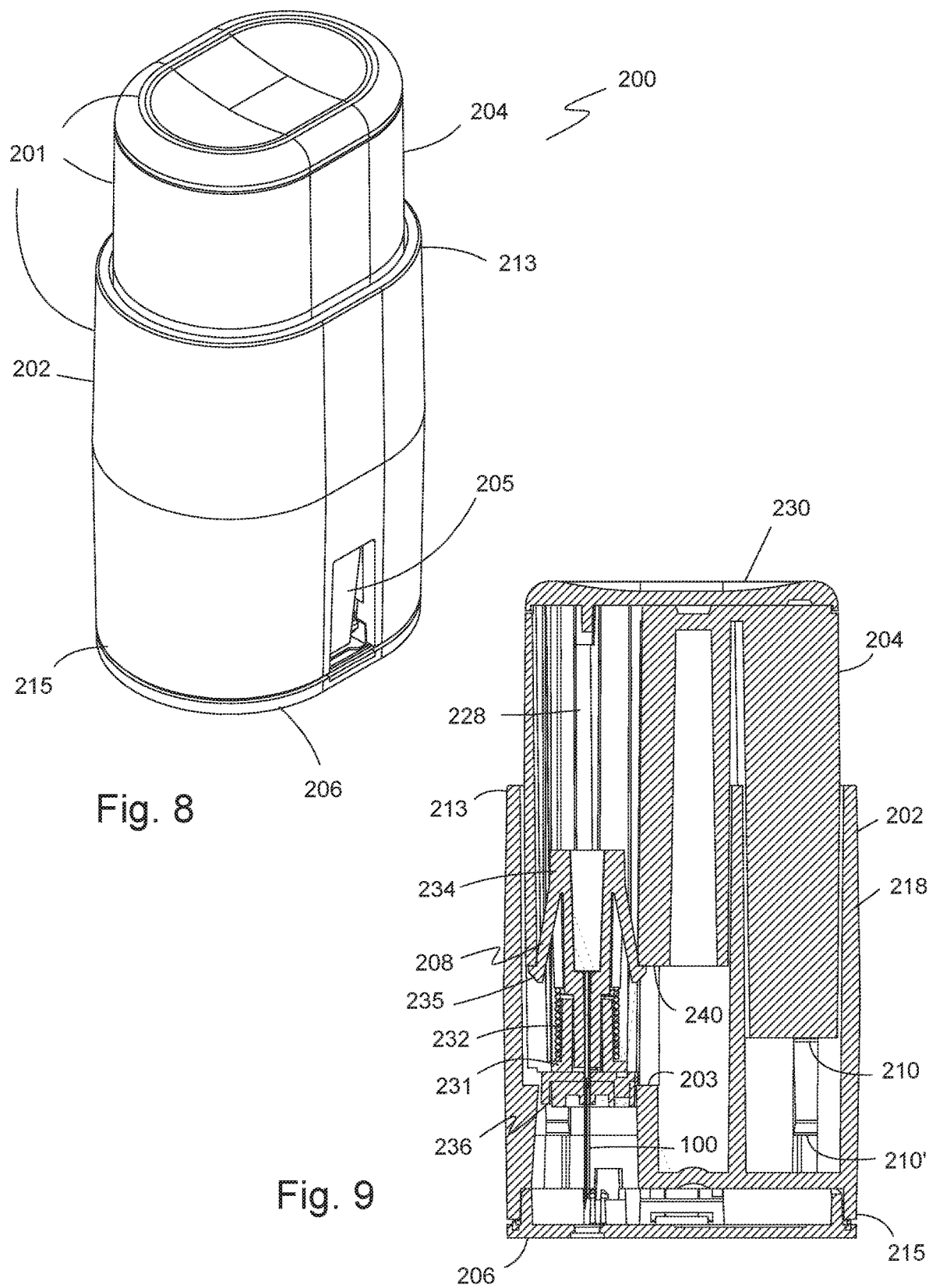

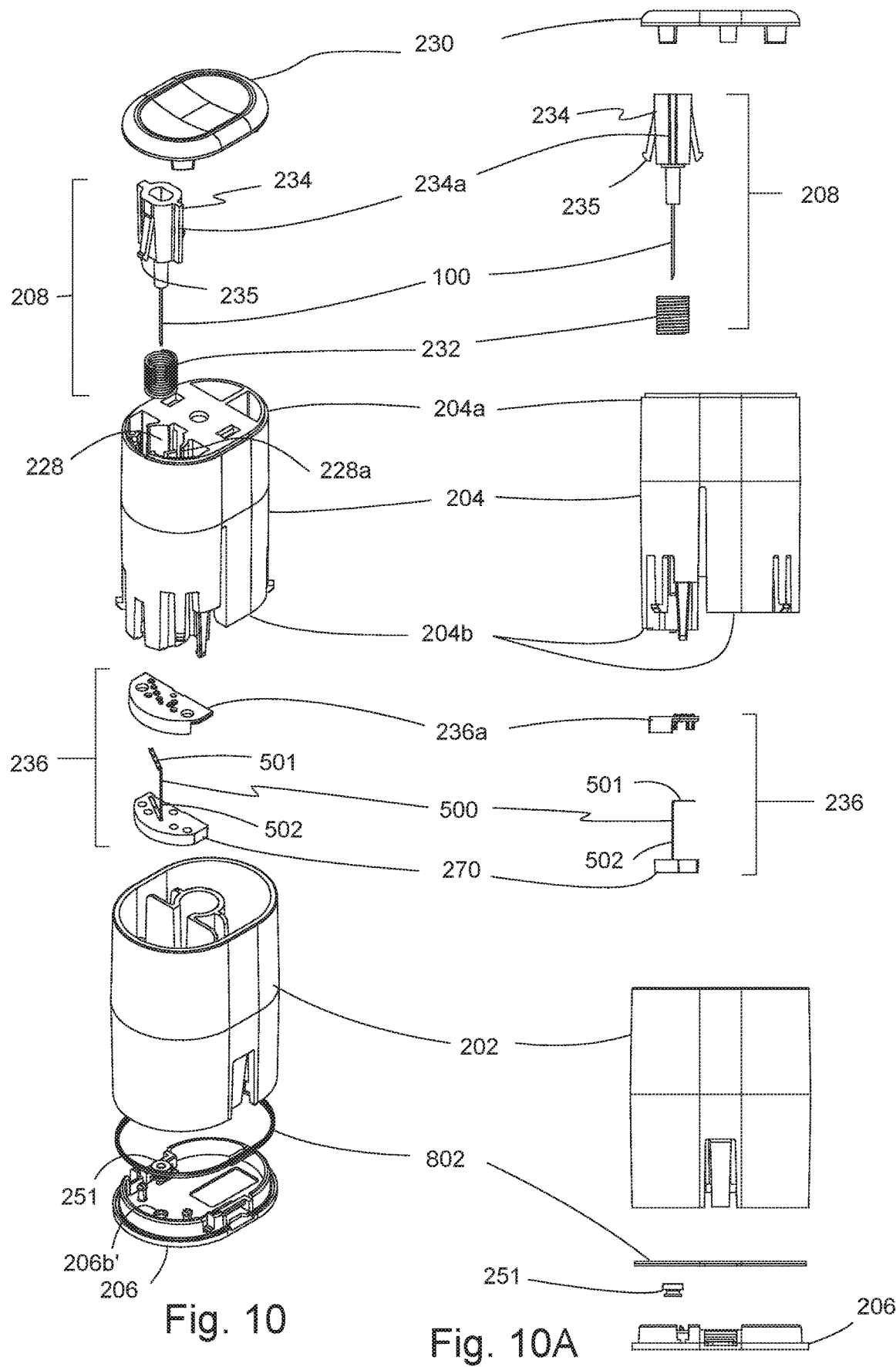

Fig. 11
Fig. 12
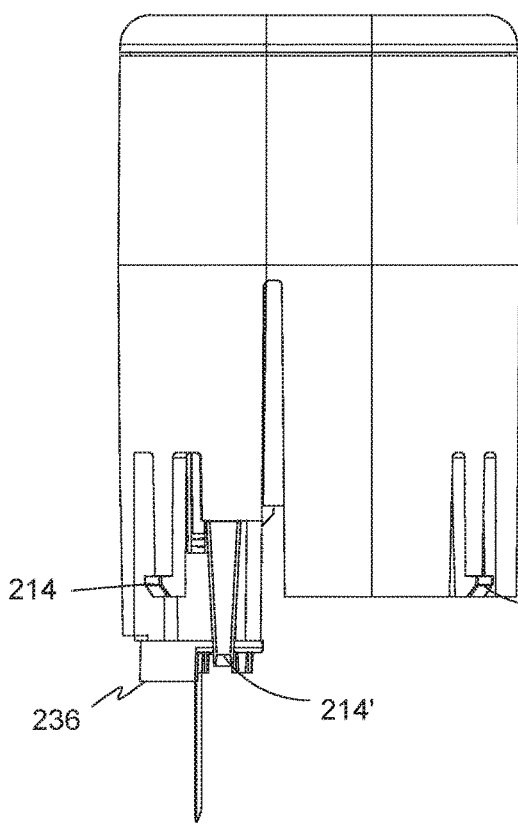
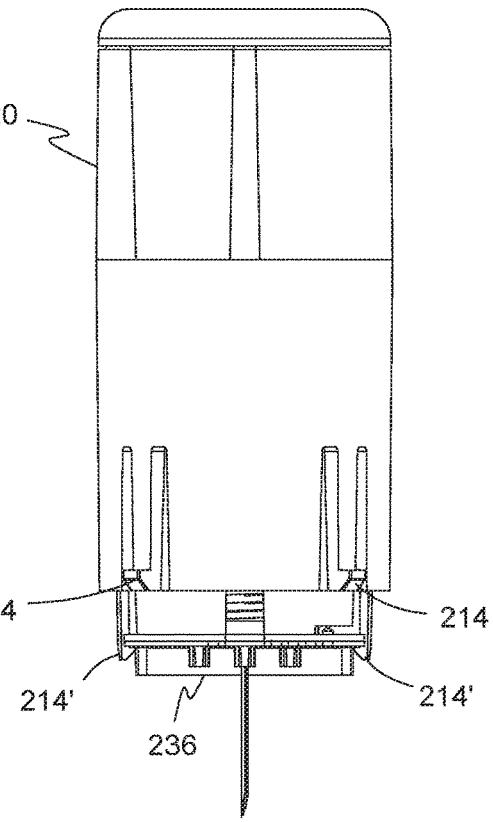
Fig. 13
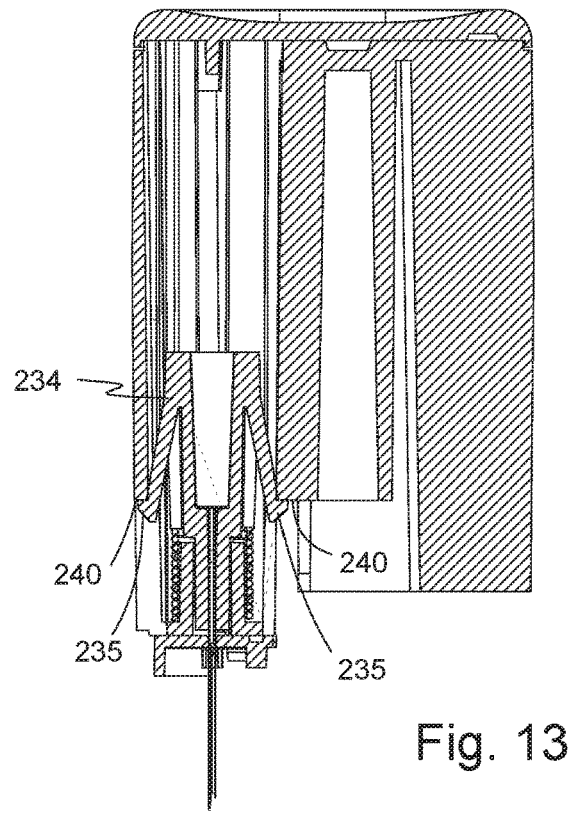
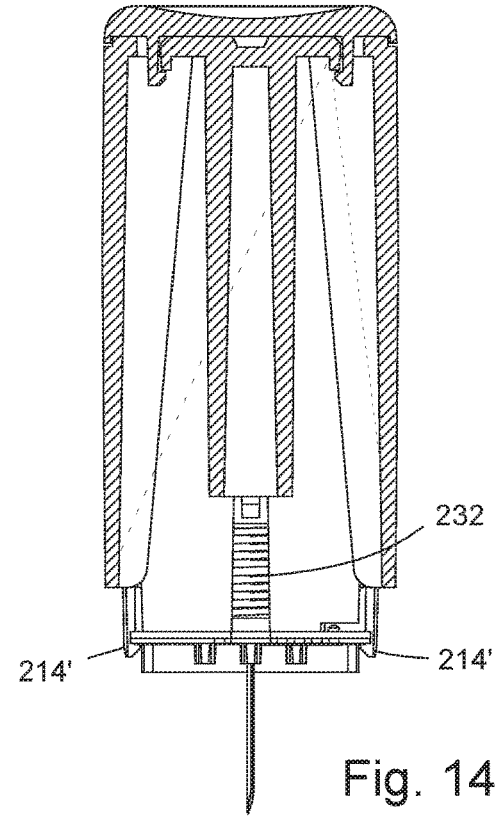
Fig. 14

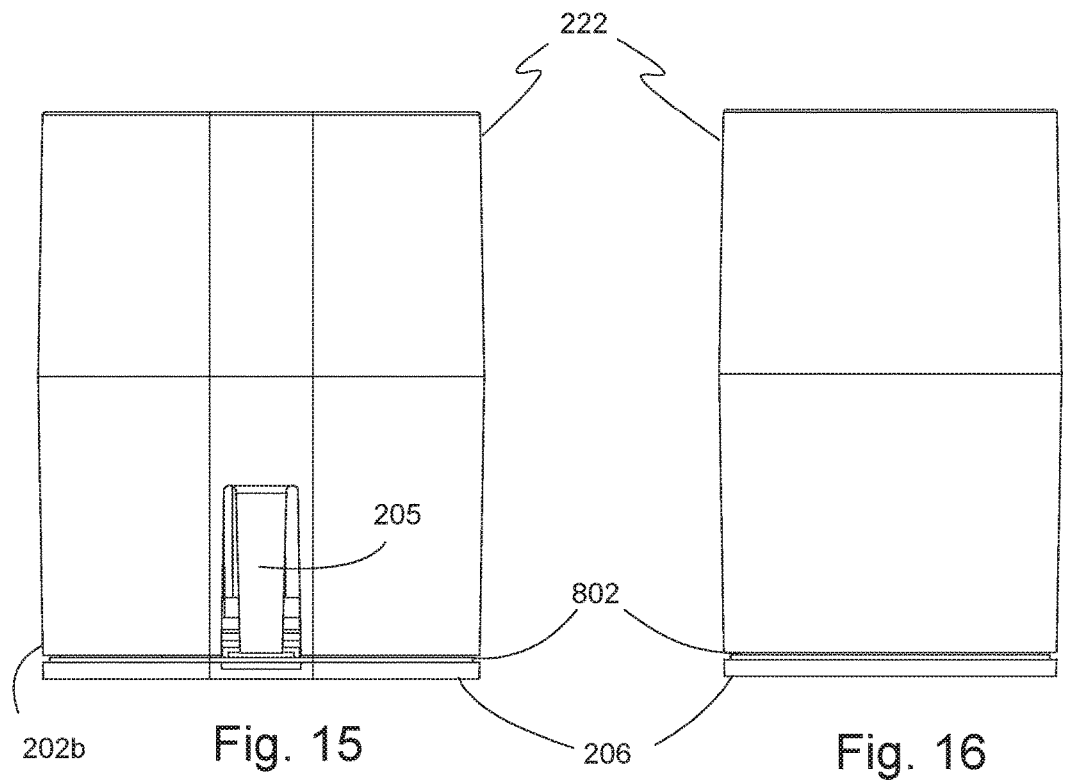
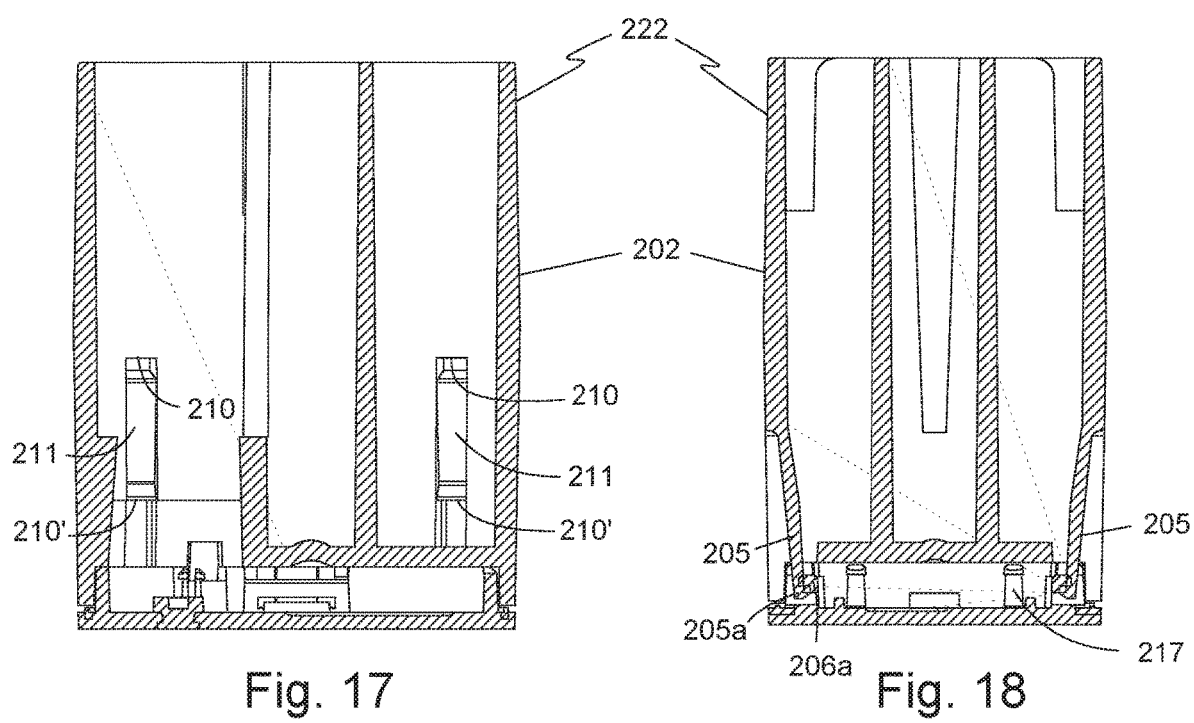

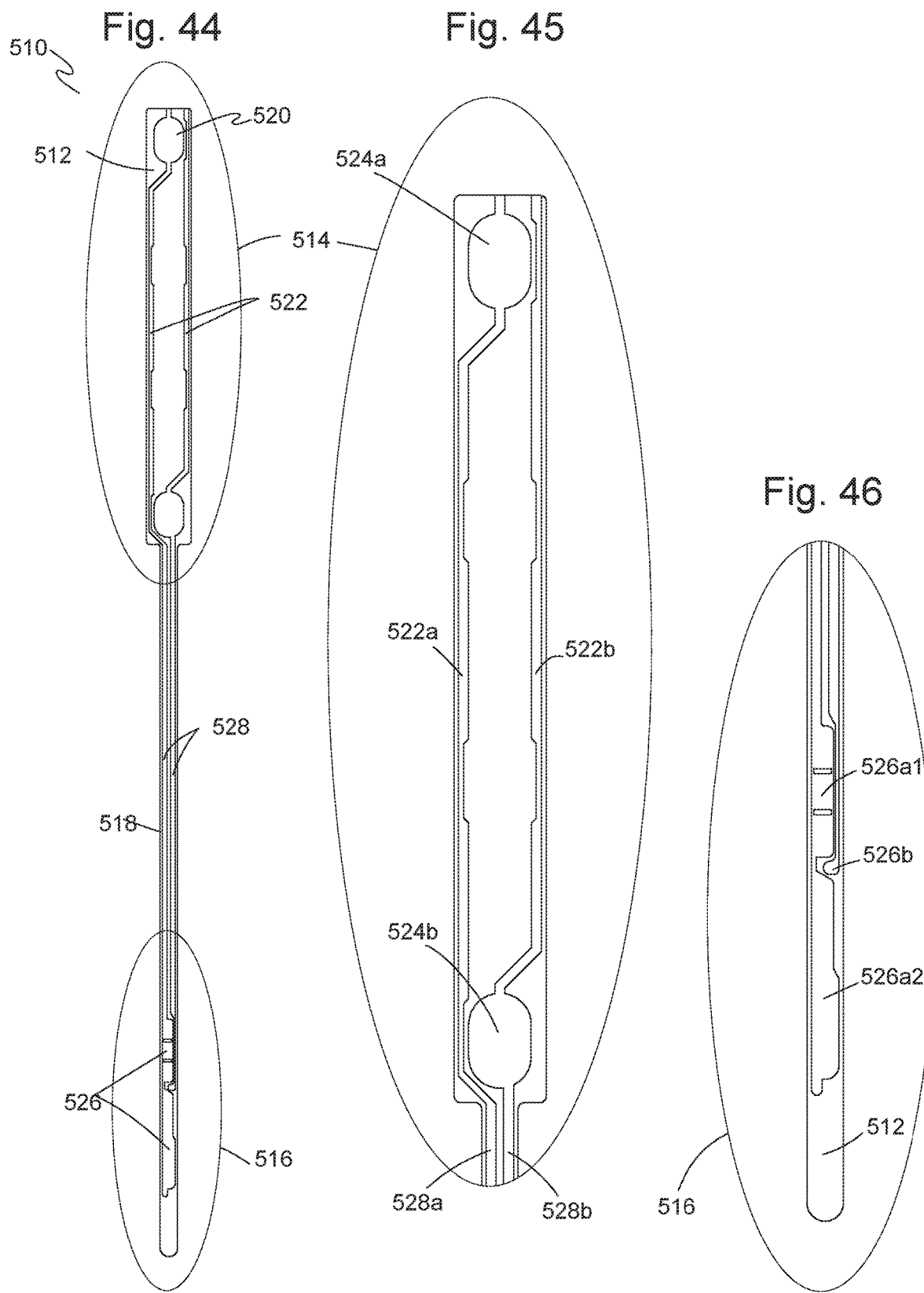

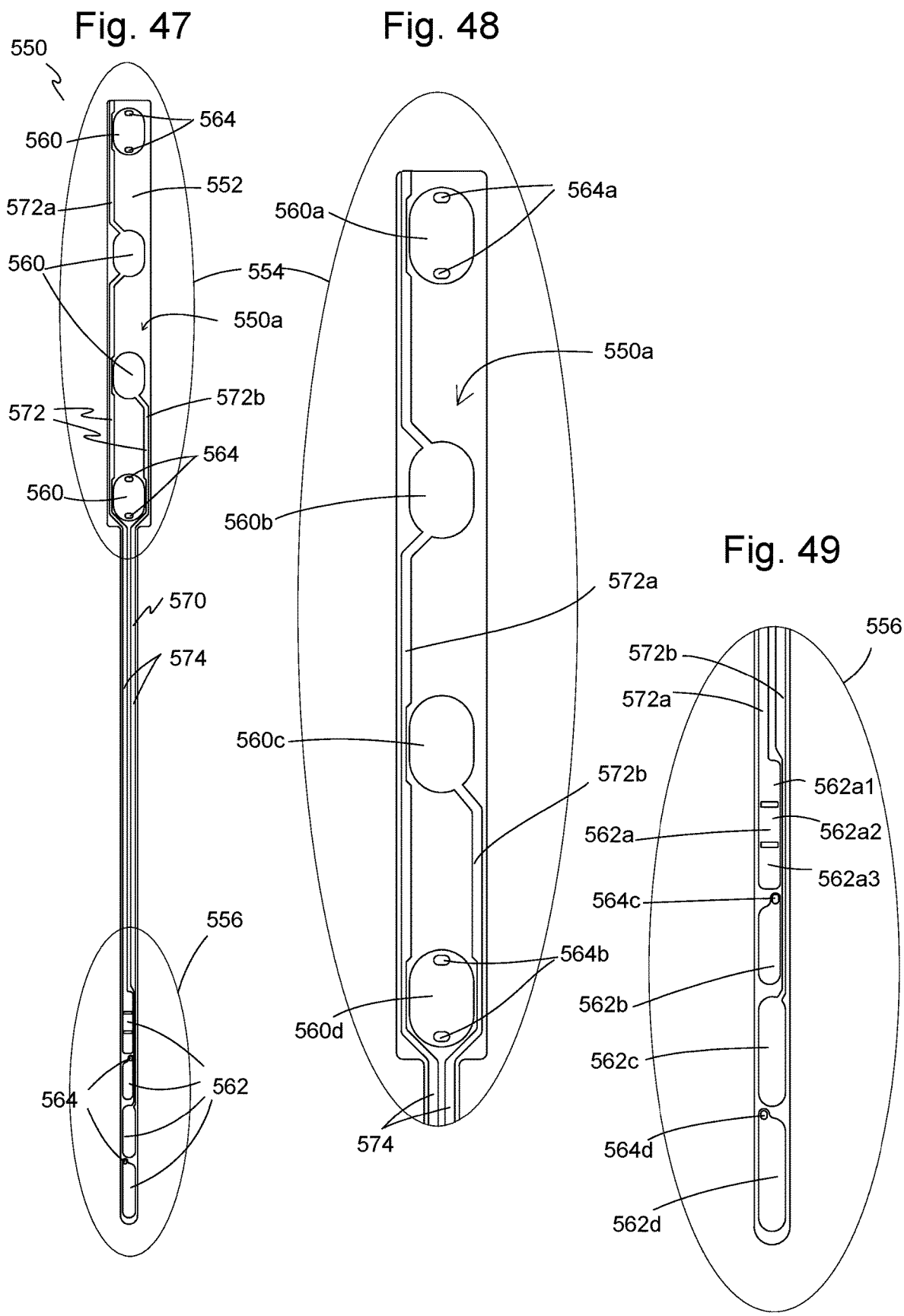

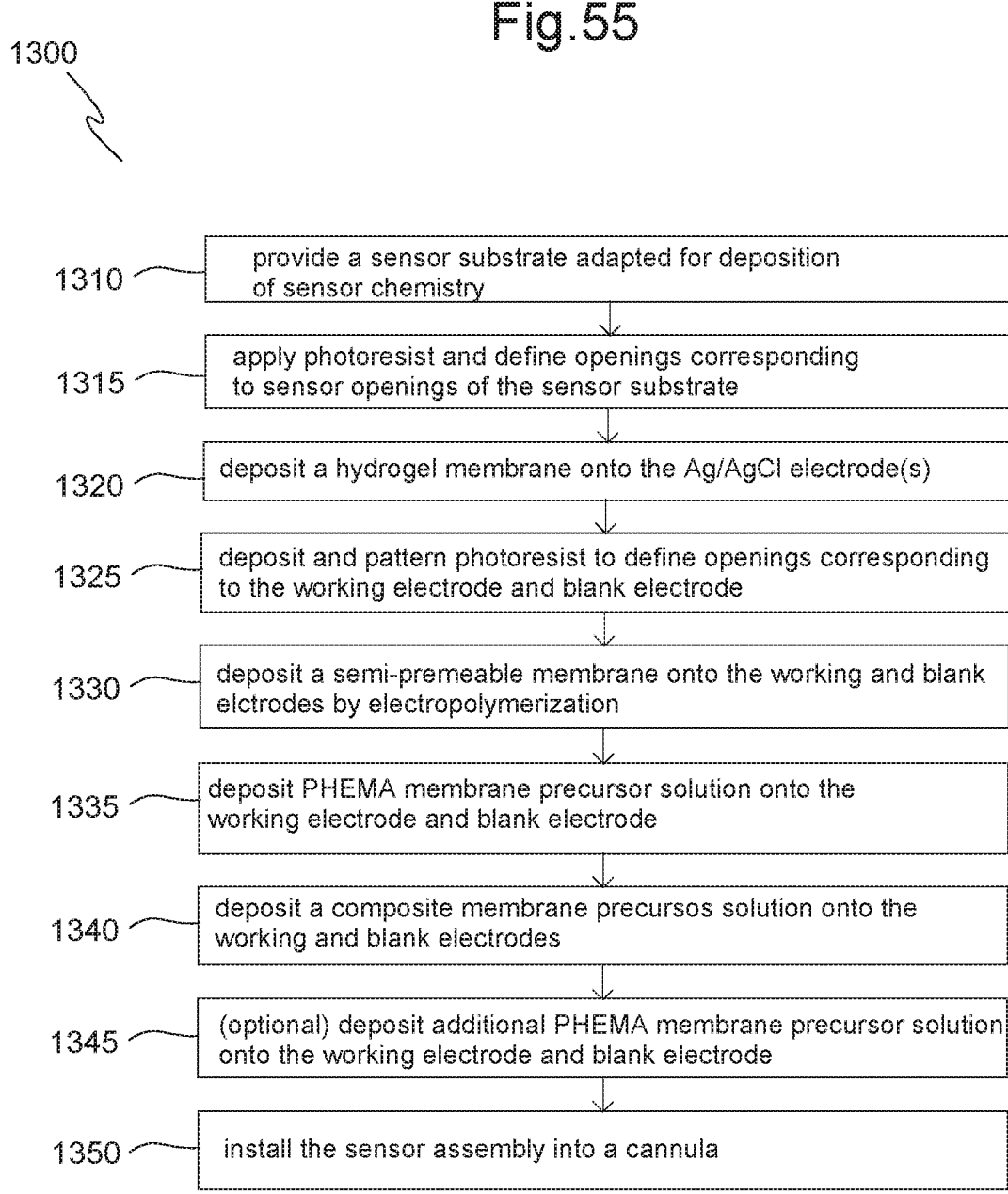

CONTINUOUS GLUCOSE MONITORING SYSTEM AND METHOD

BACKGROUND OF THE INVENTION

1. Field of the Invention

The present invention relates generally to continuous glucose monitoring. More particularly, the present invention relates to a glucose monitoring system having a subcutaneous insertable glucose sensor, an inserter assembly and reader.

2. Description of the Prior Art

Lancets are well-known devices commonly used in the medical field to make small punctures in a patient's skin to obtain samples of blood. They are utilized in hospitals, other medical facilities, and by private individuals such as diabetics for testing droplets of blood for various analytes. Typically, lancets are used only once to reduce the risk of HIV, hepatitis and other blood-borne diseases. The lancet or sharp of these devices is driven into the patient's skin by a small spring that is cocked by a technician or user prior to use. The lancet is covered with a protective, safety cap that keeps the end of the lancet sterile and is removed before use.

A variety of lancet devices are available for use by patients and/or healthcare practitioners. One lancet device is configured for multiple and/or repeated uses. In this variety, the user typically pushes a button or other device on a lancet injector to cause a lancet to penetrate the skin of a patient. More commonly, the lancet device effectively encases and fires the lancet into the patient's skin in order to puncture in an accurate, standardized and consistent manner. The lancet injector may also be provided with an adaptor cap to control and adjust the depth of penetration of the needle of the lancet.

Integrated lancet and sensor devices have been developed that combine the lancet and test strip or sensor into a single package. These integrated devices are typically used with a lancet injector where the integrated lancet and test strip is removed from the lancet injector and connected to a meter after acquisition by the test strip of the blood sample produced by the lancet, or used with a meter with built-in lancet injector.

More recently, continuous glucose monitoring devices have been developed for implanting into a patient's skin. Continuous monitoring systems typically use a tiny implantable sensor that is inserted under the skin, or into the subcutaneous fat layer to check analyte levels in the tissue fluid. A transmitter sends information about the analyte levels by way of, for example, a wire to a monitor or wirelessly by radio waves from the sensor to a wireless monitor. These devices are typically implanted for three to seven days of use to monitor in real-time a patient's glucose level.

One such device is disclosed in U.S. Pat. No. 5,299,571 to John Mastrototaro. The device is an apparatus for implantation of in-vivo sensors. The apparatus includes a housing, a dual-lumen tube extending therefrom, and an in-vivo sensor received within one of the lumens of the tube. A needle is received within the other lumen of the tube, and is used to insert the tube through the skin. After implantation, the needle is removed, and the flexible tube and sensor remain beneath the skin.

U.S. Patent Application Publication 2010/0022863 (2010, Mogensen et al.) discloses an inserter for a transcutaneous sensor. The inserter includes a needle unit and a sensor housing. The needle unit includes a needle hub and a carrier body. The sensor housing and the needle hub are releasably connected and when they are connected, the insertion needle is placed along the sensor (e.g. surrounding the sensor wholly or partly). The carrier body guides the movement relative to the housing between a retracted and an advanced position. When released, the needle unit and the sensor housing are forced by a spring unit to an advanced position where the needle and sensor are placed subcutaneously. Upwardly-bent parts on the leg of the housing set the insertion angle of about 30° into the skin of the patient.

U.S. Patent Application Publication 2012/0226122 (2012, Meuniot et al.) discloses an inserter device for an analyte sensor. The device includes a housing that is positioned above the subcutaneous fat layer, a blade shuttle, and a sensor shuttle. A spring is compressed between the blade shuttle and the sensor shuttle. The blade shuttle and sensor shuttle move towards the subcutaneous fat layer. When a spring force is released by the spring, the blade shuttle moves towards and pierces into the subcutaneous fat layer creating a pathway into the subcutaneous fat layer. The analyte sensor is implanted by the sensor shuttle by following the blade shuttle into the pathway created by the blade shuttle. The blade shuttle is then retracted from the subcutaneous fat layer, leaving the analyte sensor in the fat layer.

U.S. Patent Application Publication 2013/0256289 (2013, Hardvary et al.) discloses a diagnostic device. The diagnostic device has partially retractable hollow guide needles for the intradermal placement of diagnostic elements fixedly connected to measuring means within this device. This obviates the need to remove the guide needle and to connect the diagnostic elements to the measuring means after placement into the skin.

SUMMARY OF THE INVENTION

Continuous glucose monitoring (CGM) devices have been slow to be adopted by many patients due to the pain and long term discomfort of initial deployment and long term use (3 to 7 days). Currently available devices are commonly compared and criticized on CGM user forums for their pain of deployment.

Pain of deployment can be shown to be directly related to the design of the device. Axons that pass through the subcutaneous layer and end in the epidermis are called nociceptors. These specialized neurons transmit pain messages. The density of these pain receptors ranges between 2 and 2500 neurites/mm$^2$ just below the skin surface, and varies greatly depending on location. The probability and magnitude of a pain response during any incision is proportional to the number of affected nociceptors and the trauma inflicted upon these nociceptors. With nociceptors located throughout the thickness of the epidermis, a deeper incision is more likely to trigger a pain response due to the increased likelihood of trauma to more nociceptors.

When inserted into subcutaneous tissue, the combined cross sectional area of a sensor and introducer is proportional to the force of insertion and also to the probability and magnitude of triggering pain response. FIG. 1 is a graph 10 showing the maximum peak force 12 of insertion (lbs.) of various commercial inserter sets plotted against the measured cross section area 14 of the inserter set (in$^2 \times 10^{-3}$). As can be seen by a linear regression of the data points in FIG. 1, the peak force increases linearly with cross sectional area with a regression line 16 represented by equations 1 and 1a, which have an R$^2$ value of 0.932. Data in graph 10 is for needles inserted at 90 degrees to the skin surface regardless of the intended insertion angle of the particular needle.

$$\text{peak force (lb}_f) = (0.3998)(\text{cross sectional area (in}^2)) + 0.0556 \text{ lb}_f \quad (1)$$

$$\text{peak force (N)} = (0.0223)(\text{cross-sectional area (m}^2)) + 1.100 \text{ N} \quad (1a)$$

Among the tested needles for graph 10 in FIG. 1 and graph 20 in FIG. 2, Brand A is a 22 gauge split needle with a lumen, Brand B is a 22-24 gauge needle with a bi-lumen, Brand C is a 23-24 gauge split needle with a single lumen, and Brand D is a 26 gauge needle. A split needle means that about a third of the needle is removed for a distance creating a skive cut in the needle. The Brand A needle with lumen has the highest peak force. The Brand C needle has a peak force that is slightly less than the larger 22 gauge Brand A split needle. The Brand D needle is a needle intended for insertion at 45 degrees to the skin surface. It is notable that the peak force increases by 11% when inserting a needle at 45 degrees compared to 90 degrees to the skin surface. Thus, when used as intended, the peak force for Brand D needle would be 11% greater than as shown in FIG. 1.

It is important to note that the sensor of the present invention was installed in various needle sizes and tested for peak insertion force. As can be seen from the graph, the sensor of the present invention in a 23-gauge split needle has a lower peak insertion force than the comparable Brand C needle. Also, the sensor of the present invention in a 24-gauge split needle had a lower peak insertion force than the Brand D 26-gauge needle notwithstanding having a larger cross-sectional area than the Brand D needle. The needle with the lowest peak force (FIG. 1) and lowest work (FIG. 2) is the sensor of the present invention in a 27 gauge XTW Skive Cut needle with an oval cross-sectional shape.

The cross-sectional area of an inserter set (i.e. needle and sensor) also strongly correlates with the relative intensity of pain of insertion as reported by users of these devices. The Brand D device is considered by users as being much more comfortable than the earlier Brand A system. The present invention the same or a larger needle gauge has a better (lower) peak insertion force of a comparable brand needle as seen from FIGS. 1 and 2.

FIG. 2 is a graph 20 showing work 22 (lb-in) plotted against the combined cross sectional area 24 (in$^2 \times 10^{-3}$) of the sensor and introducer of various commercial introducer sets. For insertion of a sensor and introducer in combination, the length or depth of insertion into subcutaneous tissue is proportional to the work energy (force times distance) and proportional to the probability and magnitude of triggering pain response from the user. As can be seen by a linear regression of the data points of FIG. 2, the work increases linearly with cross sectional area with a regression line 26 represented by equations 2 and 2a, which have an $R^2$ value of 0.9715.

$$\text{Work (lb-in)} = (0.0439)(\text{cross sectional area (in}^2)) + 0.0133 \quad (2)$$

$$\text{Work (N-m)} = (6.23\text{E-}5)(\text{cross-sectional area (m}^2)) + 1.50\text{E-}3\text{N-m} \quad (2a)$$

FIG. 3 is a graph 30 with typical force of insertion 32 (lbs.) plotted against insertion distance 34 (in) to demonstrate the concept of work energy. FIG. 3 is a plot of data obtained from three separate insertion force measurements for a Brand R inserter with a Brand R sensor. As the sharp penetrates tissue, the force is dynamically recorded. The integral of a curve 36 (i.e., the area 28 under one of curves 36a-36c) is the work energy (lb-in). Work energy (force times distance) is proportional to the incidence of triggering a pain response by users of the inserter. In simple terms, small, shallow incisions hurt less for the reasons stated above. Therefore, an inserter that reduces or minimizes insertion pain is more likely to be adopted by patients.

Reducing or minimizing insertion pain is one criterion for patient acceptance of any continuous monitoring system. Other criteria include the convenience and ease-of-use of the inserter device. Therefore, a need exists for an inserter set and an inserter assembly that reduces or minimizes the patient's pain and inconvenience of inserting a continuous monitoring sensor. The present invention achieves these and other objectives by providing a continuous analyte monitoring inserter apparatus for subcutaneous placement of a sensor into a patient and a sharp/needle that minimizes insertion pain with a reduced cross-sectional area.

In one embodiment of the present invention, a sharp useful for continuous glucose monitoring has an elongated tubular body with a pointed tip. The elongated tubular body has a generally oval or elliptical cross-sectional shape and defines a conduit therethrough. A sharp open region extends a predefined distance from the pointed tip along the elongated tubular body and has a portion of the generally oval tubular body removed, thereby defining an unenclosed concave well within the remaining elongated tubular body. In another embodiment, the sharp includes a continuous monitoring sensor retained in the concave well, where the top surface of the continuous monitoring sensor resides completely within the concave well formed by the wall of the tubular body.

Another aspect of the present invention is an inserter assembly. In one embodiment, the inserter assembly is a single action inserter assembly that, using a single action, substantially simultaneously performs the steps of (1) implanting the sensor subcutaneously into the patient, (2) fixedly seating a sensor deployment assembly that includes the sensor within a sensor housing attached to the patient, (3) retracting a needle used to implant the sensor, and (4) releasing the inserter assembly from the sensor housing. In one embodiment, the action of retracting the needle is performed by retracting the needle into the inserter assembly. In another embodiment, the inserter assembly further includes implanting a lumen along with the sensor subcutaneously in the patient.

In another embodiment, the inserter assembly includes a deployment button containing a needle deployment mechanism. The needle deployment mechanism has a needle carrier incorporating a sharp and a needle carrier catch that temporarily prevents the needle carrier from moving. The deployment button is movably received in a inserter housing, where the inserter housing has a sensor deployment assembly that connects in mating agreement to the sharp. The sharp extends beyond the sensor deployment assembly into the sensor housing and contains the sensor, which is not fixedly attached to the sharp. A sensor housing is releasably received within the inserter housing.

In another embodiment, the inserter assembly includes an inserter housing having a first housing end and a second housing end. A deployment button is at least partially disposed in and slidable within the inserter housing through the first housing end, where the deployment button is movable between a first position and a second position. The second position may be a locked position. A deployment mechanism slidably disposed within the deployment button is movable between a ready position, an insertion position, and a retracted position. The deployment mechanism has a needle.

A sensor deployment assembly is disposed within the inserter housing and removably mated with the deployment mechanism and the deployment button. The sensor deployment assembly has a needle bore in which the needle is disposed when the deployment mechanism is in the ready position. A sensor is partially disposed within the needle or the needle bore, where the deployment mechanism, the needle, and the sensor define a deployment axis. The sensor has an electrode system and an electrical contact portion. In one embodiment, the electrical contact portion is parallel to but spaced from the deployment axis. In another embodiment, the electrical contact portion extends transversely away from the deployment axis. In one embodiment, for example, the electrical contact portion extends substantially perpendicularly from the deployment axis.

The inserter assembly also includes a sensor housing disposed at and removably retained by the second housing end of the inserter housing. The sensor housing has a bottom surface that defines a sensor opening therethrough and aligned with the deployment axis.

Movement of the deployment button from the first position to the second position causes the sensor to be implanted subcutaneously into the patient along the deployment axis, the needle of the deployment mechanism to retract to the retracted position, the sensor deployment assembly to be fixed within the sensor housing, and inserter assembly to release from the sensor housing. In one embodiment, the inserter assembly includes the inserter housing, the deployment button and the deployment mechanism.

In some embodiments, the movement of the deployment button from the first position to the second position is a single movement causing substantially at the same time the sensor to be implanted subcutaneously into the patient along the deployment axis, the needle of the deployment mechanism to retract to the retracted position, the sensor deployment assembly to be fixed within the sensor housing, and the inserter housing, the deployment button and the deployment mechanism to release from the sensor housing.

In one embodiment, the single activation has an auditory indication that the sensor is implanted in the patient and the inserter assembly is released from the sensor housing. In another embodiment, the single activation has a sensory indication through the inserter assembly that the sensor is implanted in the patient and the inserter assembly is released from the sensor housing.

In another embodiment, the inserter housing has a housing recess for receiving and retaining a button catch when the deployment button is in the second position.

In another embodiment, the inserter housing has a body catch retaining the sensor housing partially within the inserter housing. The body catch is released from the sensor housing by the deployment button when the deployment button is moved into the second position.

In another embodiment, the sensor deployment assembly includes a sensor deployment body, a sensor deployment guide, and a sensor carrier. The sensor deployment body has a sensor deployment locking mechanism configured to engage the sensor housing when the button is moved to the second locked position, thereby locking the sensor deployment assembly with the sensor housing. In one embodiment, the sensor deployment locking mechanism is one or more resilient deployment catches on the sensor deployment assembly biased to engage a deployment catch surface on the sensor housing. Similarly, the deployment locking mechanism may be one or more resilient deployment catches on the sensor housing that are biased to engage respective deployment catch surfaces on the sensor deployment assembly.

The sensor deployment guide is attached to the sensor deployment body and positioned to stop travel of the deployment assembly when the deployment button is moved to the second locked position. For example, the deployment guide contacts the sensor housing to stop travel of the deployment assembly. The sensor carrier is attached to the sensor deployment guide, secures the sensor, and has a board-receiving face.

In some embodiments, the sensor deployment assembly further includes a plurality of electronic coupling pads electrically coupled to the electrical contact portion of the sensor. The electronic coupling pads are positioned to be electrically coupled to measuring electronics.

In some embodiments, the sensor deployment assembly defines a sensor groove along the top sensor carrier surface, where the sensor extends through the sensor groove on its way to the electronic coupling pads attached to an upper deployment body.

In some embodiments, the deployment axis is substantially perpendicular to the bottom surface of the sensor housing, where the bottom surface of the sensor housing is configured to contact the patient during implantation of the sensor.

In yet other embodiments, the inserter assembly includes an electrical component housing that is releasably attachable to the sensor housing and configured to receive and transmit electrical signals generated by the electrode system on the sensor.

In other embodiments, the inserter assembly includes a cover assembly that is releasably attachable to a top of the sensor deployment assembly. The cover assembly has a sensor housing engagement mechanism configured to engage the sensor housing to lock the cover assembly to the sensor housing. A sealing member on a bottom surface of the cover assembly aligns with and forms a seal between the delivery bore and the needle bore. A sensor board with electronic coupling pads is electrically coupled to the electrical contact portion of the sensor, where the sensor mates with the electronic coupling pads positioned for being electrically coupled to measuring electronics. The cover assembly also includes an electrical component configured to receive and transmit electrical signals generated by the electrode system on the sensor. The electrical component has electrical contacts coupled to the electronic coupling pads on the sensor deployment assembly.

In other embodiments, the inserter assembly includes a resilient button catch on the inserter housing or the sensor housing, where the button catch is biased to engage a button catch surface on the other of the inserter housing or the sensor housing when the deployment button is in the second position. The inserter assembly may also include a resilient needle-carrier catch on the deployment button or the needle carrier, where the needle-carrier catch is biased to disengage a second catch surface on the other of the deployment button or the needle carrier when the deployment button is moved to the second position. The inserter assembly may also include a resilient housing catch on the inserter housing or the sensor housing, where the housing catch is biased to disengage a housing catch surface on the other of the inserter housing or the sensor housing when the button in moved to the second position.

Another embodiment of the inserter assembly has an inserter housing with a housing circumferential wall defining a wall inside surface, a first housing end and a second housing end. The housing circumferential wall has at least one of either a cam surface extending longitudinally along a portion of the wall inside surface from a first point spaced from the first housing end to a second point spaced from the second housing end or a cam rider adapted for sliding along a cam surface. When the housing circumferential wall has the cam surface, the cam surface causes a wall thickness of the housing circumferential wall along the at least one cam surface to become thinner from the first point to the second point.

The inserter assembly also has a deployment button with a button circumferential wall defining a wall outside surface, a first button end and a second button end. The button circumferential wall has at least one of either a resilient cam rider adapted for sliding along the at least one cam surface of the housing circumferential wall when the inserter housing has the at least one cam surface, or a cam surface extending longitudinally along a portion of a button outside wall surface when the inserter housing has a cam rider. The deployment button is at least partially disposed in and slidable within the inserter housing through the first housing end, where the second button end is inside the inserter housing and the first button end is outside the inserter housing. The deployment button is movable only between a first position, where a larger portion of the button circumferential wall is outside of the inserter housing, and a second position, where a smaller portion of the button circumferential wall is outside of the inserter housing.

The inserter assembly also has a needle assembly that includes an assembly body with a needle body end and a hollow needle with a longitudinal slot through a needle circumferential wall. The hollow needle is fixedly attached to the needle body end. The needle assembly is slidably disposed within the deployment button and movable only between a ready position and a retracted position. When the needle assembly is in the ready position, the hollow needle extends out of the second button end of the deployment button.

The inserter assembly also has a sensor deployment assembly detachably mated with the deployment button at the second button end. The sensor deployment assembly has a needle bore through which the hollow needle extends when the needle assembly is in the ready position. The sensor deployment assembly also has a sensor with an electrode end portion and a sensor electrical contact portion. The sensor is partially disposed within the needle bore and within the hollow needle, where the sensor is adapted to provide a lateral force against the needle circumferential wall when the needle assembly is in the ready position and during insertion of the sensor subcutaneously. The sensor electrical contact portion extends laterally away from the needle bore and the hollow needle.

The inserter assembly also has a sensor housing disposed at and removably retained by the second housing end of the inserter assembly. The sensor housing has a bottom surface and defines a sensor opening therethrough that is aligned with the hollow needle for receiving the hollow needle therethrough.

Movement of the deployment button from the first position to the second position causes, in a substantially simultaneous action, the sensor to be implanted subcutaneously into the patient, the needle assembly to retract to the retracted position, the sensor deployment assembly to be fixed within the sensor housing, and the inserter housing to release from the sensor housing.

In another embodiment of the inserter assembly, the sensor deployment assembly includes a lower deployment body and an upper deployment body. For example, the lower deployment body has a top surface, a bottom surface, a circumferential surface, a bore forming a portion of the needle bore, and a slot formed into the top surface of the lower deployment body and in communication with the bore, where the slot contains the sensor electrical contact portion of the sensor. The upper deployment body has a top surface, a bottom surface, a bore forming a portion of the needle bore, a plurality of resilient electrical contact members extending above the top surface and below the bottom surface, and a skirt extending downward from the bottom surface along a circumferential portion of the upper deployment body. The skirt extends to at least the bottom surface of the lower deployment body and is positioned to abut the sensor housing to stop travel of the sensor deployment assembly when the deployment button is moved to the second position. The upper deployment body is fixedly attached to the lower deployment body, thereby capturing the sensor electrical contact portion in the slot of the lower deployment body and causing the plurality of resilient electrical contact members to electrically couple to a plurality of electrical contact pads on the sensor electrical contact portion. The sensor deployment assembly has a sensor deployment locking mechanism configured to engage the sensor housing when the button is moved to the second position, thereby locking the sensor deployment assembly within the sensor housing.

In another embodiment of the inserter assembly, the bottom surface of the sensor housing is configured to adhere to the patient during implantation of the sensor. In one embodiment, for example, the sensor deployment locking mechanism includes one or more bores with a resilient deployment catch extending upward from an inside bottom surface of the sensor housing, where the resilient deployment catch is biased to engage a deployment catch surface of the one or more bores in the sensor deployment assembly.

In another embodiment of the inserter assembly, the sensor, when implanted subcutaneously in the patient, has a working electrode of an electrode system on the sensor extending into the patient by about 4 mm to about 7 mm. In another embodiment, the sensor, when implanted subcutaneously in the patient, has a working electrode of an electrode system on the sensor extending into the patient by about 2 mm to about 10 mm.

In another embodiment, the inserter assembly also includes a resilient button catch on one of the inserter housing or the sensor housing, where the button catch is biased to engage a button catch surface on the other of the inserter housing or the sensor housing when the deployment button is in the first position. The deployment button or the needle carrier has a resilient needle assembly catch biased to disengage a second catch surface on the other of the deployment button or the needle assembly when the deployment button is moved to the second position. One of the inserter housing or the sensor housing has a resilient housing catch biased to disengage a housing catch surface on the other of the inserter housing or the sensor housing when the deployment button is moved to the second position.

In some embodiments of the sensor inserter assembly, the movement of the deployment button from the first position to the second position is a single movement causing substantially at the same time the sensor to be implanted subcutaneously into the patient, the needle assembly to retract to the retracted position, the sensor deployment assembly to be fixed within the sensor housing, and the inserter housing to release from the sensor housing.

Another aspect of the present invention is directed to a multi-layer, thin-film substrate assembly for use in forming a subcutaneous analyte sensor. In one embodiment, the substrate assembly has a base layer made of an electrically-insulating material, where the base layer has a base layer substrate with a base layer proximal end portion, a base layer distal end portion, and a base layer middle portion extending longitudinally between the base layer proximal end portion and the base layer distal end portion.

A first metallized layer is disposed on the base layer substrate and defines at least one circuit extending longitudinally along the base layer substrate. Each circuit has an electrically-conductive contact pad formed at each of the base layer proximal end portion and the base layer distal end portion with an electrically-conductive trace electrically coupling the electrically-conductive contact pad at the base layer proximal end portion with the electrically-conductive pad at the base layer distal end portion.

A middle layer is disposed over the base layer, where the middle layer has a middle layer substrate made of an electrically-insulating material with a second proximal end portion, a second distal end portion, and a second middle portion. The middle layer is aligned with the base layer and has a plurality of middle layer through openings with side walls. Each of the middle layer through openings is in communication with a respective one of the electrically-conductive contact pad of the circuit(s) of the base layer.

A second metallized layer is disposed on the middle layer and the side walls of the through openings. The second metallized layer defines at least two circuits, where each of the circuits of the second metallized layer has an electrically-conductive contact pad formed at the second proximal end portion and at the second distal end portion with an electrically-conductive trace electrically coupling the electrically-conductive contact pad at the middle layer second proximal end portion with the electrically-conductive pad at the middle layer distal end portion. One of the circuits is electrically coupled to the circuit(s) of the base layer by way of the plurality of middle layer through openings.

A top layer made of an electrically-insulating material is disposed over the middle layer. The top layer has a plurality of contact openings that coincide with each electrically-conductive contact pad of the middle layer proximal end portion and a plurality of sensor openings that coincide with each electrically-conductive contact pad of the middle layer distal end portion, thereby creating a substrate assembly with an substrate proximal end portion, an substrate distal end portion and an assembly middle portion extending longitudinally between the substrate proximal end portion and the substrate distal end portion. Each electrically-conductive contact pad at the second distal end portion is adapted to receive an electrode reagent to form a respective electrode and each electrically-conductive contact pad at the second proximal end portion is adapted to receive an electrical contact.

In another embodiment, the multi-layer, thin-film substrate assembly has multiple middle layers.

In another embodiment, the base layer, the circuit(s) of the first metallized layer, the middle layer, the middle layer circuits, and the top layer together impart an arcuate shape to the substrate assembly from the substrate proximal end portion to the substrate distal end portion.

In another embodiment of the substrate assembly, the electrically insulating material of each of the base layer, the middle layer, and the top layer is polyimide that is spun-formed and thermally cured.

In one embodiment of the substrate assembly, for example, the base layer and the middle layer have a thickness of about 10 microns. In another embodiment of the substrate assembly, the top layer has a thickness about five times the thickness of the middle layer. In another embodiment of the substrate assembly, the top layer has a thickness of about 55 microns. In another embodiment of the substrate assembly, the sensor assembly has a thickness of about 75 microns. In yet another embodiment, each of the substrate distal end portion and the assembly middle portion has a width of about 279 microns.

In another embodiment of the substrate assembly, the first metallized layer has a thickness in the range of about 900 Angstroms to about 1,500 Angstroms.

In another embodiment of the substrate assembly, the first metallized layer and the second metallized layer each includes gold. In another embodiment, the first metallized layer and the second metallized layer each includes a layer of chromium disposed against the base layer substrate and the middle layer substrate, respectively, and a layer of gold disposed on top of the layer of chromium. In another embodiment, the second metallized layer includes a layer of chromium disposed against the middle layer substrate, a layer of gold disposed on top of the layer of chromium, and a layer of platinum disposed on top of the layer of gold.

In another embodiment of the substrate assembly, the base layer has at least two circuits with respective electrically-conductive pads for each circuit at the base layer proximal end portion and the base layer distal end portion. The middle layer has at least two second-layer circuits with electrically-conductive pads for each second-layer circuit at the middle layer proximal end portion and the middle layer distal end portion. In one embodiment, for example, the first metallized layer of the base layer includes at least two additional electrically-conductive contact pads at the base layer distal end portion that aligns and coincides with the electrically-conductive pads at the middle layer distal end portion.

Another aspect of the present invention is directed to an electrochemical sensor assembly for use as a subcutaneous analyte sensor. In one embodiment, the electrode assembly has a base layer with a base layer substrate of electrically-insulating material that defines a base layer proximal end portion, a base layer distal end portion, and a base layer middle portion between the base layer proximal end portion and the base layer distal end portion. The base layer also has a first metallized layer disposed on the base layer substrate and defining at least one circuit extending longitudinally along the base layer substrate. Each circuit has an electrically-conductive contact pad formed at each of the base layer proximal end portion and the base layer distal end portion. An electrically-conductive trace electrically couples the electrically-conductive contact pad at the base layer proximal end portion with the electrically-conductive pad at the base layer distal end portion.

A middle layer is disposed over the base layer and has a middle layer substrate of electrically-insulating material. The middle layer substrate has a middle layer proximal end portion, a middle layer distal end portion, and a middle layer middle portion, where the middle layer is aligned with the base layer and has a plurality of second-layer through openings with side walls. Each of the plurality of second-layer through openings is in communication with a respective one of the electrically-conductive contact pad of the at least one circuit of the base layer. A second metallized layer is disposed on the middle layer substrate and the side walls of the second-layer through openings. The second metallized layer defines at least two circuits, where each of the second-layer circuits has an electrically-conductive contact pad formed at each of the middle layer proximal end portion and the middle layer distal end portion with an electrically-conductive trace electrically coupling the electrically-conductive contact pad at the middle layer proximal end portion with the electrically-conductive pad at the middle layer distal end portion. One of the at least two second-layer circuits is electrically coupled to the at least one circuit of the base layer by way of the plurality of second-layer through openings.

A top layer of electrically-insulating material is disposed over the middle layer. The top layer has a plurality of contact openings that coincide with each electrically-conductive contact pad of the middle layer proximal end portion and a plurality of sensor wells that coincide with each of the electrically-conductive contact pad of the middle layer distal end portion, thereby creating a substrate assembly with an substrate proximal end portion, an substrate distal end portion and an assembly middle portion extending longitudinally between the substrate proximal end portion and the substrate distal end portion.

A sensing layer is disposed on at least one electrically-conductive contact pad formed at the middle layer distal end portion to form at least a first working electrode. A reference layer is disposed on at least one electrically-conductive contact pad formed at the middle layer distal end portion forming a reference electrode. In another embodiment, there is further included a counter electrode and at least a second working electrode (also called a blank electrode because it is used to measure background current caused by interferents in the sample and not to measure a specific analyte). In still other embodiments, there are one or more additional working electrodes adapted to measure other specific analytes. In one embodiment, the at least first working electrode is a glucose measuring electrode.

In one embodiment, sensing layer includes three coating layers. A base coating later disposed directly on the metallized pad use to form a working electrode that contains PHEMA and glucose oxidase and/or glucose dehydrogenase, a second coating layer disposed directly on the base coating layer that contains PHEMA and a plurality of microspheres made of a material having substantially no or little permeability to glucose but a substantially high permeability to oxygen, and a third coating layer over the second coating layer, the third coating layer containing PHEMA and a material that prevents release of hydrogen peroxide from the sensing layer. In one embodiment, the microspheres are made from polydimethylsiloxane. In one embodiment, the third coating layer contains catalase.

In another embodiment, the base coating layer contains PHEMA, glucose oxidase and/or glucose dehydrogenase and a quantity of microspheres that is less that the quantity of microspheres in the second coating layer.

In another embodiment of the electrochemical sensor assembly, the base layer, the at least one circuit, the middle layer, the at least second-layer one circuit, and the top layer together impart an arcuate shape to the substrate assembly from the substrate proximal end portion to the substrate distal end portion.

In another embodiment of the electrochemical sensor assembly, each of the base layer substrate, the middle layer substrate, and the top layer substrate are polyimide that is spun-formed and thermally cured.

In another embodiment of the electrochemical sensor assembly, the base layer substrate and the middle layer substrate each have a thickness of about 10 microns. In another embodiment, the top layer has a thickness about five times the thickness of the middle layer substrate. In another embodiment, the top layer has a thickness of about 55 microns. In another embodiment, the sensor assembly has a thickness of about 75 microns. In another embodiment, each of the substrate distal end portion and the assembly middle portion has a width of about 279 microns.

In another embodiment of the electrochemical sensor assembly, the first metallized layer has a thickness in the range of about 900 Angstroms to about 1,500 Angstroms. In one embodiment, the first metallized layer and the second metallized layer each includes gold. In another embodiment, the first metallized layer and the second metallized layer each includes a layer of chromium disposed against the base layer substrate and the middle layer substrate, respectively, and a layer of gold disposed on top of the layer of chromium.

In another embodiment of the electrochemical sensor assembly, the second metallized layer includes a layer of chromium disposed against the middle layer substrate, a layer of gold disposed on top of the layer of chromium, and a layer of platinum disposed on top of the layer of gold.

In another embodiment of the electrochemical sensor assembly, the base layer includes at least two circuits, where one electrically-conductive pad with the sensing layer at the middle layer distal end portion forms a working electrode circuit, and where a second electrically-conductive pad at the middle layer distal end portion forms a blank electrode.

In another embodiment of the electrochemical sensor assembly, the base layer has at least two circuits and the middle layer has at least 2 circuits with respective electrically-conductive pads for each circuit at the respective distal end portion and the proximal end portion. In another embodiment, the first metallized layer of the base layer includes at least two additional electrically-conductive contact pads at the base layer distal end portion that align and coincide with the electrically-conductive pads at the middle layer distal end portion.

In another embodiment of the present invention, there is discloses a continuous glucose monitoring system. The system has an inserter assembly, a sensor housing cover assembly, and an electronic device. The inserter assembly has an inserter housing, a deployment button disposed within the inserter housing such that the deployment button is slidable from a first position to a second position only for deployment of a subcutaneous sensor into subcutaneous tissue through the skin, and a sensor housing for receiving and capturing a sensor deployment assembly from the deployment button where the sensor deployment assembly has a subcutaneous sensor. The sensor housing cover assembly configured for attachment to the sensor housing after insertion of the subcutaneous sensor where the cover assembly has an electronic module positioned for electronic coupling to the subcutaneous sensor and capable of storing and transmitting calculated data based on the input signals from the sensor. The electronic device is equipped with wireless communication for communicating with the electronic module of the sensor housing cover assembly. The electronic device having electronic circuits and software for receiving input signals from the sensor, converting the input signals to analyte data, displaying the analyte data on a user interface of the electronic device, storing the data for recall, and creating and/or sending reports of the data.

In another embodiment, the sensor of the continuous glucose monitoring system has a base layer with a base electrical circuit, a middle layer with middle electrical circuit where the middle layer has openings to the base layer electrically connecting portions of the middle electrical circuit with portions of the base electrical circuit.

In another aspect of the invention, a method of inserting an in-vivo analyte sensor subcutaneously for continuous analyte monitoring of a patient includes the steps of providing a single action inserter assembly having a needle, an implantable sensor, a deployment button for implanting the implantable sensor using the needle and for retracting the needle, and a sensor housing for retaining the implanted sensor in an implanted orientation once deployed by the deployment button; and using a single action to activate the deployment button of the single action inserter assembly that causes the following actions to substantially simultaneously occur: (1) implanting the sensor subcutaneously into the patient, (2) fixedly seating the sensor within the sensor housing attached to the patient, (3) retracting the needle into the inserter assembly, and (4) releasing the inserter assembly from the sensor housing.

In another embodiment of the method, the providing step includes providing a single action inserter assembly that has a lumen disposed on the needle and the using step includes implanting the lumen subcutaneously into the patient with the sensor and fixedly seating the lumen within the sensor housing attached to the patient.

In another aspect of the present invention, a continuous analyte monitoring inserter apparatus for subcutaneous placement of a sensor into skin of a patient minimizes pain to a patient. In one embodiment, the apparatus has a single action inserter assembly having a inserter housing with a first housing end and a second housing end. A deployment button is partially disposed in and slidable within the inserter housing through the first housing end, where the deployment button being movable between a first position and a second position. A sensor housing is partially disposed within and removably retained in the second housing end. A needle is movably disposed within the single action inserter assembly. The needle has a cross-sectional shape that minimizes a peak force of insertion into the skin of the patient. An implantable sensor is partially disposed within the needle. The inserter assembly is adapted to substantially simultaneously implant the sensor subcutaneously into the patient, retract the needle, fix the sensor within the sensor housing and release the inserter assembly from the sensor housing with a single activation of the deployment button caused by moving the deployment button from the first position to the second position while minimizing pain to the patient.

In another embodiment, a longitudinal portion of the needle has a skive cut along a length of the needle from a sharp end of the needle to a predefined location.

In another embodiment, the needle is oriented substantially perpendicular to a surface of the single action inserter, where the surface is a portion of the sensor housing and intended for placement against the skin of the patient.

In another embodiment, the needle has a cross-sectional shape of an oval, an ellipse, an egg-shape, or an oblong shape. In another embodiment, the longitudinal portion of the needle has a cross-sectional shape of an oval, an ellipse, an egg-shape, or an oblong shape.

In another aspect of the present invention is a method of minimizing pain when inserting an in-vivo analyte sensor subcutaneously for continuous analyte monitoring of a patient. In one embodiment, the method includes providing a single action inserter assembly having a needle with a cross-sectional shape that minimizes a peak force of insertion into the skin of the patient, an implantable sensor, a deployment button for implanting the implantable sensor using the needle and for retracting the needle, and a sensor housing for retaining the implanted sensor in an implanted orientation once deployed by the deployment button; and using a single action to activate the deployment button of the single action inserter assembly that causes the following actions to substantially simultaneously occur: (1) implanting the sensor subcutaneously into the patient, (2) fixedly seating the sensor within the sensor housing attached to the patient, (3) retracting the needle used to implant the sensor into the inserter assembly, and (4) releasing the inserter assembly from the sensor housing, wherein the needle and the single action minimizes pain when inserting the sensor subcutaneously.

In another embodiment of the method, the providing step includes providing a needle with a skive cut along a longitudinal portion of the needle from a sharp end of the needle to a predefined location along the length of the needle.

In another embodiment of the method, the providing step includes providing a needle that is oriented substantially perpendicular to a surface of the single action inserter, where the surface is a portion of the sensor housing and intended for placement against the skin of the patient.

In another embodiment of the method, the providing step includes providing a needle with an oval, elliptical, egg-shaped, or oblong cross-sectional shape. In another embodiment of the method, the providing step includes providing a needle with the longitudinal portion having an oval, elliptical, egg-shaped, or oblong cross-sectional shape.

In another aspect of the present invention, a method of making a sharp includes providing a longitudinal tubular body having a first end and a second end; compressing the longitudinal tubular body to have a substantially oval and/or elliptical cross-sectional shape; removing a portion of the tubular body proximate the first end and extending a predefined distance towards the second end where the portion is parallel to a major axis of the oval/elliptical cross-sectional shape; and forming a sharp tip on the first end.

In yet another aspect of the present invention, a method of continuous analyte monitoring includes placing an inserter assembly on an insertion site of a patient. The inserter assembly has a sensor carrier, an inserter set with a sharp and an analyte sensor, and a deployment assembly. The deployment assembly includes a deployment button, a inserter housing, and a deployment mechanism. The method also includes the steps of pressing the deployment button of the introducer set, thereby deploying the introducer set into subcutaneous tissue of the patient; retracting the deployment assembly and removing the sharp from the patient while leaving the analyte sensor deployed in the sensor carrier and in the patient; and removing the deployment assembly from the sensor carrier.

Another aspect of the present invention is directed to a method of forming a multi-layer, thin-film substrate assembly for use in forming a subcutaneous analyte sensor. In one embodiment, the method includes the steps of spin forming and thermally curing a polyimide base layer substrate into an elongated shape having a base layer proximal end portion, a base layer distal end portion and a base layer middle portion between the base layer proximal end portion and the base layer distal end portion; depositing a first metallized layer on the base layer substrate defining at least one circuit extending longitudinally along the base layer substrate, where the at least one circuit has an electrically-conductive contact pad formed at each of the base layer proximal end portion and the base layer distal end portion with an electrically-conductive trace electrically coupling the electrically-conductive contact pad at the base layer proximal end portion with the electrically-conductive pad at the base layer distal end portion; spin forming and thermally curing a polyimide middle layer substrate on the first metallized layer and the base layer substrate aligned with the base layer substrate, where the middle layer substrate defines a middle layer proximal end portion, a middle layer distal end portion and a middle layer middle portion between, where the middle layer proximal end portion and the middle layer distal end portion define a plurality of second-layer through openings having side walls, and where each of the plurality of second-layer through openings is in communication with a respective one of the electrically-conductive contact pad of the at least one circuit of the base layer; depositing a second metallized layer on the middle layer substrate and the side walls of the second-layer through openings to thereby define at least two circuits, where each circuit has an electrically-conductive contact pad formed at each of the middle layer proximal end portion and the middle layer distal end portion with an electrically-conductive trace electrically coupling the electrically-conductive contact pad at the middle layer proximal end with the electrically-conductive pad at the middle layer distal end portion, and where the at least one circuit is electrically coupled to the at least one circuit of the base layer by way of the plurality of second-layer through openings; and spin forming and thermally curing a polyimide top layer over the middle layer substrate and the second metallized layer, where the top layer defines a plurality of openings that coincide with each electrically-conductive pad of the middle layer to thereby create a substrate assembly with an substrate proximal end portion, an substrate distal end portion, and an assembly middle portion extending longitudinally between the substrate proximal end portion and the substrate distal end portion, and where each electrically-conductive contact pad at the middle layer distal end portion is adapted to receive an electrode reagent to form a respective electrode and each electrically-conductive contact pad at the middle layer proximal end portion is adapted to receive an electrical contact.

In one embodiment, a method of inserting a sensor subcutaneously is disclosed. The method includes providing an inserter assembly containing a sensor and an insertion needle adapted for implanting the sensor into subcutaneous tissue wherein the inserter assembly requires a user-perpetrated initial applied force of greater than 1.5 lbs. that is followed by a decrease in applied force to an applied force of less than 1.5 lbs, placing the inserter assembly against a patient's skin, actuating the inserter assembly to thereby implant the sensor subcutaneously and disengaging a sensor housing containing the implanted sensor from the inserter assembly, and removing the inserter assembly from the patient's skin. In this embodiment, the removed inserter assembly is the actuation assembly.

In another embodiment, the providing step includes an inserter assembly that requires a user-perpetrated initial applied force in the range of 1.5 to 2.5 lbs. followed by a decrease in the applied force for insertion of the needle into the subcutaneous tissue wherein the applied force of the insertion needle is in the range of about 0.5 lbs to about 1.3 lbs.

In one embodiment, a method of inserting a sensor subcutaneously is disclosed. The method includes providing an inserter assembly containing a sensor and an insertion needle adapted for implanting the sensor into subcutaneous tissue wherein the inserter assembly is adapted to insert the sensor into the subcutaneous tissue and release a post-actuation assembly after implantation in less than one second, placing the inserter assembly against a patient's skin, actuating the inserter assembly to thereby implant the sensor subcutaneously and disengaging a post-actuation inserter assembly in less than one second, and discarding the post-actuation inserter assembly.

In another embodiment, the providing step includes providing an inserter assembly capable of implanting the sensor subcutaneously and releasing the popst-actuation assembly after implantation in a time period that is less than 0.5 seconds, a range of less than 0.25 seconds to 0.8 seconds, a range of less than 0.5 seconds to 0.8 seconds, a range of 0.5 seconds to 0.8 seconds, a range of 0.25 seconds to 0.5 seconds, and 0.5 seconds.

In another embodiment, the actuation step includes implanting the sensor subcutaneously and disengaging the post-actuation inserter assembly in a time period of less than 0.5 seconds, a range of less than 0.25 seconds to 0.8 seconds, a range of less than 0.5 seconds to 0.8 seconds, a range of 0.5 seconds to 0.8 seconds, a range of 0.25 seconds to 0.5 seconds, and 0.5 seconds.

BRIEF DESCRIPTION OF THE DRAWINGS

FIG. 6 is a graph showing data for one inserter set of the present invention, where insertion force is plotted against the distance of insertion and where the area under a curve is the work energy.

FIG. 8 is a perspective view of the inserter assembly of FIG. 7.

FIG. 9 is a cross-sectional side view of the inserter assembly of FIG. 8.

FIG. 10 is an exploded perspective view of the inserter assembly of FIG. 8.

FIG. 10A is an exploded side view of the sensor inserter assembly of FIG. 8.

FIG. 11 is a side view of the deployment button assembly of the inserter assembly of FIG. 8 showing the deployment button, the needle assembly and the sensor deployment assembly assembled for use.

FIG. 12 is a front view of the deployment button assembly of FIG. 11.

FIG. 13 is a cross-sectional side view of the deployment assembly of FIG. 11.

FIG. 14 is a cross-sectional front view of the deployment button assembly of FIG. 12.

FIG. 15 is a side view of the inserter housing assembly of the inserter assembly of FIG. 8 showing the inserter housing and the sensor housing.

FIG. 16 is a front view of the inserter housing assembly of FIG. 15.

FIG. 17 is a cross-sectional side view of the inserter housing assembly of FIG. 15 showing the inserter housing with one or more cam surfaces and the sensor housing.

FIG. 18 is a cross-sectional view of the inserter housing assembly of FIG. 16 showing the bendable and resilient sensor housing retaining members.

FIG. 44 is a plan view of the sensor of FIG. 42 showing the base layer only with an electrical contact portion and a sensor end portion circled.

FIG. 45 is an enlarged view of the electrical contact portion of FIG. 44.

FIG. 46 is an enlarged view of the sensor end portion of FIG. 44.

FIG. 47 is a plan view of the sensor of FIG. 42 showing the middle layer only with an electrical contact portion and a sensor end portion circled.

FIG. 48 is an enlarged view of the electrical contact portion of FIG. 47.

FIG. 49 is an enlarged view of the sensor end portion of FIG. 47.

FIG. 55 is a flow chart showing the steps of the process of depositing the reagent layers onto the sensor substrate forming the functional electrodes of the sensor.

DETAILED DESCRIPTION OF THE PREFERRED EMBODIMENT

Figure 4:
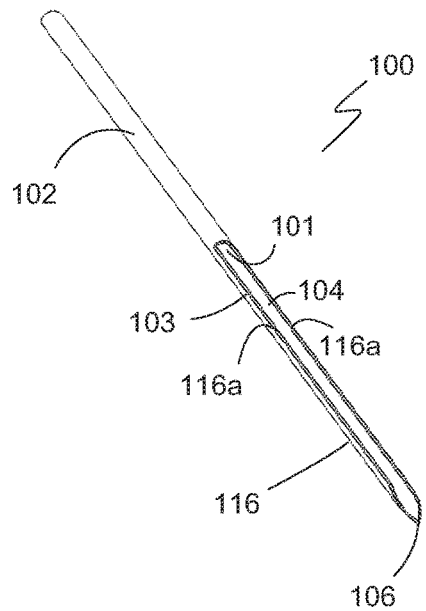
FIG. 4 is a perspective view of one embodiment of a sharp of the present invention showing the sharp tip, a sharp open region, and a portion of the sharp body.
Figure 5:
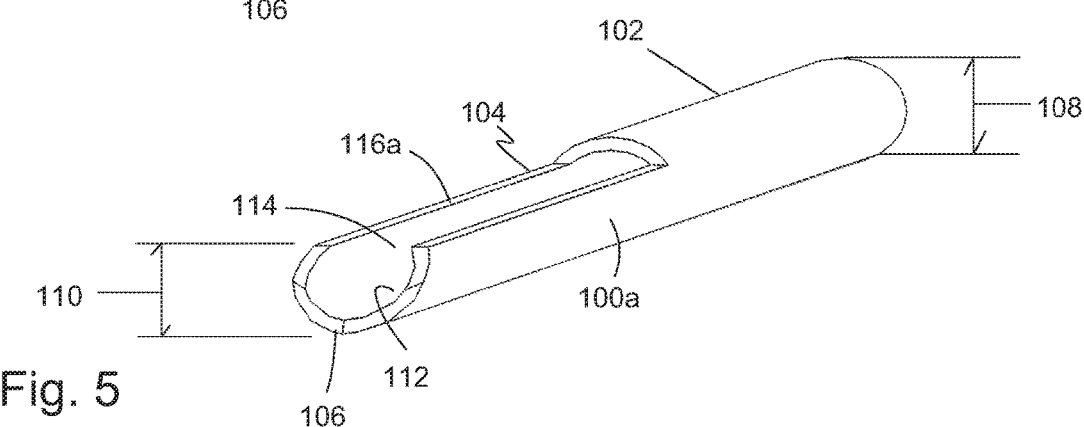
FIG. 5 is an end perspective view of the sharp of FIG. 4 showing the concave well defined by the sharp open region.

Exemplary embodiments of the present invention are illustrated in FIGS. 4-55. FIGS. 4 and 5 illustrate perspective views of one embodiment of a needle/sharp 100 of the present invention. Needle/sharp 100 includes a sharp body 102, a sharp open region 104, and a sharp tip 106. Sharp body 102 is an annular section of sharp 100 that extends longitudinally and defines an enclosed conduit 101 therethrough. In one embodiment, sharp 100 is made from 27 gauge XTW stainless tubing having an outside diameter of about 0.016 inch (0.41 mm) nominal and an inside diameter of about 0.012 inch (0.30 mm) nominal. The tubing is then flattened to have an oval or elliptical shape with an outside height 108 along the minor axis of the oval or elliptical shape of about 0.0120 inch (0.30 mm). With the new sensor fabrication discussed later, it is possible that a smaller sharp 100 made from 28 gauge XTW stainless steel tubing having an outside diameter of about 0.014 inch (0.36 mm) nominal and an inside diameter of about 0.011 inch (0.28 mm) nominal.

A wire EDM machining operation or a laser operation is used to remove a portion of the tubing wall 103 along sharp 100 a predefined distance to define sharp open region 104, thereby reducing the overall height 110 of sharp 100 along the minor axis of the oval or elliptical shape at sharp open region 104 to about 0.008 inches (0.20 mm). Both the wire EDM machining operation and the laser operation can be performed on cylindrical tubing or on flattened, oval tubing as described above. Sharp open region 104 is a section of an annulus that extends longitudinally with the tubing wall 103 along the length of sharp open region 104 defining an unenclosed concave well 114 from sharp tip 106 to sharp body 102.

Figure 5A:
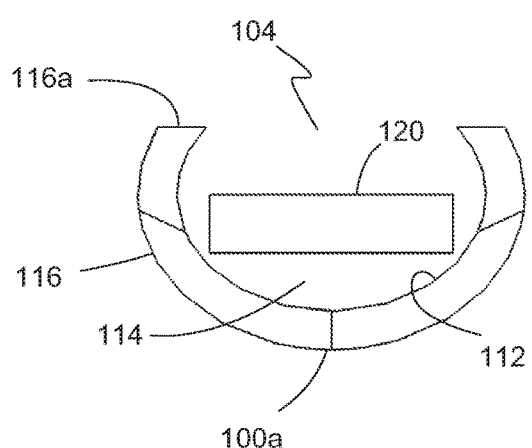
FIG. 5A is a diagram representing the cross-sectional area of the sharp open region of the sharp of FIG. 5 with a sensor disposed in the concave well.

Concave well 114 is sized to receive a continuous monitoring sensor 120. In one embodiment, concave well 114 is sized to receive a continuous monitoring sensor 120 having a size up to about 0.011 (0.28 mm) wide by about 0.003 (0.075 mm) thick. In one embodiment, a continuous monitoring sensor top surface 122 (not shown) is positioned flush with or below a top surface 116a of tubing wall 116 along sharp open region 104. The incision of such a sharp and sensor combination has a cross sectional area 112 of about $1.33 \times 10^{-3}$ in$^2$ (0.81 mm$^2$), where cross sectional area 112 is defined within outside surface 100a of tubing wall 103 and top surface 116a of tubing wall 116 at sharp open region 104 (also shown in FIG. 5A). Having continuous monitoring sensor 120 disposed in concave well 114 of sharp 100 minimizes the combined cross sectional area of the sharp and sensor as compared to cylindrical sharps of the same tubing or cylindrical sharps with a sharp open region but a continuous monitoring sensor that extends out of the sharp open region. Thus, the insertion force for sharp 100 with continuous monitoring sensor 120 is considerably lower than the insertion force of prior art insertion sets.

Referring now to FIG. 6, a plot 80 shows insertion force data for inserter set 200 of the present invention with force of insertion 82 plotted vs. the distance 84 of insertion. Each of plotted lines 86 in FIG. 6 represents a separate measurement at a different, nearby insertion site. The force of insertion 82 (lb) is plotted against the distance or depth of insertion 84 (inches). As shown in FIG. 6, the force of insertion 82 is substantially constant with only modest increases beyond a depth 84 of about 0.1 inches (2.5 mm), even when the insertion depth 84 is about 0.3 inches (7.6 mm). By inserting sharp 100 in a direction perpendicular to the tissue surface, inserter set 200 can deposit continuous monitoring sensor 120 into the critical subcutaneous layer with minimal trauma to the tissue. The typical insertion depth during use is from 4 mm to 7 mm for accurate measurement of subcutaneous glucose. Other inserter designs insert a sharp at angles of about 45 degrees (more or less) thus increasing length of insertion by 41%. Work energy (force times distance; the area under a curve 86) has been shown to be proportional to the incidence of pain response reported by users.

To further reduce or minimize the pain of insertion, sharps 100 of the present invention are used in an inserter assembly 200 that deploys continuous monitoring sensor 120 into skin tissue. Introducer designs that rely on the patient to drive sharp 100 into the patient's own tissue greatly benefit the patient by providing low-force and low-work designs. This benefit derives from psychological reasons as well as from the practical aspect of having to insert a sharp into a relatively soft abdomen or hip.

Figure 7:
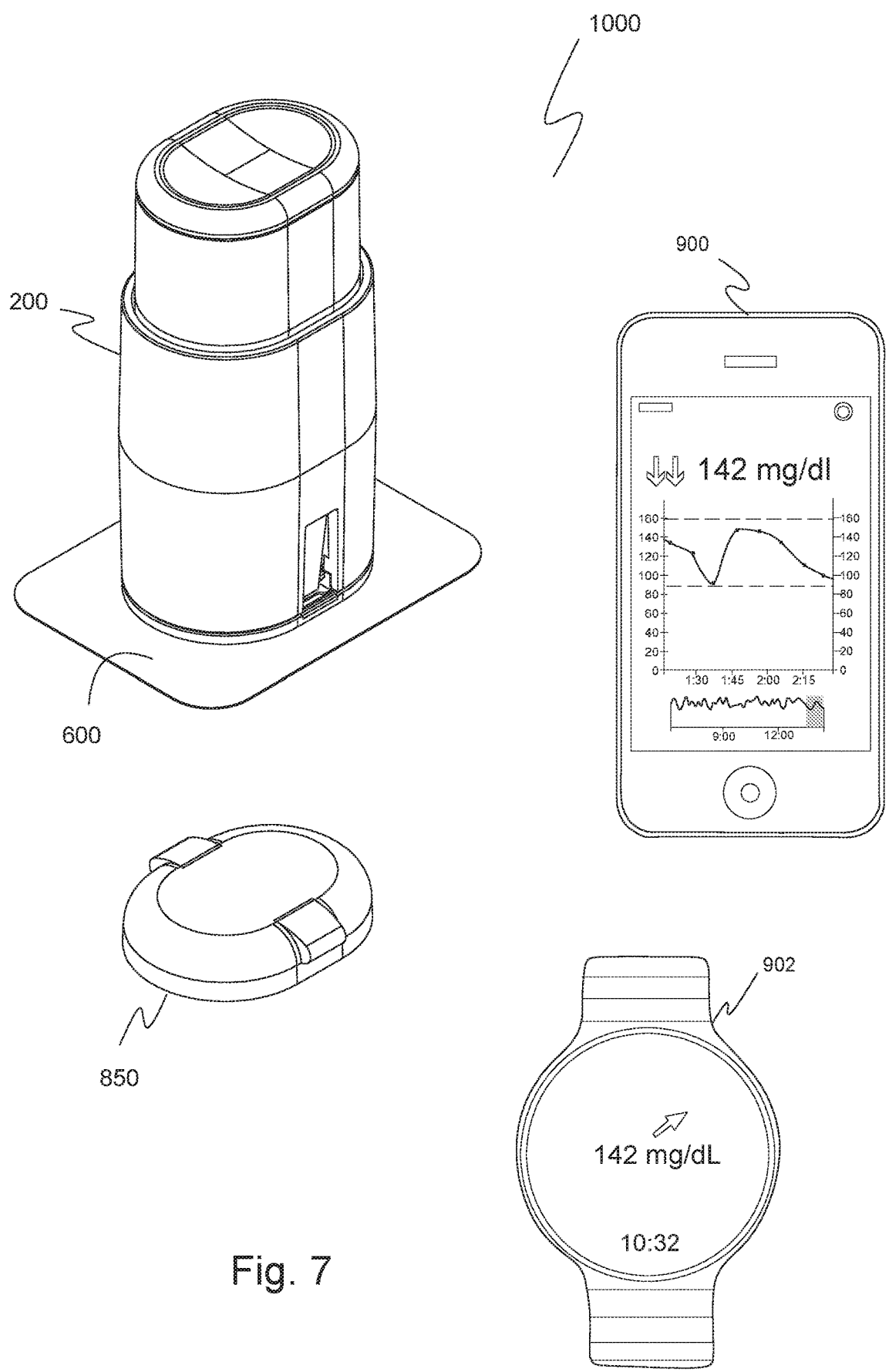
FIG. 7 is a perspective view of one embodiment of a CGM system of the present invention showing a sensor inserter assembly, a sensor housing cover and display modules.

Referring now to FIG. 7, there is illustrated one embodiment of the CGM system 1000 of the present invention. CGM system 1000 includes an inserter assembly 200, a sensor housing cover assembly 850, and an electronic device 900, 902 that is equipped for wireless communication. An adhesive component 600, which is adhesively attached to a bottom of the inserter assembly 200 also has an adhesive layer on an opposite side of the adhesive component for adhesively attaching the inserter assembly 200 to the skin of a patient. Adhesive component 600 may optionally be part of the CGM system 1000 or a separate component that is attached to the bottom of inserter assembly 200 only when inserter assembly 200 is about to be used.

FIGS. 8 and 9 illustrate perspective and a cross-sectional views, respectively, of one embodiment of inserter assembly 200 of the present invention. Inserter assembly 200 includes an inserter housing 202, a deployment button 204 slidably received in inserter housing 202, and a sensor housing 206 removably captured by inserter housing 202. A housing locking mechanism 205 (e.g., resilient tab, clip, protrusion, etc.) retains sensor housing 206 captured by inserter housing 202 until deployment of deployment button 204. Inserter housing 202 has a first housing end 213 and a second housing end 215 with deployment button 204 at least partially disposed in and slidable within inserter housing 202 through first housing end 213. A needle assembly 208 is operable with deployment button 204, inserter housing 202, and sensor housing 206. Inserter housing 202 includes one or more recesses 212 (not shown) for engagement with deployment button 204 to maintain deployment button 204 and inserter housing 202 connected to each other at all times after assembly of inserter assembly 200 and even after use of inserter assembly 200, as is discussed in more detail below. The combination of inserter housing 202, deployment button 204, needle assembly 208, button cap 203, and sensor housing 206 form an actuation assembly 201.

Inserter housing 202 includes at least one first catch surface 210 (shown in more detail in FIGS. 17 and 22) defined by a recess, opening, ledge, protrusion, or other structure. First catch surface 210 is constructed and sized to engage a corresponding resilient locking catch 214 (shown in FIGS. 11, 12) on deployment button 204. First catch surface 210 locks deployment button 204 within inserter housing 202 when first assembled and prevents inadvertent or deliberate separation of deployment button 204 from inserter housing 202 post assembly. Inserter housing 202 also includes a second catch surface 210' that is also defined by a recess, opening, ledge, protrusion, or other structure. Second catch surface 210' is positioned lower within inserter housing 202 than first catch surface 210. Both first and second catch surfaces 210, 210' are aligned with each other with a housing cam surface 211 formed into a housing wall 218 between each of first and second catch surfaces 210, 210'. When deployment button 204 is in the first (ready) position), locking catch 214 is held by abutment with first catch surface 210 of housing wall 218. When the user presses deployment button 204 down, a tension is initially created in locking catch 214 by movement of locking catch from first catch surface 210 onto cam surface 211. Cam surface 211 is configured to allow locking catch 214 to move outward along cam surface 211 towards its resting, non-tensioned orientation to engage second catch surface 210'. Of course, inserter housing 202 and deployment button 204 can be configured so that first and second catch surfaces 210, 210' are on deployment button 204 and locking catch 214 is on inserter housing 202. Other releasable locking mechanisms known in the art are also acceptable.

As can be seen in FIG. 9, deployment button 204 further includes a needle assembly 208 that is slidably received in a deployment mechanism cavity 228 in deployment button 204. A deployment cap 230 closes deployment mechanism cavity 228 to prevent access to needle assembly 208. Needle assembly 208 includes a deployment spring 232, a needle/sharp carrier 234 with a needle carrier catch 235, a hollow, slotted needle 100, and a sensor deployment assembly 236. Deployment spring 232 (e.g., a coil spring) is disposed between a spring support component 231 and needle carrier 234 in a tensioned orientation. Needle carrier catch 235 prevents needle carrier 234 from being moved towards deployment cap 230 by deployment spring 232. Deployment button 204, needle assembly 208, deployment cap 230, and inserter housing 202 together create a cam follower deployment structure 217. When the user presses deployment button 204, needle carrier catch 235 is released from a button catch surface 240 by a carrier release surface 203 of inserter housing 202 and deployment spring 232 then biases needle carrier 234 towards deployment cap 230.

FIGS. 10 and 10A are exploded perspective and exploded side views of inserter assembly 200 showing the various components that make up inserter assembly 200. Sensor housing 206 is attached to second housing end 215 of inserter housing 202. An assembly gasket 802 is positioned between a perimeter of sensor housing 206 and second housing end 215. A sensor housing grommet 251 is attached to a bottom opening 206b' that receives needle 100 and sensor 120 during subcutaneous insertion of sensor 120. Assembly gasket 802 and grommet 251 are hermetically bonded to sensor housing 206. Sensor deployment assembly 236 includes a lower deployment body 270, an upper deployment body 236a, a sensor 500 that has a proximal end portion 501 captured between lower deployment body 270 and upper deployment body 236a, and a distal end portion 502 that extends through and beyond lower deployment body 270. Sensor deployment assembly 236 is attached to a second button end 204b, which is later released and attached to sensor housing 206 during use. Needle assembly 208 is received within deployment button 204 and retained within deployment button 204 by deployment cap 230. Needle carrier 234 has at least one, elongated side wing 234a that slides into a cavity slot 228a of deployment mechanism cavity 228 to prevent needle assembly 208 and needle 100 from rotating within deployment mechanism cavity 228. Needle carrier 234 also includes at least one needle carrier catch 235.

FIGS. 11 and 12 are side and front plan views of one embodiment of a button assembly 220. Button assembly 220 is a sub-assembly of inserter assembly 200. Button assembly 220 include deployment button 204, needle assembly 208 received within deployment button 204, deployment cap 230, and sensor deployment assembly 236. In this embodiment, locking catch 214 is part of deployment button 204. Deployment button 204 also includes a sensor deployment assembly catch 214' that retains sensor deployment assembly 236 to deployment button 204 within inserter assembly 200 until deployment button 204 is activated.

FIGS. 13 and 14 are cross-sectional side and front views of the embodiments shown in FIGS. 11 and 12, respectively. In FIG. 13, needle assembly 208 is positioned to maintain the compression of deployment spring 232 while in the ready position. Needle carrier catch 235 is in a relaxed state and contacts button catch surface 240, which prevents deployment spring 232 from driving needle carrier 234 up towards deployment cap 230. In FIG. 14, sensor deployment assembly catch 214' holds sensor deployment assembly 236 against a portion of second button end 204b. In each of FIGS. 11-14, a portion of sensor 500 is disposed within needle 100.

Turning now to FIGS. 15-18, there is illustrated one embodiment of an inserter housing assembly 222. FIGS. 15 and 16 are side and front plan views of inserter housing assembly 222. Inserter housing assembly 222 includes inserter housing 202, sensor housing 206 and assembly gasket 802. Housing locking mechanism 205 retains sensor housing 206 at second housing end 202b. FIG. 17 shows a housing cam surface 211 with first catch surface 210 and second catch surface 210' where housing cam surface 211 extends between first and second catch surfaces 210, 210'. The relationship of housing cam surface 211, first catch surface 210 and second catch surface 201' with deployment button 204 is more clearly described later with respect to FIGS. 19-26 as well as the interactions of the various locking/holding/releasing structures of inserter assembly 200. FIG. 18 more clearly shows housing locking mechanism 205 in its normal position with a locking mechanism end catch 205a retaining sensor housing 206 where locking mechanism end catch 205a interacts with a sensor housing catch surface 206a. Also illustrated is a sensor deployment assembly retaining component 217 that is integral with and unitarily formed with sensor housing 206.

Figure 19:
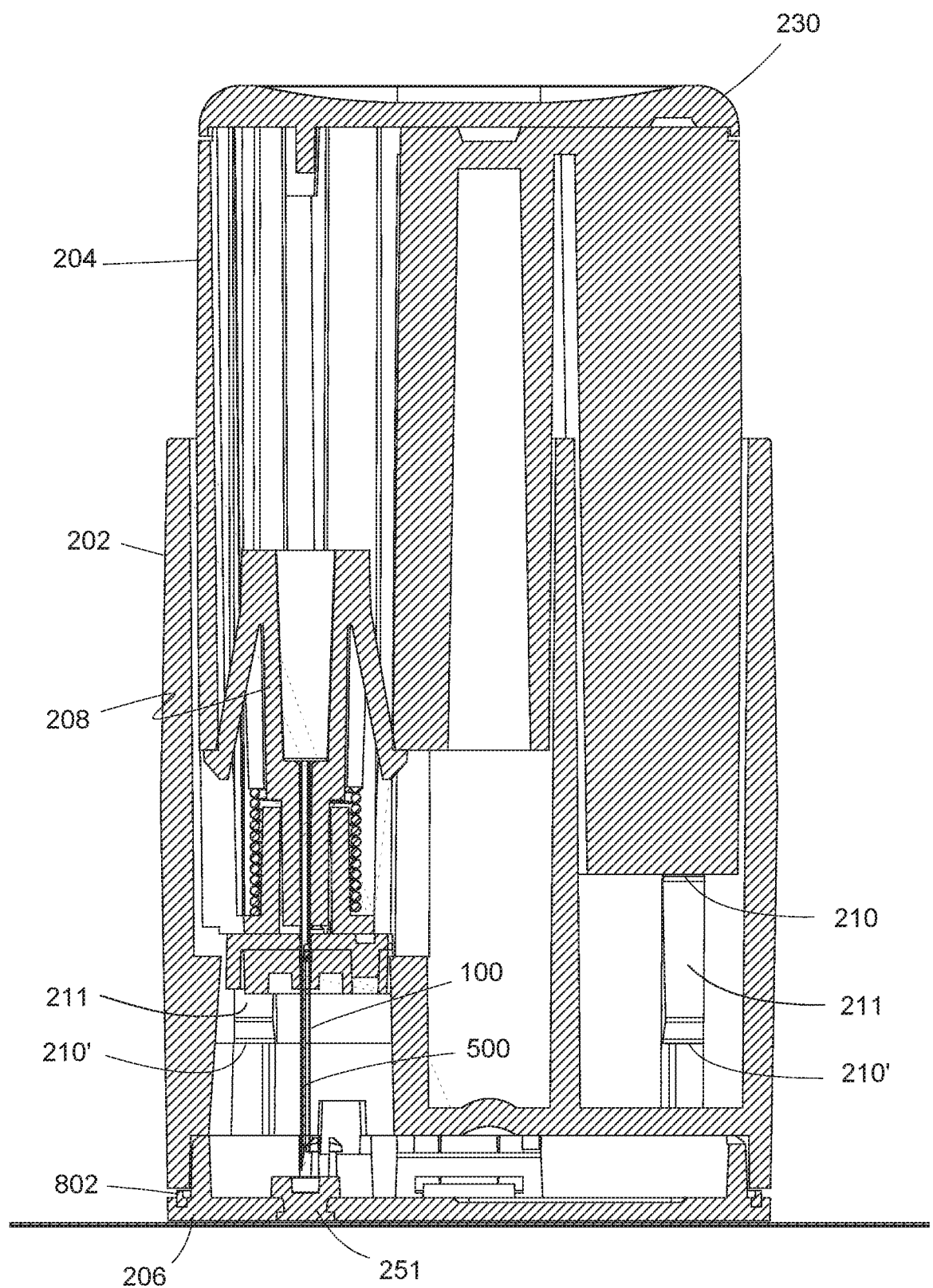
FIG. 19 is a cross-sectional side view of one embodiment of the inserter assembly showing a sensor housing, inserter housing, a needle assembly, a sensor deployment assembly, a deployment button, and a deployment button cover.

FIG. 19 is an enlarged, cross-sectional, side view of inserter assembly 200 in a ready-to-use position. This figure is of particular interest because it can be seen that sensor 500 is disposed within needle 100 and needle 100 is aligned with sensor housing grommet 251 and ready for insertion into the subcutaneous tissue of a patient. Also, cam surface 211 of inserter housing 202 is more clearly shown with first and second catch surfaces 210, 210', respectively.

Figure 20:
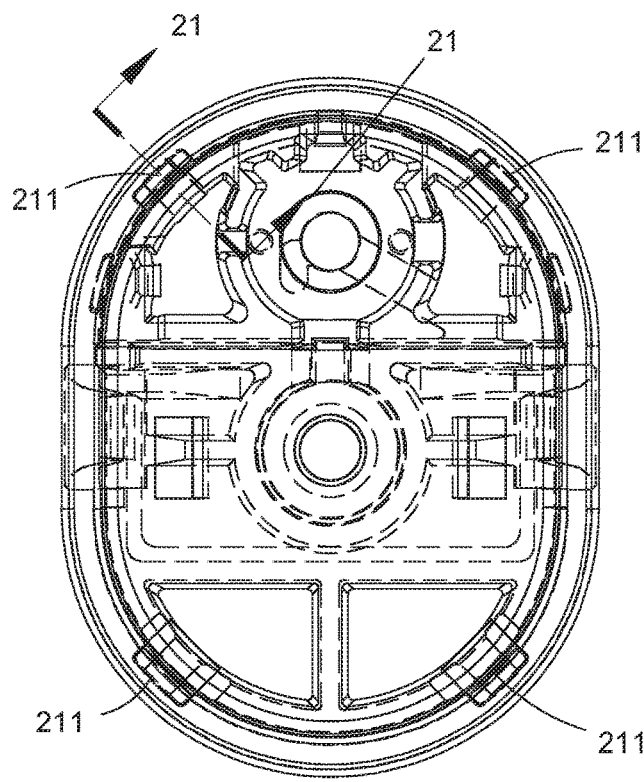
FIG. 20 is a top view of a deployment button within an inserter housing showing a view line 21-21 through one of the cam surfaces.

FIG. 20 is a top view of inserter housing assembly 222 with a view line 21-21 taken longitudinally through cam surface 211. It should be noted that in this embodiment, there are four cam surfaces 211 where each one of the cam surfaces 211 interacts with one of four resilient locking catches of deployment button 204 but that fewer or greater number of resilient locking catches may optionally be preferred.

Figure 21:
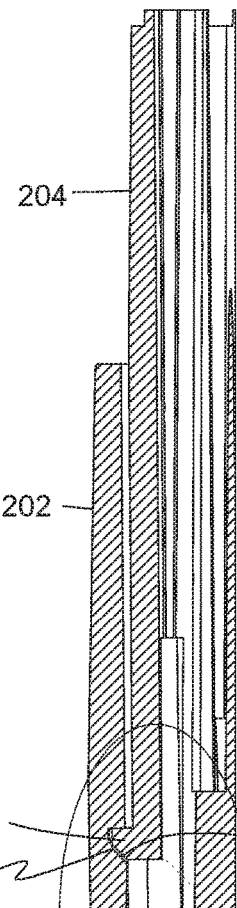
FIG. 21 is a cross-sectional view of the deployment button and the inserter housing taken alone the view line 21-21 in FIG. 20.
Figure 22:
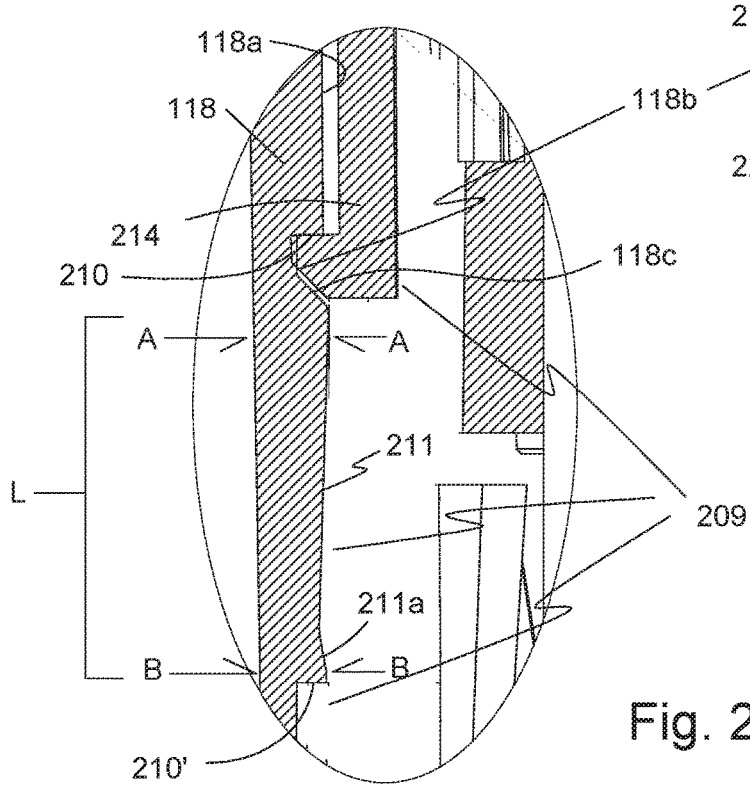
FIG. 22 is an enlarged view of the cam surface and deployment button retaining member outlined in FIG. 21.

FIG. 21 is a cross-sectional view of inserter housing assembly 222 taken along view line 21-21 in FIG. 20. This cross-sectional view shows the contour of cam surface 211 with resilient locking catch 214 holding deployment button 204 in a ready-to-use position while preventing separation of deployment button 204 from inserter housing 202 post assembly. FIG. 22 is an enlarged view of the corresponding area outlined by reference ellipse 22 in FIG. 21. As seen in FIG. 22, resilient locking catch 214 is captured by first catch surface 210, which prevents deployment button 204 from being easily and inadvertently separated from inserter housing 202 once assembled to inserter housing 202. In this embodiment, a recess 118b formed into an inside surface 118a of housing wall 118 creates first catch surface 210 where first catch surface 210 is transverse to inside surface 118a such that when deployment button 204 is assembled within (i.e. inserted into) inserter housing 202, resilient locking catch 214 is biased inwardly by housing wall 118 until deployment button 204 reaches a predefined location defined by recess 118b and first catch surface 210. When resilient locking catch 214 reaches recess 118b of first catch surface 210, locking catch 214 is forced into recess 118b and butts up against first catch surface 210, which is caused by the imparted bias of the resilient locking catch 214 moving to a more relaxed state. Recess 118b also has a sloping recess surface 118c that extends back towards inside surface 118a and away from first catch surface 210. Sloping recess surface 118c resists deployment of deployment button 204, which requires an initial applied force of greater than 1.5 lbs. followed by an applied force of less than 1.5 lbs. The initial applied force, also called the actuation force, is an applied force of less than 2.5 lbs. (1.13 kg) but greater than 1 lb. (453.6 g), which is discussed below. The combination of cam surface 211, cam surface portion 211a, recess 118b, sloping recess surface 118c, first and second catch surfaces 210, 210', and resilient locking catch form a cam follower deployment structure 209.

Along cam surface 211, housing wall 118 decreases in thickness from or adjacent to inside surface 118a at a location adjacent first catch surface 210 as indicated by arrows A along a predefined distance L to a second location as indicated by arrows B adjacent second catch surface 210'. As shown in FIG. 22, cam surface 211 changes direction and a cam surface portion 211a slopes towards inside surface 118a of housing wall 118 for a short distance to second catch surface 210'. The distance between first and second catch surfaces 210, 210' for this embodiment is about 0.44 inches (about 11.1 to 11.2 mm). Cam surface portion 211a causes a small increase in deployment force caused by cam surface portion 211a forcing resilient locking catch 214 back towards a more biased orientation before releasing into second catch surface 210'.

Figure 1:
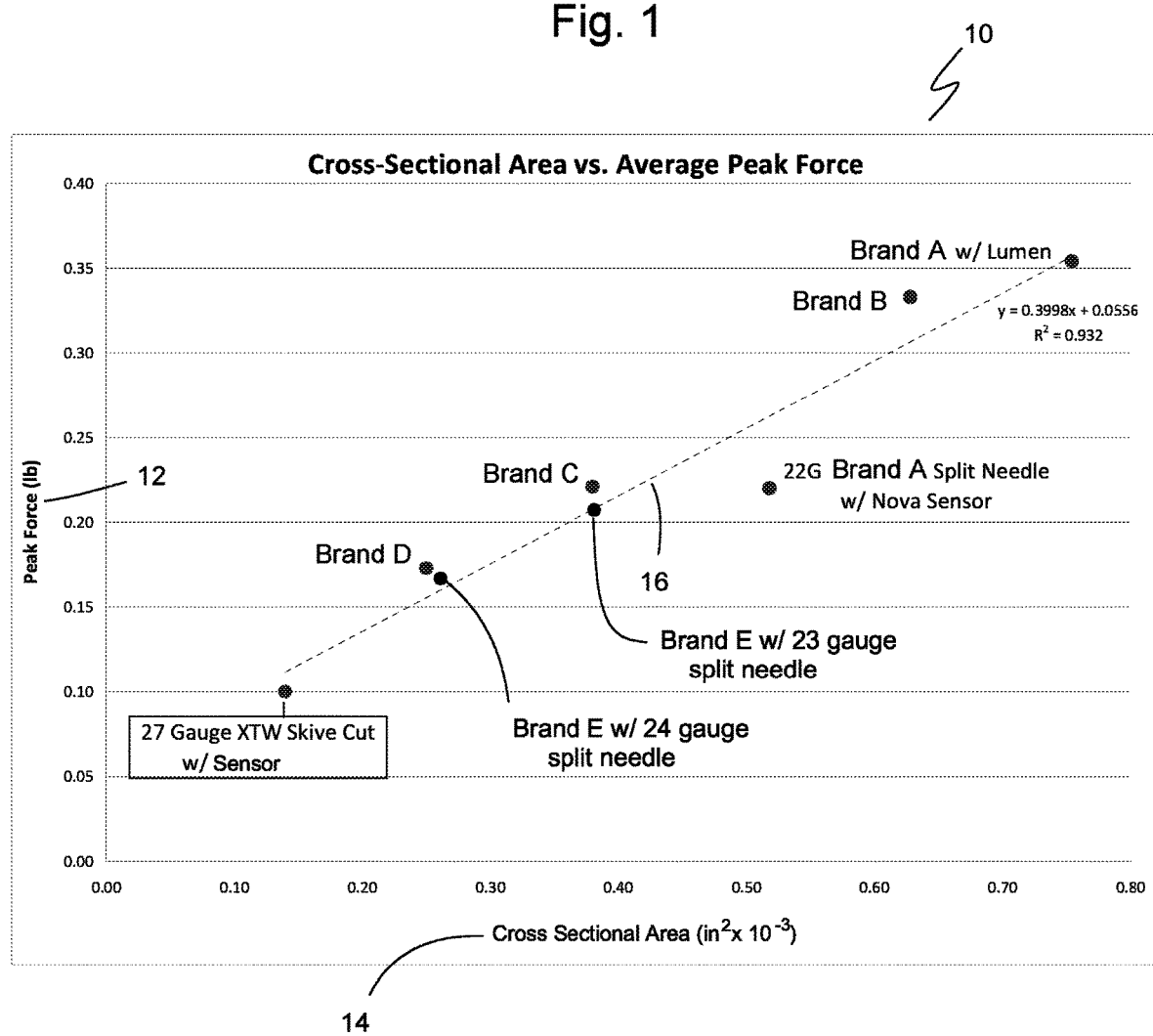
FIG. 1 is a graph showing insertion force data for various commercial inserter sets of the prior art, where maximum peak force of insertion is plotted against the measured cross sectional area of the inserter set.
Figure 2:
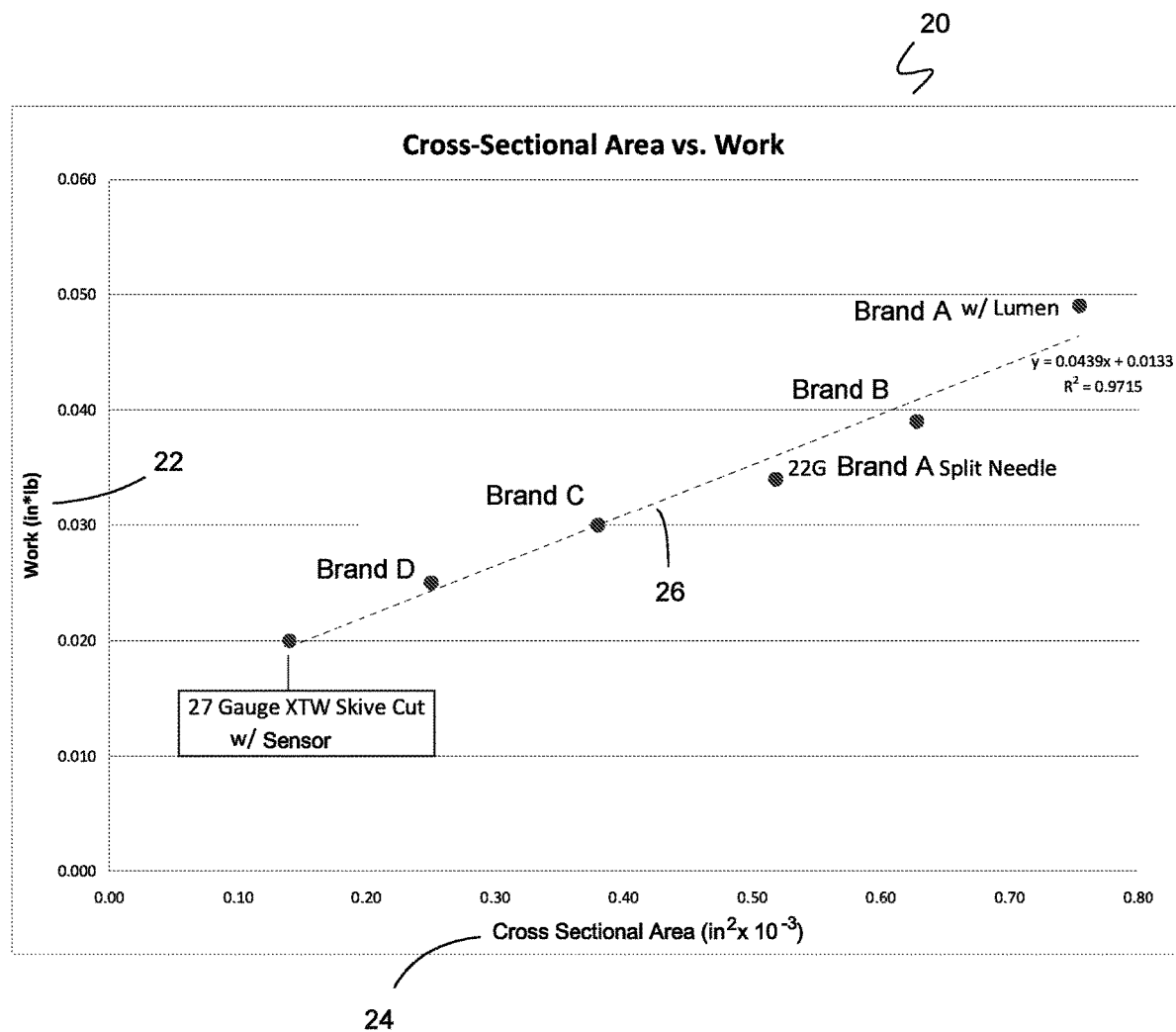
FIG. 2 is a graph showing data for various commercial inserter sets of the prior art, where the work of insertion is plotted against the measured cross sectional area of the inserter set.

The cam follower deployment structure 209 was deliberately designed to provide the patient a tactile feel during deployment as well as to build momentum during actuation. The profile of cam follower deployment structure 209 determines the initial deployment force required for actuation. The insertion force of the needle was previously discussed in relation to FIGS. 1, 2 and 6. However, needle insertion force is not the only factor that determines the successful deployment of a subcutaneous sensor. The design of the insertion mechanism, the actuation force and the needle insertion force combine to determine the comfort or discomfort experienced by the patient. It is important to note that for continuous glucose monitoring (CGM) systems, it is the patient who typically self-administers by performing the insertion and deployment of the needle and glucose sensor into the patient's own subcutaneous tissue. This is akin to self-mutilation since pain is typically associated with a needle piercing the skin. Inflicting pain on oneself is not a natural state of being. For most patients, this is difficult to do to oneself. All of the brands disclosed in FIGS. 1, 2 and 6 either use comparatively larger needles and/or use an insertion mechanism that could cause a patient to not follow through completely during the insertion process of the needle and subcutaneous sensor before the subcutaneous sensor is fully implanted and released from the insertion needle. Cam surface 211 and the cam follower (i.e. resilient locking catch 214) provides a quick and easy mechanism that completes the sensor deployment process and removal of the deployment mechanism from the inserted subcutaneous sensor once the patient actuates the deployment mechanism such that the patient has no control over the insertion action once activated with respect to insertion of the subcutaneous sensor because of the applied force profile during use of the inserter assembly 200. In other words, the patient is unable to consciously or subconsciously not follow through to completing the sensor implantation process by lessening the insertion/applied force on the inserter assembly.

Relationship of Actuation Force, Needle Insertion Force and Inserter Assembly

The relationship of actuation force, needle insertion force and the inserter assembly with cam surface 211 and cam follower/resilient locking catch 214 is explored using a Mecmesin 2.5xt Force Tester. Five samples were deployed using the Mecmesin 2.5xt Force Tester as the method of actuation. The specific test setup included a 50N load cell, a sample frequency of 100 Hz, displacement of 0.44 inches, a speed of 10 inches per minute, synthetic skin such as, for example, SIP-10 by SIMUlab, and inserter assembly 200 of the present invention. The Mecmesin Force Tester was set up to push deployment button 204 on inserter assembly 200. The load cell measures a compressive force, which is the reaction force imposed by the cam mechanism (i.e. cam surface 211 and resilient locking catch 214) as well as the needle penetration of the synthetic skin sample. The Mecmesin will capture/record the peak force, the average force and calculate the work/energy under the generated curve for each sample.

Table 1 shows the data recorded by the Mecmesin 2.5xt Force Tester of the deployment force with needle. As previously described, the peak force, work and average force was recorded for each of the five inserter assemblies 200.

TABLE 1

| Deployment Force with Needle | | | |
| --- | --- | --- | --- |
| Sample | Peak Force (lbf) | Work (lbf · in) | Average Force (lbf) |
| 1 | 2.1648 | 0.303758 | 0.6784 |
| 2 | 2.2086 | 0.361481 | 0.7623 |
| 3 | 2.2674 | 0.415904 | 0.8861 |
| 4 | 1.9226 | 0.361209 | 0.7674 |
| 5 | 2.0959 | 0.307079 | 0.6776 |
| MEAN | 2.1319 | 0.349886 | 0.7543 |
| SD | 0.133 | 0.0463 | 0.0855 |
| MIN | 1.9226 | 0.303758 | 0.6776 |
| MAX | 2.2674 | 0.415904 | 0.8861 |

Figure 23:
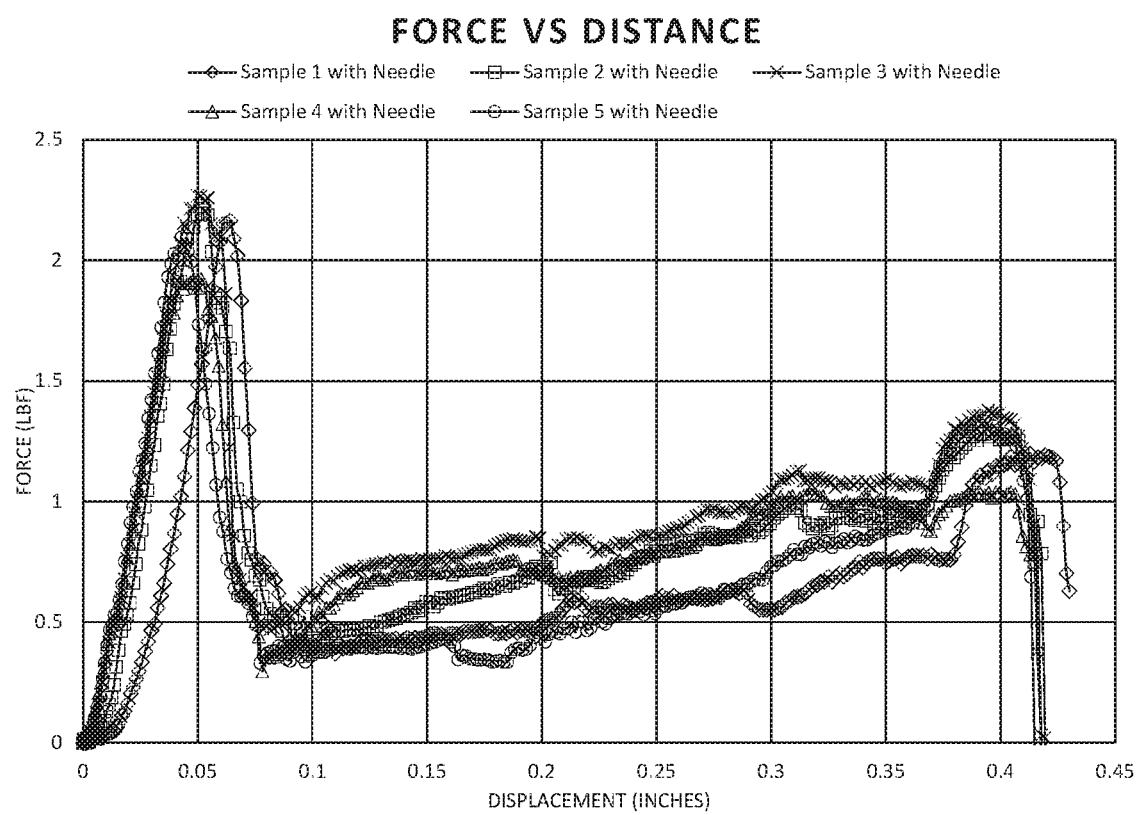
FIG. 23 is a graph showing force versus distance for five samples with needles of the inserter with the cam surface being deployed into synthetic skin.
Figure 24:
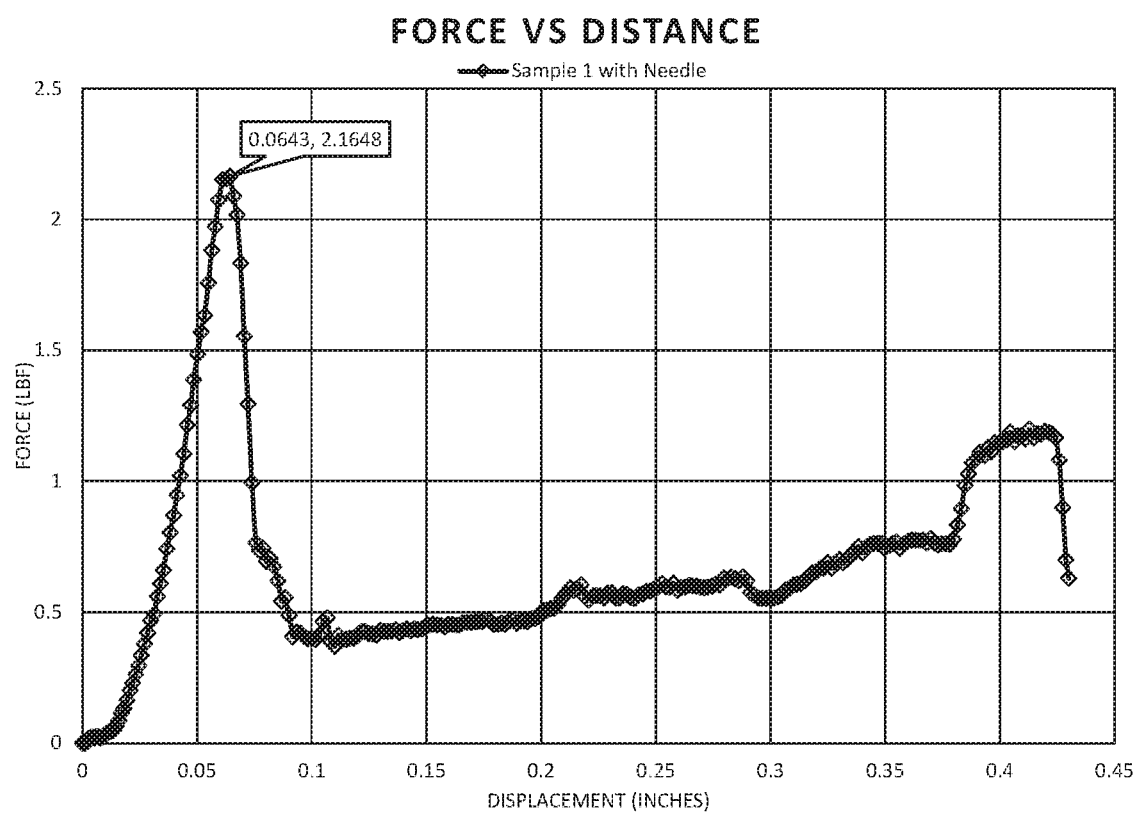
FIG. 24 is a graph showing force versus distance for sample 1 of FIG. 23.
Figure 25:
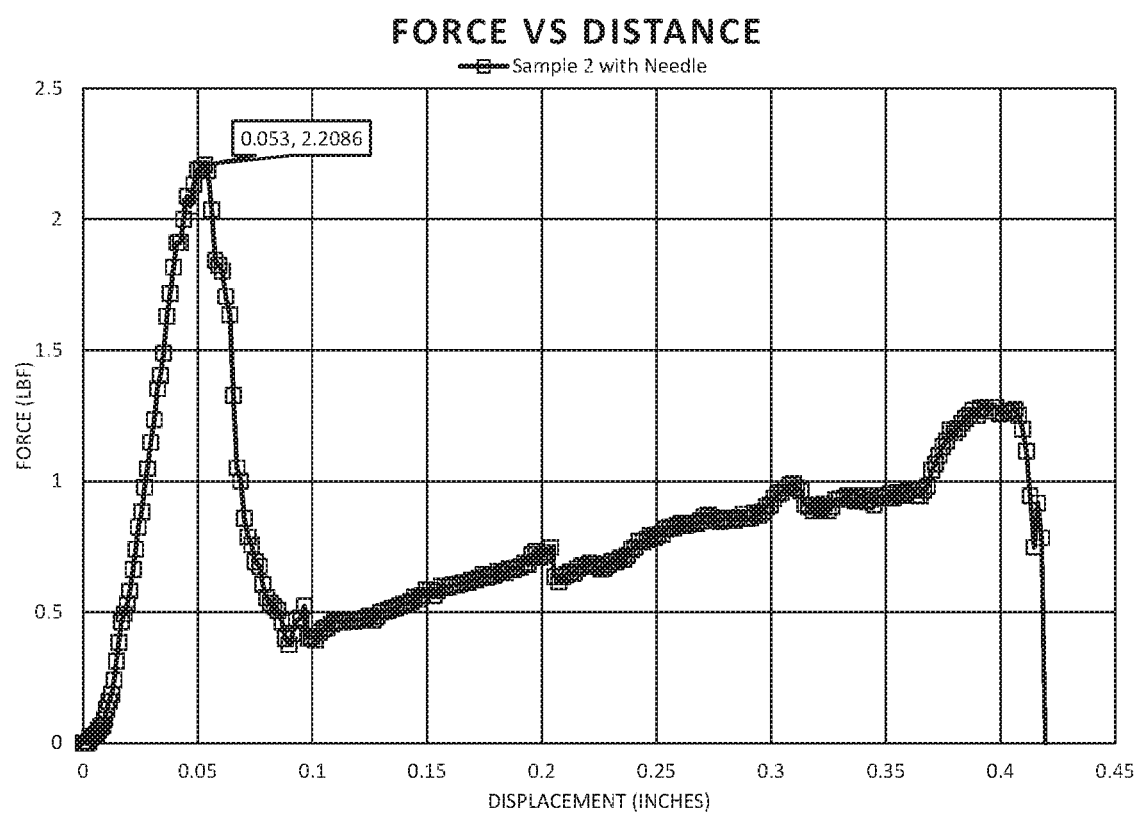
FIG. 25 is a graph showing force versus distance for sample 2 of FIG. 23.
Figure 26:
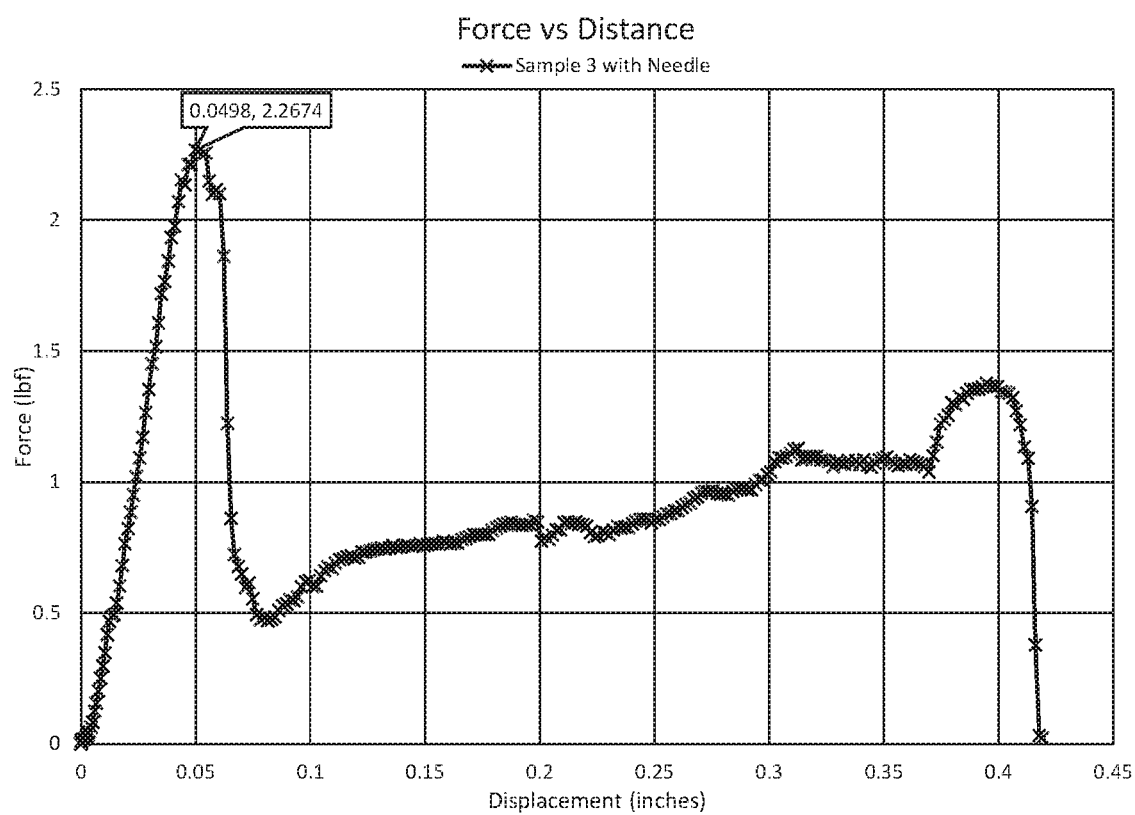
FIG. 26 is a graph showing force versus distance for sample 3 of FIG. 23.
Figure 27:
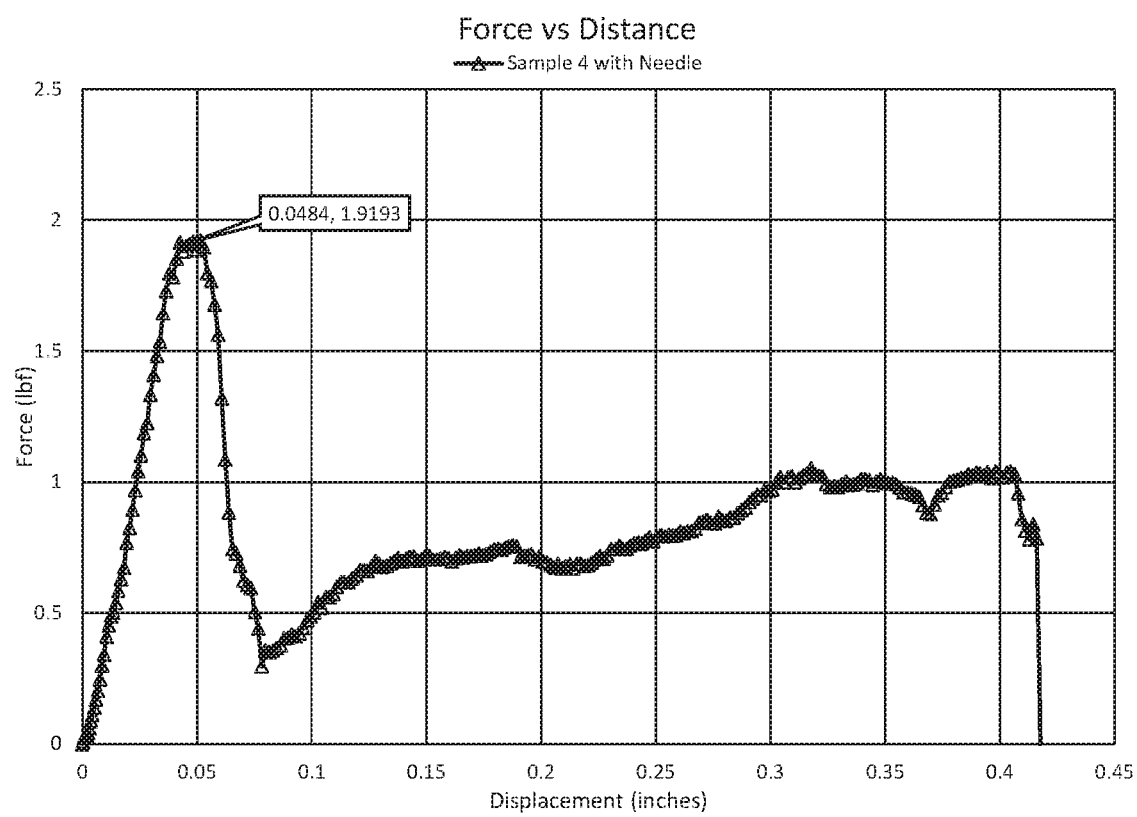
FIG. 27 is a graph showing force versus distance for sample 4 of FIG. 23.
Figure 28:
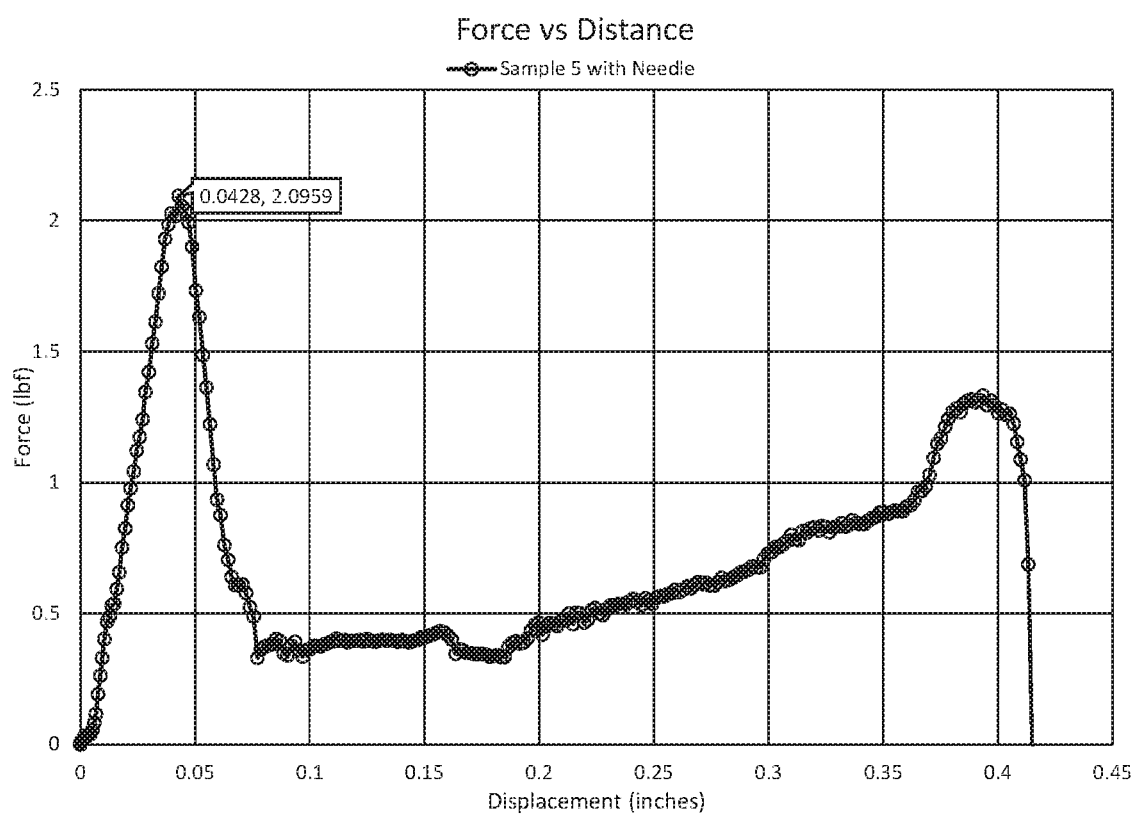
FIG. 28 is a graph showing force versus distance for sample 5 of FIG. 23.

Turning now to FIGS. 23-28, there is shown graphical illustrations of the force versus distance of inserter mechanism 200. FIG. 23 is a graph showing the force versus distance data for all five inserter mechanisms 200 used in the testing. As seen in FIG. 23, the deployment force required to cause deployment button 204 to release from first catch surface 210 and begin the slide along cam surface 211. As confirmed by the peak force data in Table 1 and the graphical illustration in FIG. 23, the actuation force to begin the actuation process is between 1.5 lbs. (680.4 g) and 2.5 lbs. (1.13 kg). The sharp drop in the amount of force down to about 0.5 lbs. (226.8 g) or less is a result of cam surface 211 having the sloping structure previously described. The peak force variation is due to the variation in the test fixture setup as well as reusing inserter components that are designed for one time use. Notwithstanding these variations, the standard deviation in the peak actuation force was only 0.133 lbf. (lbf meaning pounds of force). It should be noted that the time of the test can be calculated from the speed of the Mecmesin Force Tester. The distance is about 0.44 inches and the speed of the Force Tester is 10 inches per minute. The time to conduct the test is about 2.6 seconds. In use, however, the actual time lapsed between actuation, implantation of sensor 100 into the subcutaneous tissue and removal of a post-actuation inserter assembly 201' from the sensor housing 206 is considerably shorter. Post-actuation inserter assembly 201' contains deployment button 204, inserter housing 202, and needle assembly 208 while the sensor housing 206 remains on the patient's skin. The time period from actuation of the inserter assembly 202 to release of the post-actuation inserter assembly 201' is less than one second, and less than 0.5 seconds. It is typically in the range of less than 0.25 seconds to 0.8 seconds, or in the range of 0.25 seconds to 0.5 seconds, or in the range of 0.5 seconds to 0.8 seconds.

Figure 3:
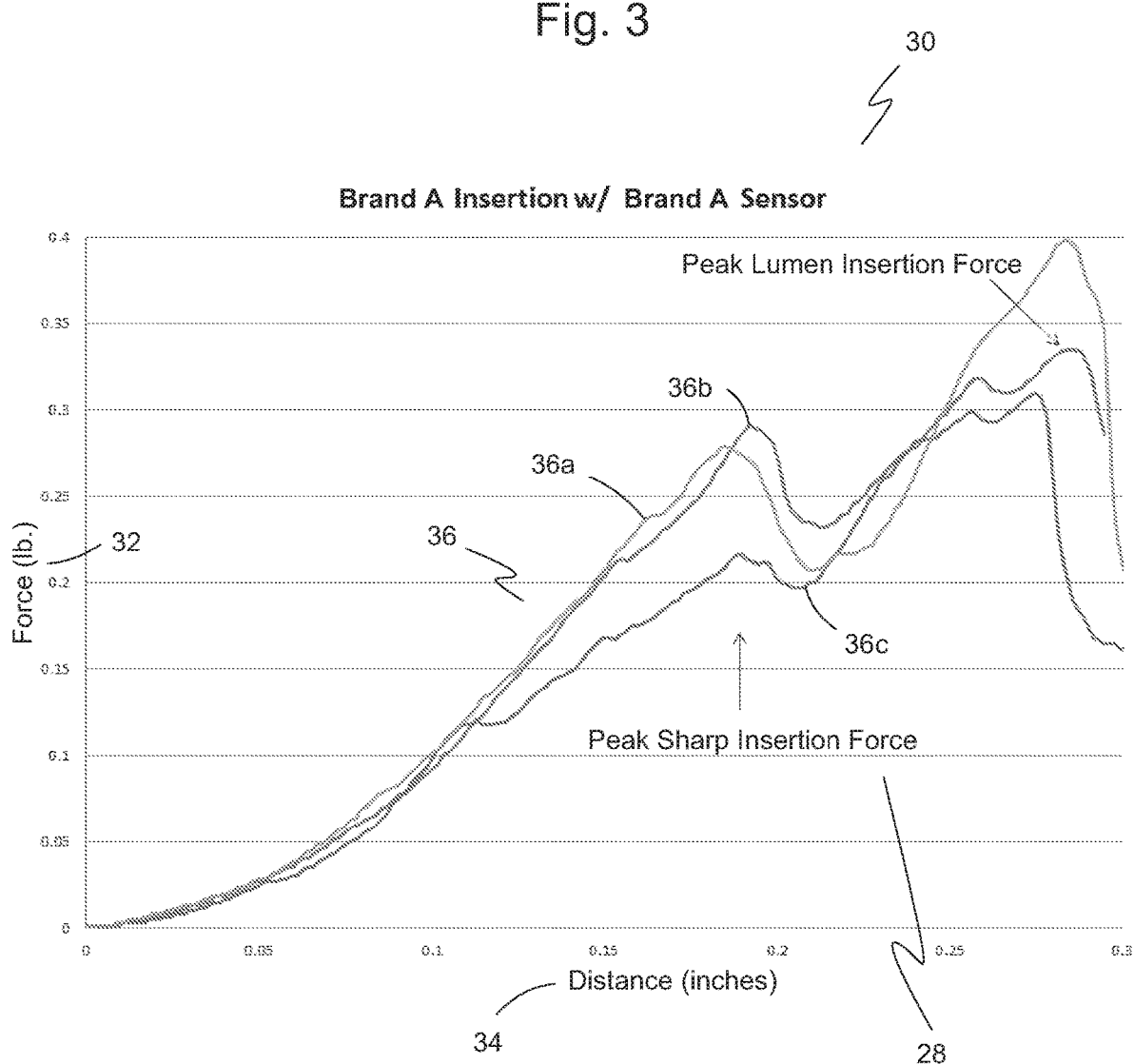
FIG. 3 is a graph showing data for one inserter set of the prior art, where insertion force is plotted against the distance of insertion and where the area under a curve is the work energy.

Turning now to FIGS. 24 to 28, there is shown in each figure a graphical illustration of the data for a single sample. As disclosed previously, the typical insertion depth of the sensor into the subcutaneous tissue during use is from 4 mm to 7 mm (±0.3 mm) for measurement of subcutaneous glucose but a range of 2 mm to 10 mm is also acceptable. This means that the sharp/needle must penetrate the subcutaneous tissue to a depth greater than the sensor insertion depth since the sensor is carried within the slotted needle 100 during sensor insertion. On average as the needle penetrates the synthetic skin sample, the force remains at a relatively low level (between 0.5 and 1 lbf) and begins to rise as the needle penetrates beyond 0.2 inches until furthest penetration is achieved (the applied force increases to less than 1.5 lbf). The small bump at approximately 0.4 inch distance represents the increase in force needed for the cam follower (i.e. resilient locking catch 214) to get past cam surface portion 211a and into second catch surface 210'. However as shown in each figure, the momentum that is built up by the sudden drop in force after the initial applied force of about 2 lbs. is reached (which is caused by the design of the cam follower deployment structure 209) minimizes any effect of the small rise in needle insertion force that occurs until furthest depth penetration is reached and needle 100 is released. Compare this to the constant rise in applied force shown in FIGS. 3 and 6.

An important feature of cam surface 211 is that, once the initial applied force is reached, the force to maintain deployment of button 204 greatly reduces, and the device is fully deployed before the patient can abort deployment such that partial deployment is not possible. This important safety feature ensures that a partially deployed system cannot happen and greatly simplifies the FMEA analysis (failure mode and effects analysis) as well as reduces the hazard and risk of the overall system. The hazard and risk includes, but are not limited to, re-deployment of the needle and sensor into the same insertion point, fouling of the sensor caused by blood forming in the subcutaneous wound as a result of partial deployment, damage to the sensor as a result of partial deployment, etc.

One of the advantages of using such a cam surface 211 with recess 118b and sloping recess surface 118c is that a deployment button spring is not needed to maintain deployment button in the ready-to-use position. Another advantage over the use of a deployment button spring is that the deployment button spring increases resistance against the downward movement of the deployment button due to the deployment button spring undergoing compression, which may cause improper insertion and/or partial insertion and then removal when the force used to depress deployment button 204 is inadequate or stopped short of the deployment button's end point. Another drawback is that such a failure allows re-deployment of deployment button 204 after a first attempted insertion. The cam surface 211, on the other hand, has the advantage of no spring biasing resistance increasing as deployment button 204 moves against the spring and the advantage of lessened resistance between resilient locking catch 214 of deployment button 204 and inserter housing wall 218 as deployment button 204 is depressed due to the decreasing wall thickness of housing wall 218 along cam surface 211 allowing relaxation of the biasing force imparted into locking catch 214. This ensures that deployment button 204 is pushed completely to the predefined depth where resilient locking catch 214 engages second catch surface 210'.

Figure 29:
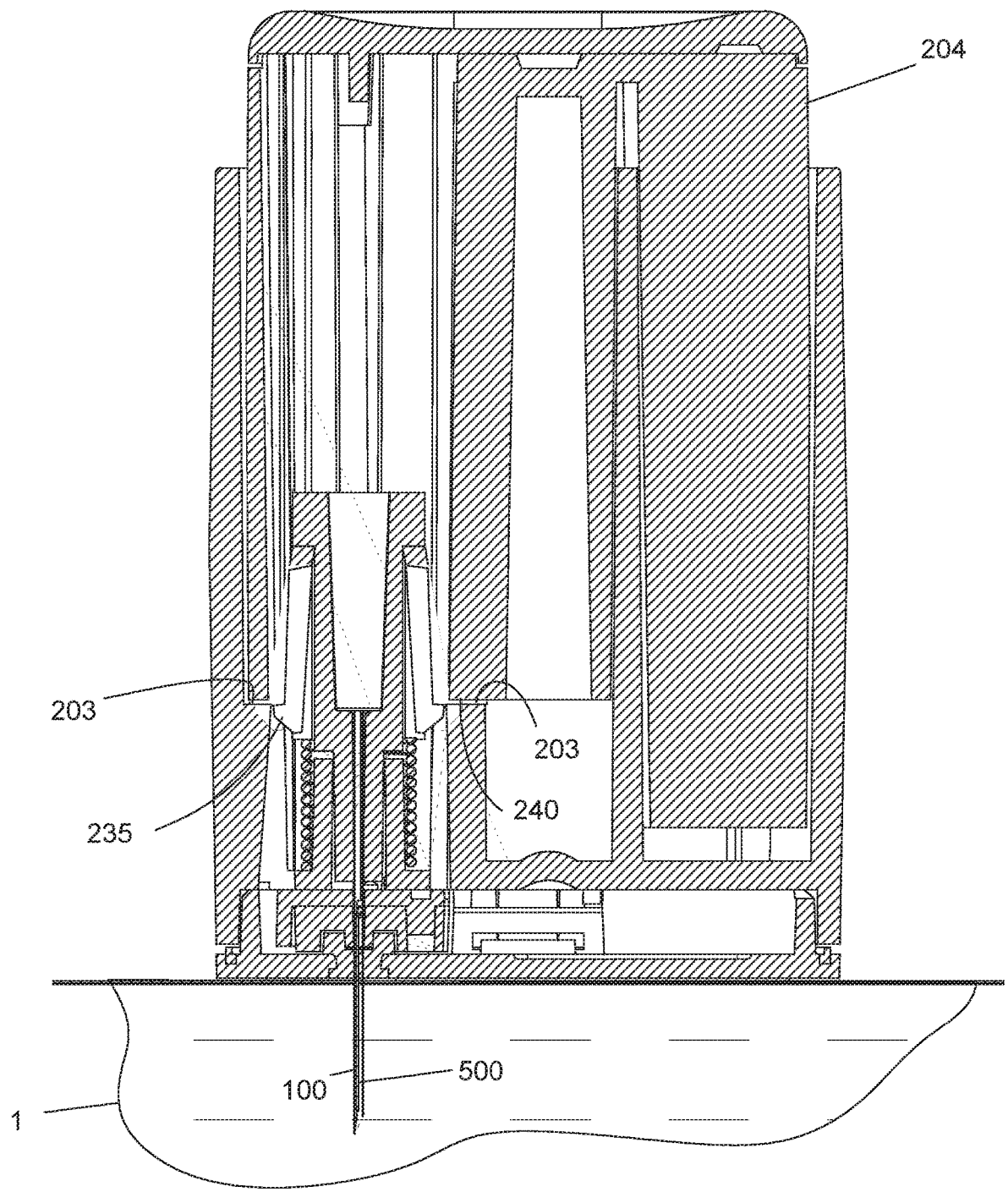
FIG. 29 is a cross-sectional side view of the inserter assembly showing the needle and sensor in an inserted position.

FIG. 29 is a cross-sectional side view of the inserter assembly 200 of FIG. 19 in a fully-inserted position. At this point during the insertion process, needle 100 and sensor 500 penetrate the subcutaneous tissue 1. Deployment button 204 contacts one or more inserter housing stop surfaces 203. A portion of housing stop surfaces 203 also interact with needle carrier catch 235 by pushing needle carrier catch 235 inwardly toward needle 100 and releasing needle carrier catch 235 away from button catch surface 240.

Figure 30:
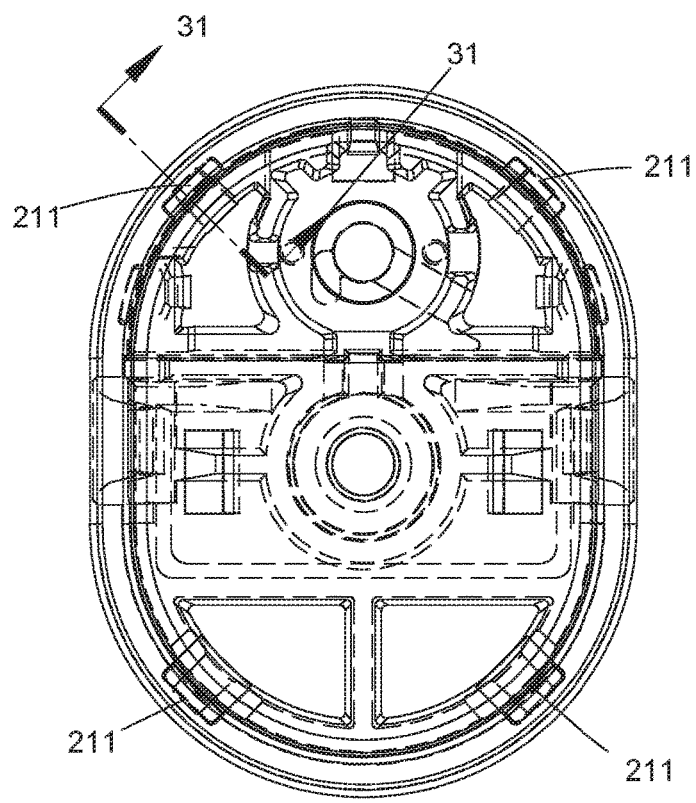
FIG. 30 is a top view of a deployment button within an inserter housing showing a view line 31-31 through one of the cam surfaces of FIG. 30.
Figure 31:
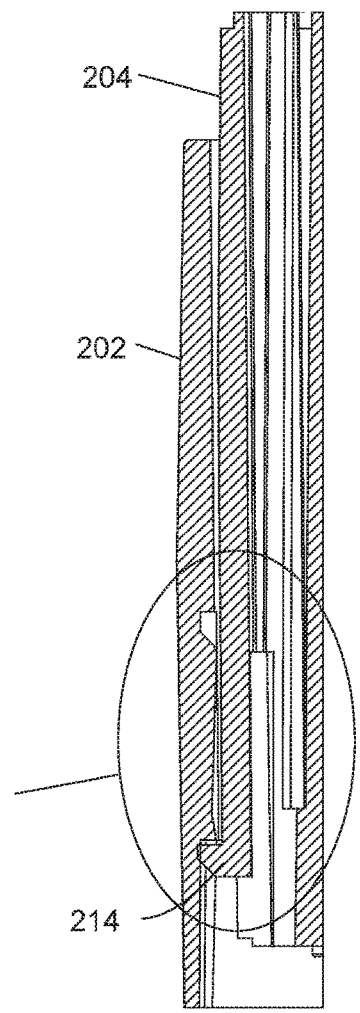
FIG. 31 is a cross-sectional view of the deployment button and the inserter housing taken alone the view line 31-31 in FIG. 30.
Figure 32:
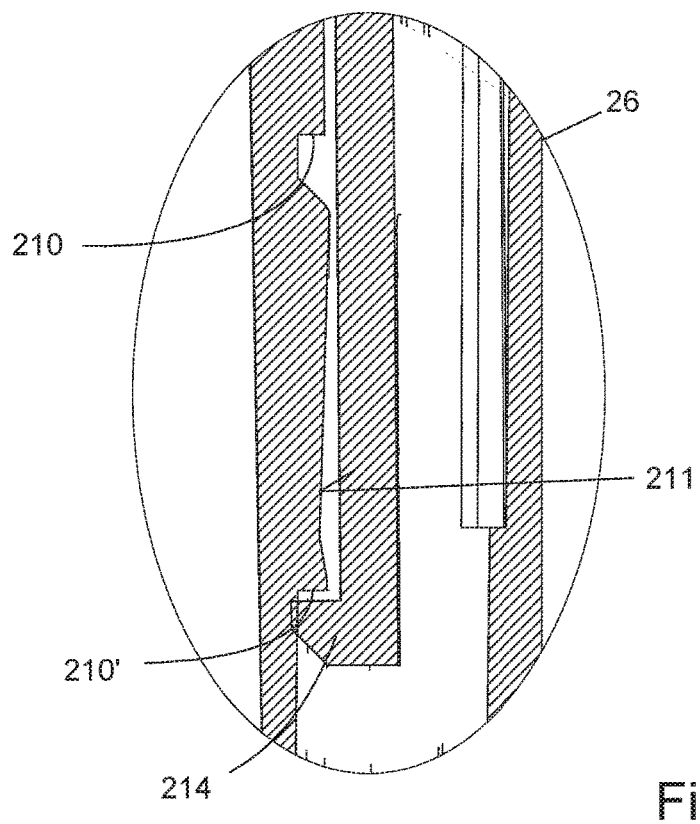
FIG. 32 is an enlarge view of the cam surface and deployment button retaining member outlined in FIG. 31.

FIG. 30 is a top view of inserter housing assembly 222 with a view line 25-25 taken longitudinally through cam surface 211. FIG. 31 is a cross-sectional view of inserter housing assembly 222 taken along view line 32-32 in FIG. 30. This cross-sectional view shows the contour of cam surface 211 with resilient locking catch 214 holding deployment button 204 in an inserted position. FIG. 32 is an enlarged view of the corresponding area outlined by reference ellipse 26 in FIG. 31.

As seen in FIG. 32, resilient locking catch 214 is now captured by second catch surface 210', which prevents re-use and re-deployment of deployment button 204. When resilient locking catch 214 reaches the recess of second catch surface 210', locking catch 214 is forced to align with first catch surface 210'.

Figure 33:
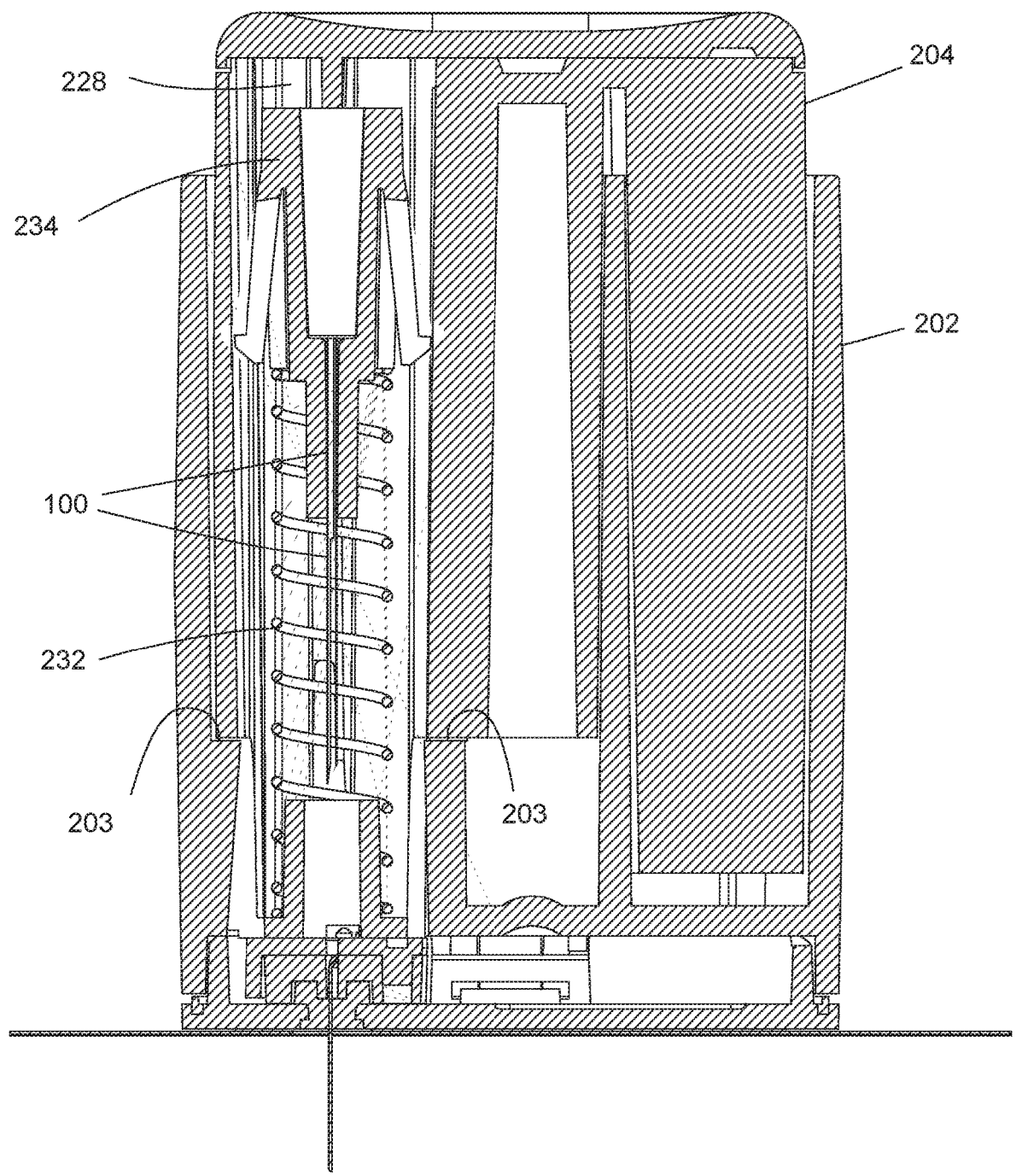
FIG. 33 is a cross-sectional side view of an inserter assembly showing the needle assembly retracted back into the deployment button.

Turning now to FIGS. 33-36, the action of inserter assembly 200 will be explained. Once deployment button 204 is pressed and needle 100 and sensor 500 are inserted into the subcutaneous tissue, FIG. 33 shows that when deployment button 204 contacts one or more inserter housing stop surfaces 203 and carrier catch 235 is released from needle carrier catch 235, deployment spring 232 is no longer confined to its compression state thereby allowing deployment spring 232 to expand causing needle carrier 234 with needle 100 to retract from the subcutaneous tissue and recede up into deployment mechanism cavity 228. Substantially simultaneously with the release of carrier catch 235, deployment button catch 214 slides into second catch surface 210' locking deployment button 204 in the inserted position.

It is noted that the term "substantially simultaneously" means that the actions disclosed during sensor insertion into the subcutaneous tissue are happening so quickly and close together in time that the different actions are not perceived by the human senses to occur other with a single action or a plurality of simultaneous events.

Figure 34:
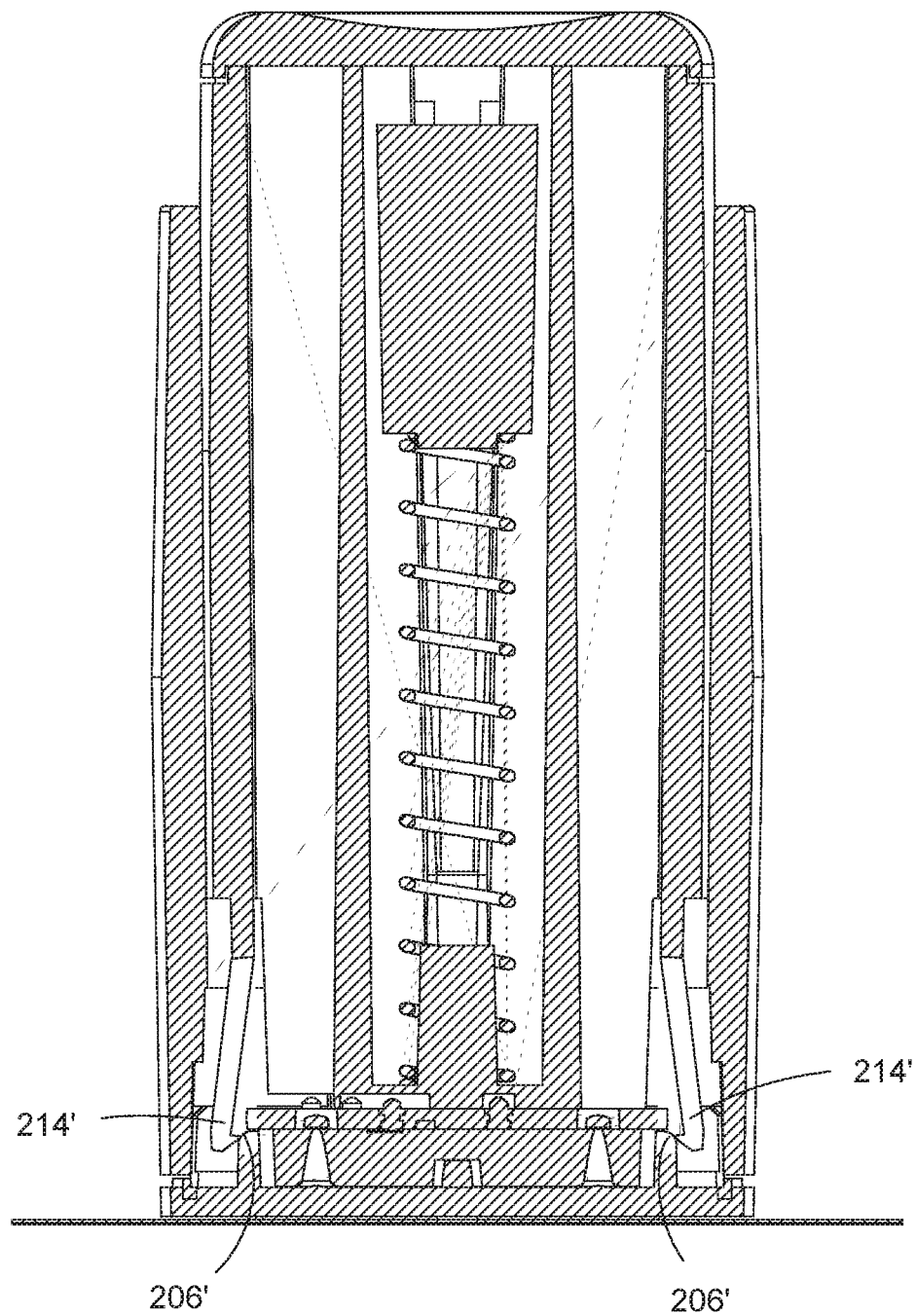
FIG. 34 is a cross-sectional front view of the inserter assembly showing the sensor deployment assembly retaining member in a released position.

While the above actions are occurring, sensor deployment assembly 236 is substantially simultaneously being released from sensor deployment assembly catch 214'. FIG. 34 is a cross-sectional view of the inserter assembly 200 through sensor deployment assembly catch 214'. As deployment button 204 bottoms out at inserter housing stop surfaces 203, sensor deployment assembly catch 214' interacts with sensor assembly catch release surface 206' forcing assembly catch 214' away from sensor deployment assembly 236.

Figure 35:
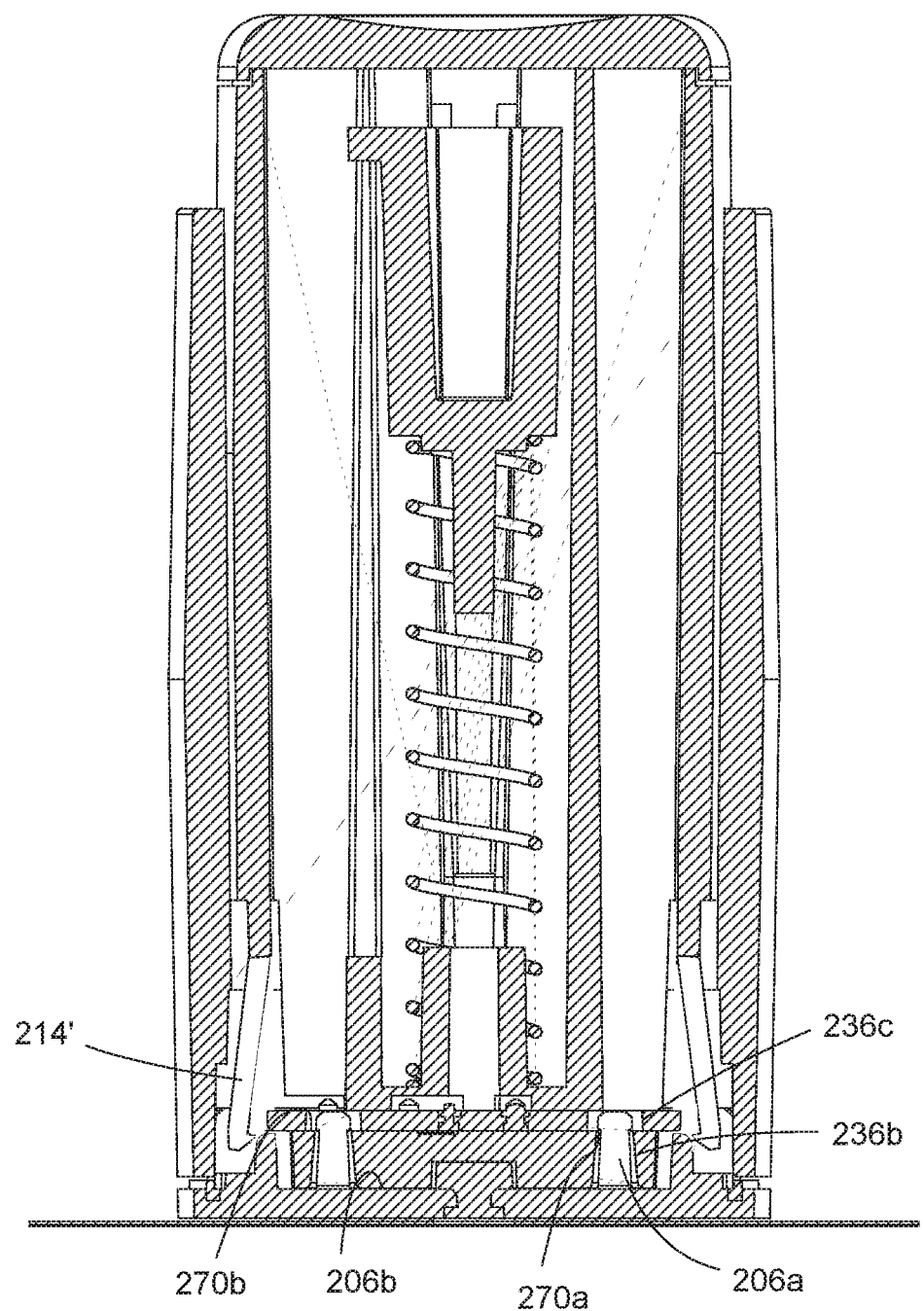
FIG. 35 is a cross-sectional front view of the inserter assembly showing a sensor housing retaining member having captured the sensor deployment assembly within the sensor housing.

FIG. 35 shows the substantially simultaneous capture of sensor deployment assembly 236 within sensor housing 206. Lower deployment body 270 and upper deployment body 236a have at least one aligned through opening 236b. Through opening 236b has a through opening portion 236c in upper deployment body 236 and a through opening portion 270a in lower deployment body 270 such that a deployment body catch surface 270b is formed within through opening 236b. Sensor housing 206 has at least one sensor deployment assembly catch 206a that extends from an inside bottom surface 206b and is positioned to align with through opening 236b. Sensor deployment assembly catch 206a captures and retains sensor deployment assembly 236 within sensor housing 206 substantially simultaneously with the release of assembly catch 214'.

Figure 36:
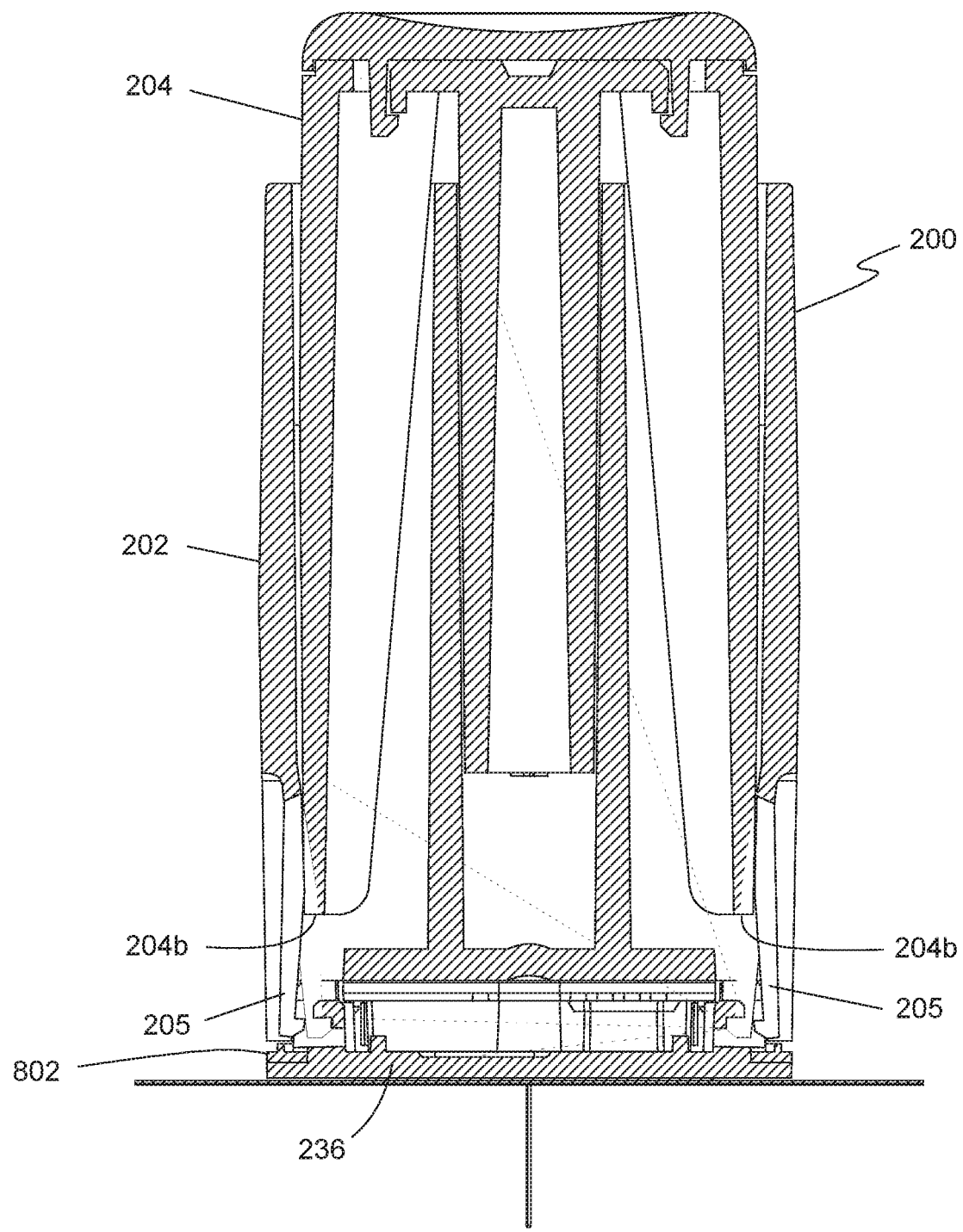
FIG. 36 is a cross-sectional front view of the inserter assembly showing the inserter housing retaining members in a released position with the sensor housing caused by the deployment button.

While all the previously disclosed capture and release actions are occurring, FIG. 36 shows the substantially simultaneous release of sensor housing 206 from inserter assembly 200. As deployment button 204 is bottoming out, second button end 204b is engaging housing locking mechanism 205. Prior to this release action, recall that housing locking mechanism 205 has locking mechanism end catch 205a that is hooked onto sensor housing catch surface 206a and retains sensor housing 206 against second housing end 215 of inserter housing 202. Second button end 204b pushes/biases housing locking mechanism away from sensor housing catch surface 206a releasing the inserter housing 202 from sensor housing 206.

Through the substantially simultaneous catch and release actions of inserter assembly 200, a needle 100 implants sensor 500 subcutaneously, retracts out of the subcutaneous tissue into deployment button 204, sensor deployment assembly 236 is released from deployment button 204 and captured within sensor housing 206, and inserter housing 202 with deployment button 204 is released from sensor housing 206 leaving sensor housing 206 with sensor 500 deployed subcutaneously.

Figure 37:
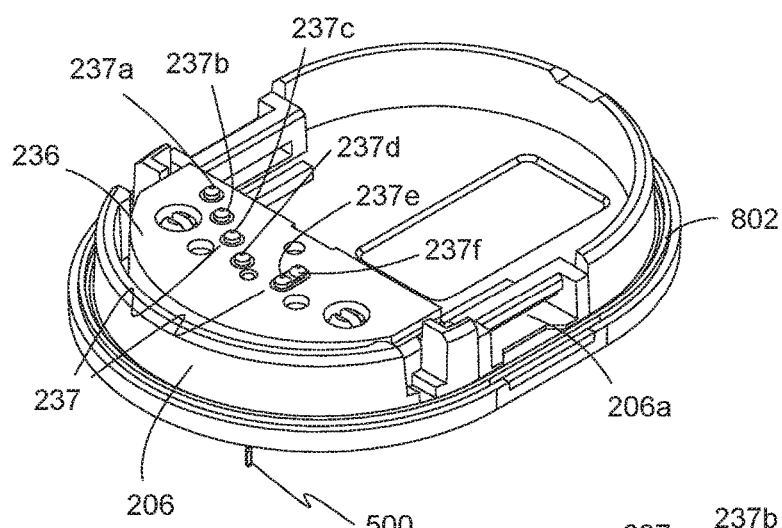
FIG. 37 is a perspective top view of the sensor housing with the sensor deployment assembly captured in the sensor housing after release of the inserter housing.
Figure 38:
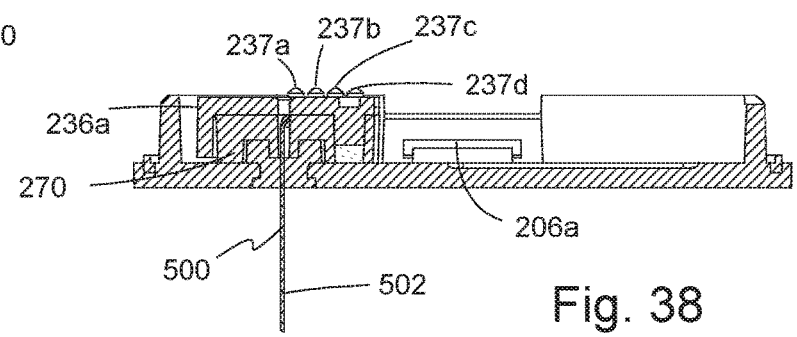
FIG. 38 is a cross-sectional side view of the sensor housing of FIG. 37.

FIG. 37 illustrates an enlarged view of sensor housing 206 with sensor deployment assembly 236 captured within sensor housing 206. For clarity, the subcutaneous tissue is not shown. Sensor deployment assembly has a plurality of resilient electrical coupling members 237. Electrical coupling members 237a-d couple to the various electrodes of sensor 500. Electrical coupling members 237e-f is a continuity switch that completes the electrical circuit between a battery 706 and module circuit board 702 in the sensor housing cover assembly 850. FIG. 38 is a cross-sectional view of the sensor housing of FIG. 37 with distal portion 502 of sensor 120 extending through sensor housing grommet 251 and a proximal portion 501 of sensor 120 captured between lower deployment body 270 and upper deployment body 236a.

Figure 39:
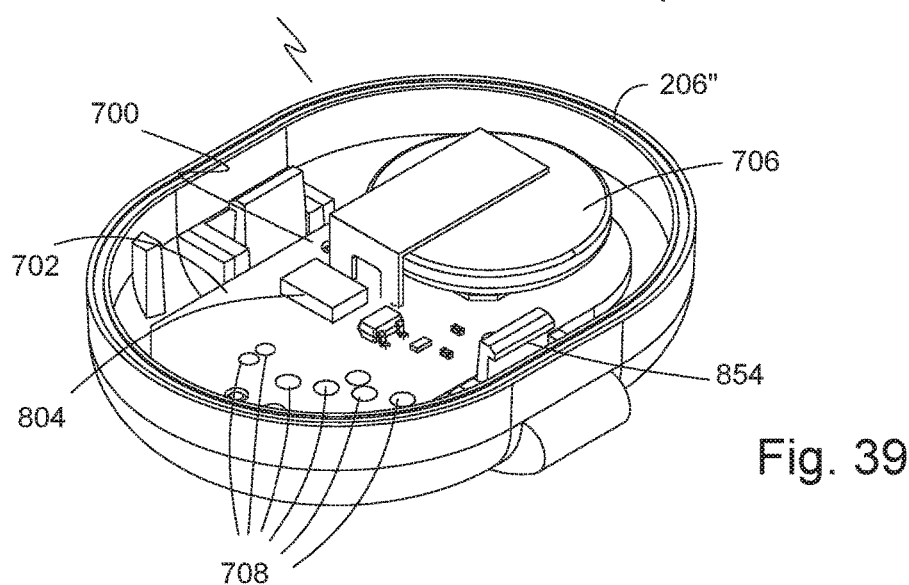
FIG. 39 is a perspective bottom view of one embodiment of a sensor housing cover showing the electronic module and battery attached to the inside of the sensor housing cover.

FIG. 39 is an enlarged, bottom, perspective view of one embodiment of sensor housing cover assembly 850. As shown, cover assembly 850 contains electronic module 700. Electronic module 700 includes module circuit board 702 and battery 706. Module circuit board 702 has a plurality of electrical connectors 708 that electrically couple the measurement circuit to the respective electrical coupling members 237a-f of sensor deployment assembly 236. Sensor housing cover 850 captures assembly gasket 802 between the perimeter of cover 850 and the perimeter 206" of sensor housing 206 by the interlocking of resilient cover locking tab 854 with sensor housing catch surface 206a. In this embodiment, there are two cover locking tabs 854, one on each side of cover 850. In other embodiments, cover 850 may have only one releasable locking tab 854 while the opposite side has only a fixed locking tab that engages a housing catch surface by way of a hinge type action where the fixed locking tab is hooked to the housing catch surface first followed by the releasable locking tab 854 engaging sensor housing catch surface 206a.

Figure 40:
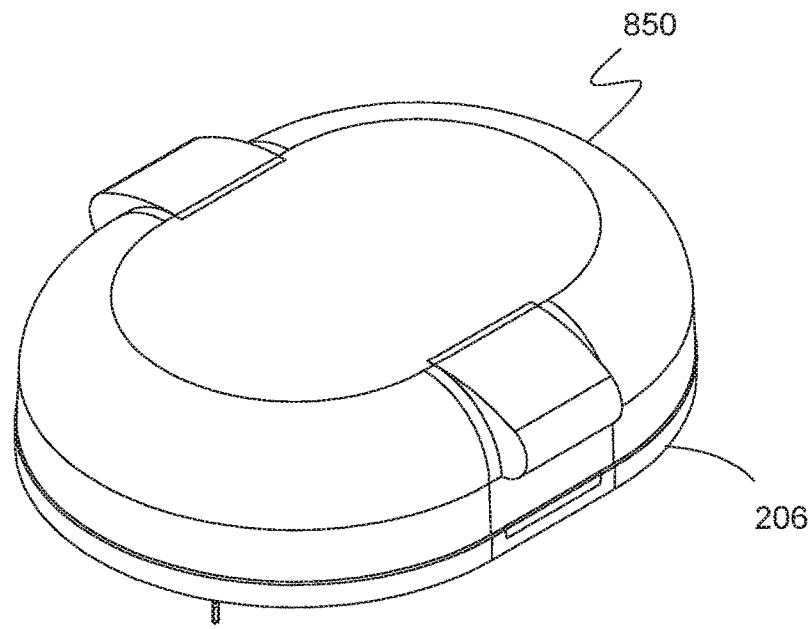
FIG. 40 is a perspective top view of the sensor housing cover in FIG. 37 connected to the sensor housing after deployment of the sensor forming the CGM assembly.
Figure 41:
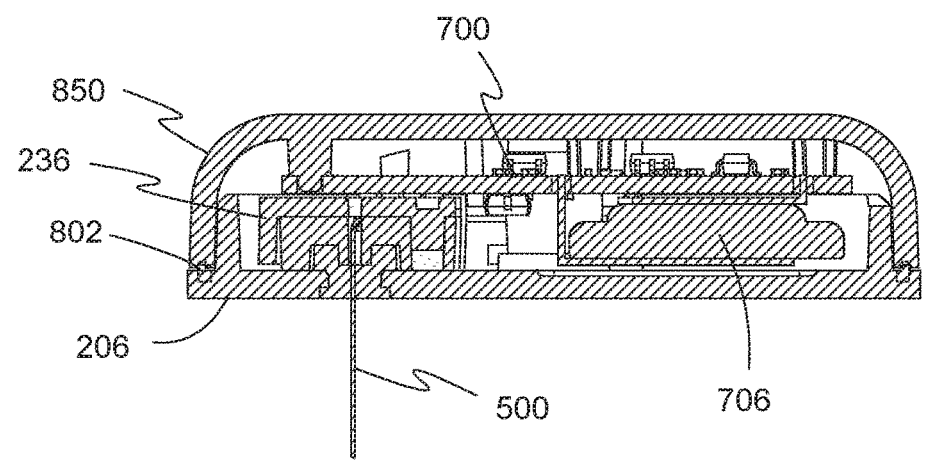
FIG. 41 is a cross-sectional side view of the CGM assembly of FIG. 40.

FIG. 40 show sensor housing cover 850 mated to sensor housing 206. FIG. 41 is a cross-sectional view of sensor housing cover 850 and sensor housing 206 in FIG. 40 showing battery 706 and electronic module 700 and their location relative to their position with sensor housing 206 and sensor deployment assembly 236.

There are several advantages of the various embodiments of the present invention. One aspect of the present invention provides an advantage for a nearly pain-free insertion of the sensor subcutaneously into the skin of a patient. Another aspect of the present invention provides the advantage of a single action that implants the sensor 120, retracts the needle/sharp 100, and releases the inserter assembly 200 leaving the sensor housing 206 with the sensor 120 implanted where the sensor housing is ready for receiving the electronic module 700. In yet another aspect of the present invention, another advantage is the inserter assembly design incorporates a further useful feature, which is the safe retraction of the sharp for safe disposal. A sharp is defined by the FDA (the US Food and Drug Administration) as a device with sharp edges that can puncture or cut skin, and includes devices such as needles, syringes, infusion sets and lancets. Improper disposal or handling of sharps can cause accidental needle stick injuries including transmission of Hepatitis B (HBV), Hepatitis C (HBC) and Human Immunodeficiency Virus (HIV). Used sharps must be placed in a "sharps" container such as the BD™ Home Sharps Container, and fully sealed, before checking with local laws on proper disposal. As previously disclosed, the structural feature of cam surface 211 along with first and second catch surfaces 210, 210' prevents partial deployment of button 204 and the risk that partial deployment creates.

FIGS. 9, 19 and 33 show the sharp fully enclosed within inserter assembly 200. The sharp is fully covered and is not accessible by finger. By design, the device cannot be made to re-deploy the sharp. No special "sharps" container is required to store and dispose of the inserter housing after sensor deployment. The entire body can be disposed of according to local laws.

Figure 42:
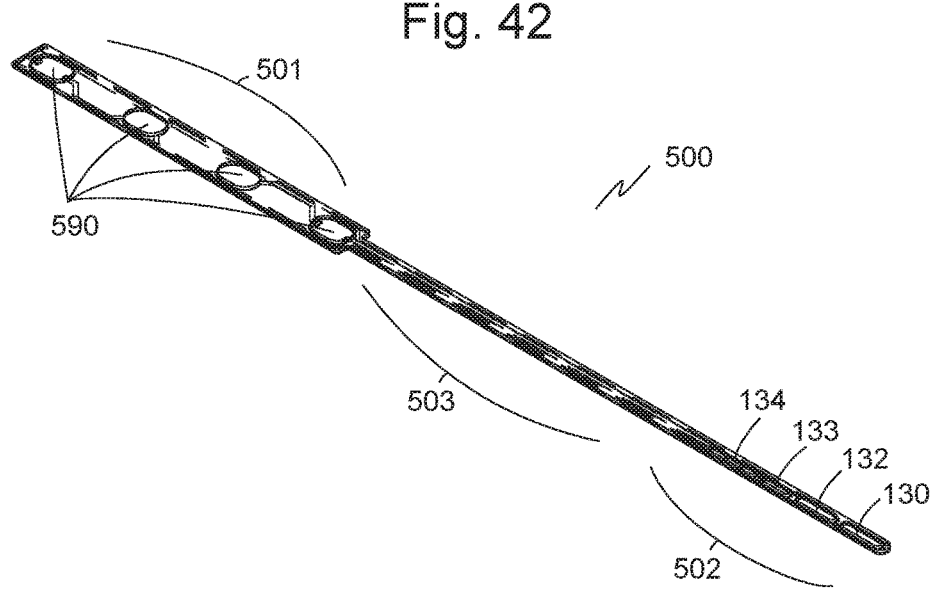
FIG. 42 is a perspective view of one embodiment of a multi-layer sensor of the present invention.

Sensor Construction:

Construction of the novel, multi-layer sensor substrate 500 will not be described. FIG. 42 shows a perspective illustration of one embodiment of a multi-layer sensor assembly 500 ready for deposition of reagents to create a continuous monitoring sensor 120 having, in this embodiment, a reference electrode 134, a blank or second working electrode 133, a counter electrode 132, and a first working electrode 130. Electrodes 130, 132, 133, 134 are formed at a substrate distal end portion 502 and communicate electrically through assembly middle portion 530 with electrically-conductive contact pads 503 at a substrate proximal end portion 501. Multi-layer sensor substrate 500 is useful to form a subcutaneous analyte sensor, such as a glucose monitoring sensor.

A sensing layer (not shown) is formed over each of the first and second working electrodes 130, 133. The sensing layer is made up of three coating layers, a base coating layer, a second coating layer and a third or top coating layer. The base coating layer contains poly-2-hydroxyethyl methacrylate (PHEMA) and is the coating that is disposed directly on the exposed metal at the bottom of the respective wells at substrate distal end portion 502. Specific to the first working electrode where glucose is measured, glucose oxidase and/or glucose dehydrogenase is also included. The second working or blank electrode does not contain any enzyme and is used only for measuring background noise and/or interferents in the sample since the first working electrode will have a total current that include a portion driven by the amount of glucose in the subcutaneous tissue as well as the background noise and/or interefents derived current. Using an algorithm to subtract the current derived from the second working or blank electrode from the first working electrode provides a more accurate glucose measurement. The second coating layer is disposed directly on the base coating layer and contains PHEMA and a plurality of microspheres from polydimethylsiloxane (PDMS). PDMS is a material a material having substantially no or little permeability to glucose but a substantially high permeability to oxygen. The third or top coating layer is disposed directly on the second coating layer and contains PHEMA and catalase. Catalase is a material that prevents release of hydrogen peroxide from the sensing layer into the surrounding environment. In this case, the surrounding subcutaneous tissue.

For the reference electrode 134, a silver-silver chloride (AgCl) layer is created on the metal at the bottom of the well and then the AgCl layer is covered with a hydrogel membrane. The counter electrode 132 has the metal at the bottom of the well covered only with a hydrogel membrane.

Figure 43:
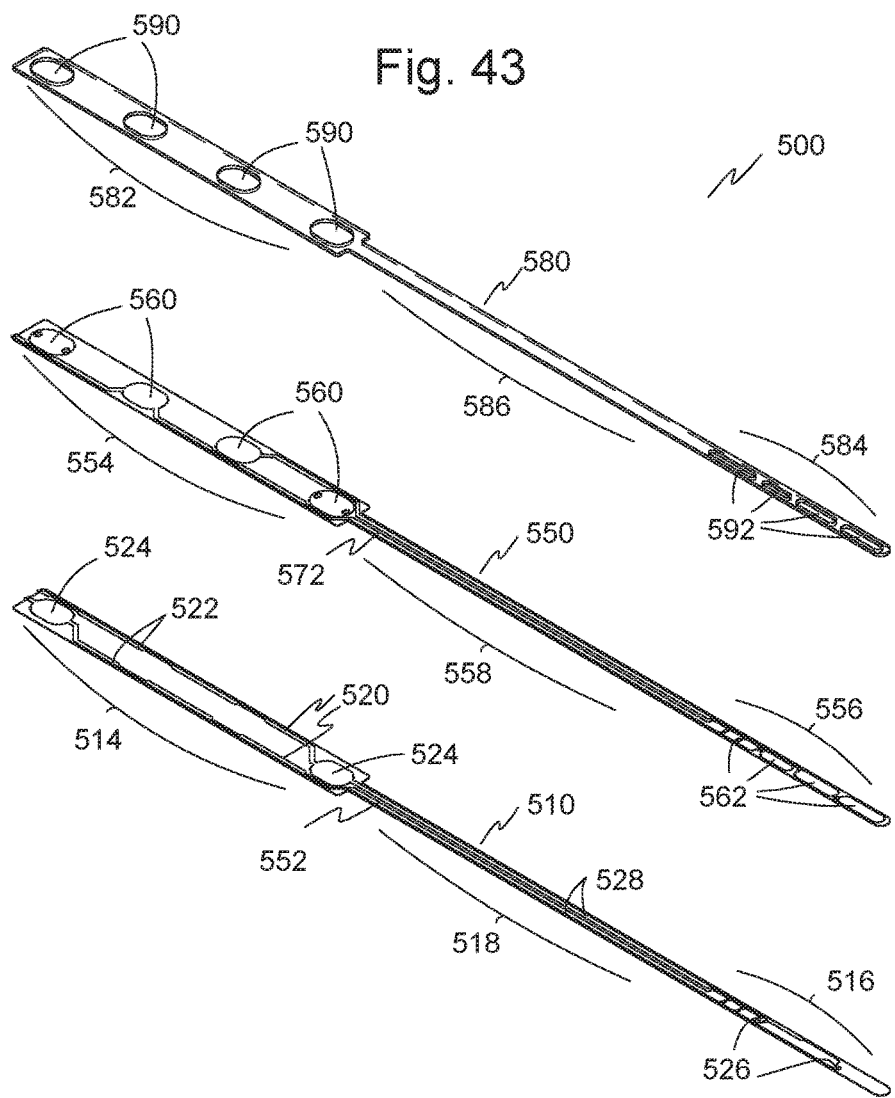
FIG. 43 is an exploded perspective view of the multi-layer sensor of FIG. 42.

Referring now to FIG. 43, a perspective, exploded illustration shows a base layer 510, a middle layer 550, and a top layer 580 that together comprise multi-layer sensor substrate 500. "Middle layer" herein means the layer adjacent to the top layer 580 without any intervening, electrically-insulating layer when there are other layers between base layer 510 and middle layer 550. Base layer 510 is electrically insulating and includes a base proximal end portion 514, a base distal end portion 516, and a base middle portion 518 between base proximal end portion 514 and base distal end portion 516. A base metallized layer 520 is disposed on base layer 510 and defines at least one circuit 522 extending longitudinally along base layer 510. Each circuit 522 has an electrically-conductive contact pad 524 formed at base proximal end portion and an electrically-conductive contact pad 526 formed at base distal end portion 516 with an electrically-conductive trace 528 electrically coupling electrically-conductive contact pad 524 at the base proximal end 514 with electrically-conductive pad 526 at base distal end 516.

Middle layer 550, also electrically insulating, is disposed over base layer 510 and includes a middle layer proximal end portion 554, a middle layer distal end portion 556, and a middle layer middle portion 558. Middle layer 550 has a size and shape corresponding to base layer 510 and that is aligned with base layer 510. Middle layer 550 includes electrically-conductive contact pads 562 at middle layer distal end portion 556 adapted to receive an electrode material or reagent to form a respective electrode. Each electrically-conductive contact pad 560 at middle layer proximal end portion 554 is adapted to receive an electrical contact.

The top layer 580, also electrically-insulating, is disposed over middle layer 550. Top layer 580 has a size and shape corresponding to middle layer 550 and base layer 510. Top layer 580 has a top layer proximal end portion 582, a top layer distal end portion 584, and a top layer middle portion 586, where top layer 580 aligned with base layer 510 and middle layer 550. Top layer 580 has a plurality of openings that include contact openings 590 on substrate proximal end portion 501 (See FIG. 42) and sensor wells 592 on substrate distal end portion 502 (See FIG. 42). Contact openings 590 and sensor wells 592 coincide with electrically-conductive contact pads 560, 562, respectively, of middle layer 550. Base layer 510, middle layer 550, and top layer 580 are manufactured with circuits 552, 572 on base layer 510 and middle layer 550, respectively, to create multi-layer sensor substrate 500 with substrate proximal end portion 501, substrate distal end portion 502, and assembly middle portion 503 extending longitudinally between substrate proximal end portion 501 and substrate distal end portion 502 as shown, for example, in FIG. 42. Substrate distal end portion 502 and assembly middle portion 503 each have a width of about 279 microns.

Referring now to FIGS. 44-46, base layer 510 is shown in a plan view in FIG. 44, base proximal end portion 514 is shown enlarged in FIG. 45, and base distal end portion 516 is shown enlarged in FIG. 46. Base layer 510 has a base layer substrate 512 that is electrically insulating and includes a base proximal end portion 514, a base distal end portion 516, and a base middle portion 518 extending between and connecting base proximal end portion 514 and base distal end portion 516. In one embodiment, base layer substrate 512 is made of polyimide and has a thickness from 7.5 μm to 12.5 μm. For example, base layer substrate 512 has a thickness of about 10 μm. In one embodiment discussed in more detail below, base layer substrate 512 may be formed by spin coating polyimide on a glass plate followed by further lithographic processing.

Base metallized layer 520 is disposed directly onto base layer substrate 512 and defines at least one circuit extending longitudinally along base layer substrate 512 from base layer proximal end portion 514 to base layer distal end portion 516. In one embodiment as shown, base metallized layer 520 defines two circuits 522, where each circuit 522a, 522b has an electrically-conductive contact pad 524a, 524b, respectively, formed at base proximal end portion 514. Circuit 522a has electrically-conductive contact pads 526a1-526a2, formed at base distal end portion 516. Circuit 522b has electrically-conductive contact pad 526b at distal end portion 516. Each circuit 522a, 522b has an electrically-conductive trace 528a, 528b electrically coupling electrically-conductive contact pads 524a, 524b at the base proximal end portion 514 with the respective electrically-conductive pads 526a1-526a2 and 526b at the base distal end portion 516. For example, circuit 522a is configured for a working electrode 130 of sensor assembly 120 and circuit 522b is configured for a blank electrode 133 of sensor assembly 120 (shown in FIG. 42).

Comparing distal end portions 516 and 556 of FIGS. 46 and 49, respectively, contact pads 526a1-526a2 of metallized layer 520 each have a size and shape corresponding to one or more contact pads 562 of middle metallized layer 550, rather than being sized only for through openings 564 of middle layer substrate 552. An advantage of this configuration is that contact pads 526a1-526a2 reduce stress induced to contact pads 562 caused by the spin coating process described below, which stress leads to cracking of contact pads 562 in middle metallized layer 570. In one embodiment, for example, contact pad 526a1 is sized and shaped to substantially underlie contact pad 562a of middle metallized layer 570, but not through opening 564c. Contact pad 526a2 is sized and shaped to substantially underlie contact pads 562b, 562c and through opening 564d of middle metallized layer 570.

In one embodiment, base metallized layer 520 has an overall thickness of 1200±300 Å. For example, base metallized layer 520 is formed by depositing a first part of chromium (200±150 Å) directly onto and against base layer substrate 512, a second part of gold (1000±150 Å) disposed directly onto the chromium, and a third part of chromium (200±150 Å) disposed directly onto the gold. In other words, the base metallized layer 520 has a thickness in the range of about 900 Angstroms to about 1,500 Angstroms. Other conductive materials and thicknesses are acceptable for base metallized layer 520 depending on the intended use of sensor assembly 120.

Referring now to FIGS. 47-49, middle layer 550 is shown in a plan view in FIG. 47, second proximal end portion 554 is shown enlarged in FIG. 48, and second distal end portion 556 is shown enlarged in FIG. 49. Middle layer 550 has a middle layer substrate 552 that is electrically insulating and defines a plurality of middle layer through openings 564 with side walls extending to base layer 510, where each middle layer through opening 564 communicates electrically with a respective electrically-conductive contact pad 524, 526 of circuit 522 of base layer 510. In one embodiment, middle layer substrate 552 is made of polyimide that is spin coated onto base layer 510 and base metallized layer 520 as discussed below, for example, in a method 600 of making multi-layer sensor substrate 500. In one embodiment, middle layer substrate 552 has a thickness from 7.5 μm to 12.5 μm, such as about 10 μm.

A middle metallized layer 570 is disposed directly onto middle layer substrate 552 and the side walls of through openings 564 to define at least two middle layer circuits 572, where each middle layer circuit 572 has electrically-conductive contact pad 560 formed at middle layer proximal end portion 554 and electrically-conductive contact pad 562 formed at middle layer distal end portion 556 with an electrically-conductive trace 574 electrically coupling contact pad 560 at middle layer proximal end portion 554 with electrically-conductive contact pad 562 at middle layer distal end portion 556, and a least one or more additional electrically conductive pads 560, 562 in electrical contact with through openings 564. The at least one or more additional electrically conductive pads 560, 562 electrically coupled to base layer circuit(s) 522 by way of through openings or vias 564. For example, middle metallized layer 570 is deposited on top surface 550a, on the sidewalls of through openings 564, and onto part of base metallized layer 520 creating electrical continuity between the base metallized layer 520 and the respective contact pads 560, 562.

In one embodiment of middle layer proximal end portion 554 as shown in FIG. 48, for example, middle layer circuit 572a includes contact pad 560b and middle layer circuit 572b includes contact pad 560c. Contact pads 560a, 560d are isolated from middle layer circuits 572a, 572b. Contact pad 560a (which is electrically coupled to working electrode 130 at the middle layer distal end 556) defines two through openings 564a and contact pad 560d (e.g., for blank electrode 133) defines two through openings 564b, each of which has electrical continuity to base metallized layer 520 at contact pad 524a and contact pad 524b, respectively (shown in FIG. 45).

In one embodiment of middle layer distal end portion 556 as shown in FIG. 49, for example, middle layer circuit 572a includes contact pad 562a and middle layer circuit 572b includes contact pad 562c. Contact pads 562b, 562d are isolated from middle layer circuits 572a, 572b. Middle layer substrate 552 has through opening 564c at with contact pad 562b (e.g., for blank electrode 133) having electrical continuity to base metallized layer 520 at contact pad 526b (shown in FIG. 46). Middle layer substrate 552 defines through opening 564d with contact pad 562d having electrical continuity with contact pad 526a2 (shown in FIG. 46). Contact pads 562d and 562b are isolated from middle layer circuits 572a, 572b. Contact pad 562a (i.e. the reference electrode 134) is segmented into 3 contact pad portions 562a1, 562a2 and 562a3. The reference electrode 134 is segmented to prevent cracking of the Ag/AgCl and delamination from contact pad 562a, which is a definite advantage where sensor 500 is implanted subcutaneously in a patient.

Figure 50:
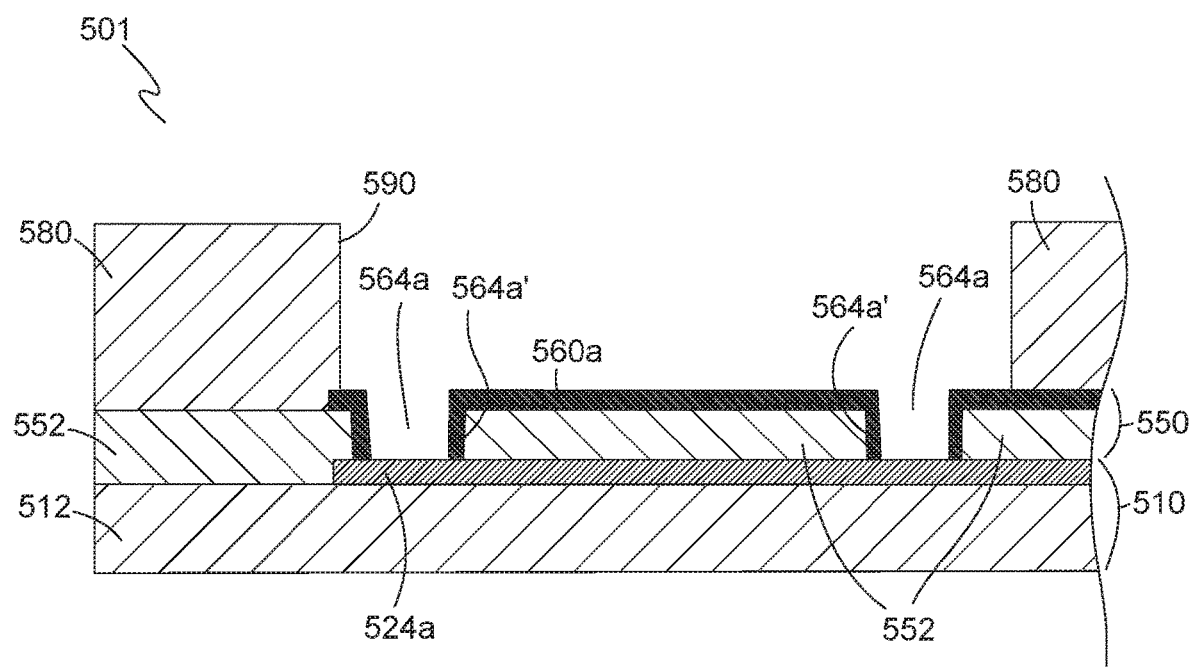
FIG. 50 is a cross-sectional enlarged view of one of the electrical contact pads showing the electrically conductive via from the middle layer to the base layer.

Referring now to FIG. 50, a cross-sectional slice of multi-layer sensor substrate 500 taken through substrate proximal end portion 501 at contact pad 524a is used to show the electrical continuity between base layer 510 and middle layer 550. Contact pad 524a is on base layer substrate 512, middle layer substrate 552 is disposed on base layer 510, contact pad 564a is disposed on middle layer substrate 552, and top layer 580 is disposed on middle layer 550. Contact pad 560a is disposed on middle layer substrate 552, including sidewalls 564a' of through openings 564a in middle layer substrate 552, thereby allowing electrical continuity between contact pad 560a and contact pad 524a. Top layer 580 is electrically insulating and is disposed on middle layer 550 to isolate middle layer 550 from the surrounding environment. In one embodiment, top layer 580 is polyimide that is spin coated onto middle layer 550 and has a thickness of about 55 μm after curing. An advantage of this multilayer construction method with connected vias is the overall width of multi-layer sensor assembly 500 is maintained as small as possible while allowing the creation of multiple electrodes with their accompanying electrically-conductive traces.

In one embodiment, base metallized layer 520 and middle metallized layer 570 each includes gold. In another embodiment, base metallized layer 520 and middle metallized layer 570 each includes a layer of chromium disposed directly on base layer substrate 512 and middle layer substrate 552, respectively, and a layer of gold disposed directly on top of the layer of chromium. In another embodiment, middle metallized layer 570 includes a layer of chromium disposed directly on the middle layer substrate 552, a layer of gold disposed directly on top of the layer of chromium, and a layer of platinum disposed directly on top of the layer of gold.

Figure 51:
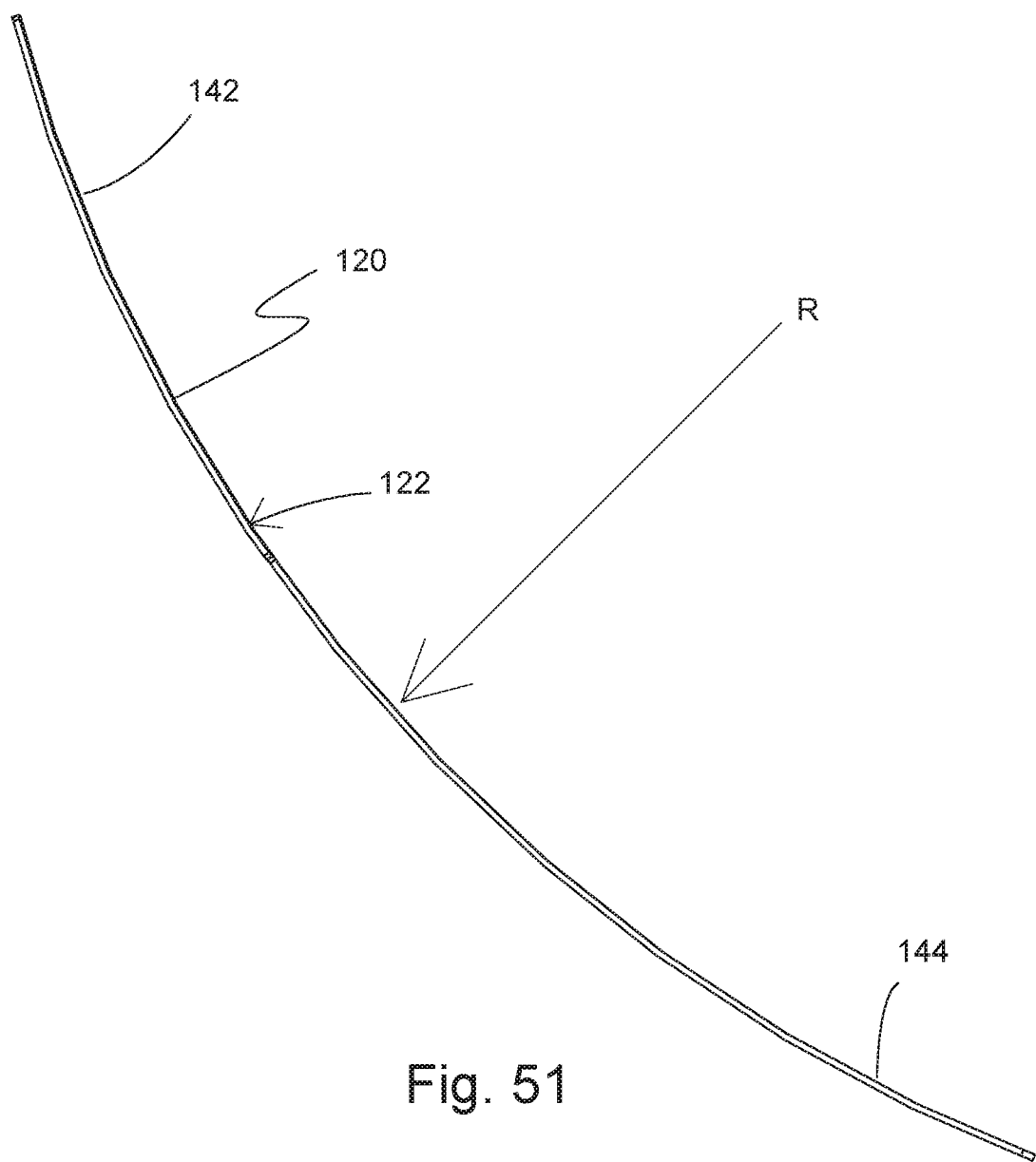
FIG. 51 is a schematic illustration of the CGM system of the present invention in use.

Referring now to FIG. 51, a side elevational view shows multi-layer sensor substrate 500 with proximal end portion 501 and distal end portion 502. The process used in making multi-layer sensor substrate 500 caused the completed sensor 120 to have an arcuate shape along is length. The arcuate shape forms a bend radius R to top surface 122. In one embodiment, bend radius R is no greater than 1.375 inch (35 mm). The bend radius R is a planned feature of the present invention. An advantage of the bend radius R is that the sensor distal end portion 502 of continuous monitoring sensor 120 is retained and firmly nested in the cannula/needle 100 during deployment into the patient due to frictional forces of multi-layer sensor substrate 500 engaging the cannula/needle inside wall without any other component or structure to ensure the sensor 120 remains intact and useable through the insertion process in the subcutaneous tissue. This is especially important considering the size of the distal end portion 502 of sensor 120 being 0.011 inches wide (279 microns) and 0.003 inches thick (75 microns).

Figure 52:
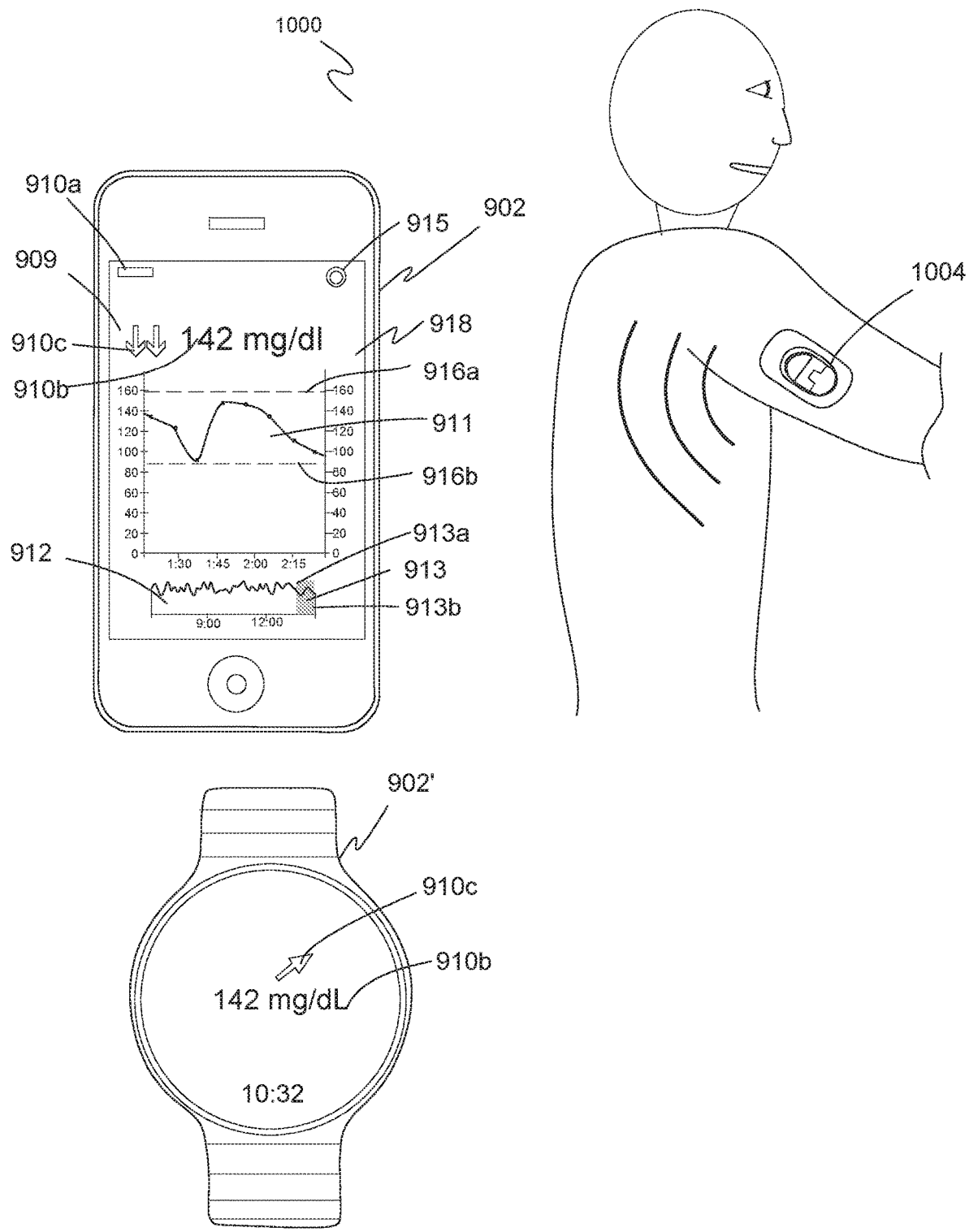
FIG. 52 is an enlarged, side view of one embodiment of the multi-layer sensor of the present invention showing the curl or bend of the sensor.

FIG. 52 shows one embodiment of system 1000 in use after insertion of sensor 120 into the subcutaneous tissue. As shown, FIG. 52 shows examples of electronic device 902, 902', a transmitter 1004 (which is sensor housing 206 containing sensor deployment assembly 236 and sensor housing cover 850) on the patient's arm, where transmitter 1004 communicates analyte measurement data from continuous monitoring sensor 120 deployed into the patient to electronic device 902, where the data is displayed to the user on a user interface 918.

System 1000 includes inserter assembly 200, a transmitter 1004, system software installed on an electronic device 902 equipped for wireless communication with transmitter 1004. Optionally, system 1000 utilizes an analyte strip reader 906 for calibration. Examples of electronic device 902 include a computer, a tablet computer, a phone, a data logger, a watch, an automobile information/entertainment system, or other electronic device. Wireless communication may be via radio frequency (RF) communication, Wi-Fi, BlueTooth, near-field communication (NFC), a sensor radio, mobile body area networks (MBAN) or other wireless communication protocol. In this embodiment, strip reader 906 has integrated BLE (BlueTooth low energy) and will send calibration data wirelessly to electronic device 902 and query the patient regarding the patient's intention to use the new calibration data point.

As discussed previously, the inserter assembly 200 is used to deploy continuous monitoring sensor 120 into the subject after positioning the inserter assembly 200 on the subject's body, deploying continuous monitoring sensor 120, and attaching the sensor housing cover 850 containing electronic module 700 and battery 706 (which includes transmitter 804) onto sensor housing 206 thereby forming transmitter 1004.

In one embodiment, transmitter 1004 communicates to the electronic device 902 using a wireless personal area network (WPAN), such as Bluetooth Low Energy (BLE). In other embodiments, other wireless communication protocols may be used with communication generally effective within a range of a few centimeters to a few meters. In some embodiments, for example, the system software is configured to communicate with Android and/or Apple software platforms installed on mobile phones and the like and has a range of up to thirty feet (about 9.2 meters).

In one embodiment, transmitter 1004 is designed to conserve power and operates via standard Bluetooth BLE protocol. For example, sensor readings from continuous monitoring sensor 120 are transmitted from transmitter 1004 every five minutes and the sensor reading is promptly displayed to the user after being received by the user's electronic device 902. Typically, transmitter 1004 will successfully connect with the electronic device 902 after one or two attempts.

In one embodiment, system 1000 uses universally unique identifier (UUID) filtering to prevent unwanted communication from another device. It is expected that multiple devices may be present and discoverable in proximity to electronic device 902, particularly when the user is in a densely populated area as in a subway, concerts, or other public locations.

In one embodiment, system 1000 utilizes calibration data obtained wirelessly from a separate strip reader. For example, a finger strip reading for glucose is taken and then either manually or automatically entered in system 1000 for calibration. In one embodiment, the system 1000 software application has a means for the user to manually enter a one-point calibration value taken from any meter. For example, the user uses the interface of the electronic device 902 to enter a calibration reading of 100 mg/dl obtained using a separate strip reader. After entering the calibration data, the user can accept, reject, or manually re-enter the calibration data. In other embodiments, the system software receives BLE calibration information from the external meter. After system 1000 receives the calibration data, the user can accept, reject, or manually re-enter this calibration data into the user interface.

The system software provides a user interface 918, one example of which is a touch-sensitive display screen. In one embodiment, user interface 918 has a main screen 909 with indicators 910a for radio strength and battery strength. Another indicator 910b displays the analyte concentration (e.g., glucose concentration) in units of mg/dL (milligrams per deciliter) or mmol/L (millimoles per liter). Indicator 1010c displays a glucose trending arrow to communicate to the user whether the analyte concentration (e.g., glucose) is increasing, decreasing, or unchanged. In one embodiment, indicator 910c for the trending arrow also communicates the relative rate of change.

In one embodiment, for example, a rate of change having an absolute value equal to or greater than a predefined value (e.g., ≥3 mg/dL) is displayed as two vertically-oriented arrows (up or down); a rate of change in a second predefined range with an absolute value less than the predefined value (e.g., 2-3 mg/dL is displayed as a single vertically-oriented arrow (up or down); a rate of change in a third predefined range with absolute value less than the second predefined range (e.g., 1-2 mg/dL is displayed as an arrow inclined at 45° to the horizontal (up or down); and a rate of change in a fourth predefined range with an absolute value less than the absolute value of the third predefined range (e.g., 1 mg/dL or less) is displayed as a horizontal arrow to indicate a steady state. In one embodiment, the rate of change is calculated based on five consecutive data points using the following formula:

$$b = \frac{\sum (x - \bar{x})(y - \bar{y})}{\sum (x - \bar{x})^2}$$

In one embodiment, analyte (e.g., glucose) concentration is updated every five minutes with data from transmitter 1004 and displayed on main screen 909. Optionally, transmitted data is updated and stored in transmitter 1004 in case electronic device 902 is out of range or unable to receive during that period. In one embodiment, each transmission by transmitter 1004 includes a predefined number of previous data points (e.g., five) to fill in missing data in the event electronic device 902 is unable to receive during that period.

Main screen 909 also displays a plot 911 of analyte concentration versus time. In one embodiment, the Y-axis (analyte concentration) is configured to automatically scale with a minimum Y-axis value 10% below the minimum value of plotted data and the maximum Y-axis value 10% above the maximum value of plotted data. The X axis may be configured to display a timeframe of the user's choosing.

Main screen 909 also displays a macro timescale 912 of data that includes data displayed in plot 911. Part of the data displayed in macro timescale 912 is highlighted and corresponds to the data displayed in plot 911. For example, macro timescale 912 may be configured to display analyte concentration data over three hours, six hours, twelve hours, twenty-four hours, three days, or one week. Accordingly, data displayed in plot 911 is a subset of data displayed in macro timescale 912. In one embodiment, highlighted area 913 of macro timescale 912 is an active element on user interface 908. For example, by touching highlighted area 913 in the center and dragging left or right, the data of plot 911 is selected and moved. Similarly, by touching highlighted area 913 on left edge 913a or right edge 913b and dragging left or right, highlighted area 913 is expanded or contracted along the time axis. When the size or location of highlighted area 913 is adjusted, plot 911 is automatically updated to display data between the same minimum time and maximum time of highlighted area 913. Main screen 909 also displays an active service icon 915. Selecting active service icon 915 displays a service screen with indicators 910 for calibration and customization. For example, the service screen includes indicators 910 for setting upper and lower ranges, alarm limits, displayed units, device pairing settings, time scale, X-axis time domain, and the like. For example, the user accesses the service screen to set the time range of data displayed in macro timescale 912 and plot 911. Selecting the calibration icon opens a calibration screen used to calibrate analyte data. In some embodiments, the service screen includes instructions for use or a link to access instructions for use.

For example, user-set or default values for maximum and minimum concentration/control limits are displayed on plot 911 as dashed lines 916a, 916b, respectively, extending horizontally. In one embodiment, user-set control limits are not alarmed. Default control limits provide upper and lower alert limits and upper and lower reportable range limits. A reading above the maximum 916a or below the minimum 916b results in an alarm, such as vibration or an audible alert to the user. In one embodiment, maximum concentration limit 916a has a default value of 510 mg/dL and minimum concentration limit 916b has a default value of 90 mg/dL.

In some embodiments, system software is configured to generate reports for health care professionals. For example, touching an icon opens reports and configurations that could be transferred to a Health Care Professional via the cloud, such as the amount of time above and below target ranges; alarm reports, CGM values; estimated A1C and eAG values, and analyte measurements over time.

In one embodiment, system 1000 enables the user to manually enter a one-point calibration value taken from a separate glucose strip reader. For example, the user enters 100 mg/dl as obtained from a test strip measurement. After entering calibration data, the patient shall accept, reject, or manually re-enter this calibration data into the user interface.

In another embodiment, system 1000 is configured to receive calibration information from strip reader via BLE or other wireless communication protocol.

In some embodiments, settings and preferences may be locked and are accessed only by entering a password, biometric information, or other information serving as a key to unlock the settings and preferences menu.

In one embodiment, system 1000 performs general data calculations using the following generic variable labels:

$$A0=(M*X+B)-(N*Y+C)$$

$$A1=A0+\text{calibration adjustment}$$

$$A2=A1/18.018018$$

$$X=((<\text{channel 0}>*0.000494)-1)*1000$$

$$Y=((<\text{channel 1}>*0.000494)-1)*1000$$

Generic variables are defined as follows:
A0 is uncalibrated CGM value in mg/dL
A1 is calibrated displayed CGM value in mg/dL
A2 is calibrated displayed CGM value in mmol/L (alternate units)
X is the mV reading output of Channel 0 (the sensor signal channel)
M is the slope correction factor Channel 0
B is offset correction factor for Channel 0
Y is the my reading output of Channel 1 (the blank signal channel)
N is the slope correction factor for channel 1
C is the offset correction factor for channel 1

In one embodiment, values for M, B, N, and C variables are stored on electronic device 902. In one embodiment, values A0, A1, X, and Y are stored to a Sqlite Database along with date timestamp. For example, datetime, channel-0-value, channel-1-value, calculated-glucose value, calculated-glucose-value-with-calibration, and device-id. Optionally, a separate database includes patient-entered calibration data with timestamp, such as datetime, entered-calibration value, and device-id.

In one embodiment, values for A1 or A2 (values displayed to the patient in plot 911) that are greater than a predefined maximum limit (e.g., 800 mg/dL or 27.7 mmol/L) result in an error message displayed on user interface 918, such as "Above Reportable Range." Similarly, values for A1 or A2 of less than a predefined minimum limit (e.g., 40 gm/dL or 2.2 mmol/L) result in an error message displayed to the user, such as "Below Reportable Range."

Communication between transmitter 1004 and electronic device 902 is secure. For example, BLE-supported Security Manager Protocol is utilized between transmitter 1004 and electronic device 902. SMP defines the procedures and behavior to manage pairing, authentication, and encryption between the devices, including encryption and authentication, pairing and bonding, key generation for device identity resolution, data signing, encryption, pairing method based on the input/output capabilities of transmitter 1004 and electronic device 902.

In one embodiment, electronic device 902 is a watch configured to communicate wirelessly with transmitter 1004. In such an embodiment, system software includes three screens on the user interface 918 of the electronic device 902' configured as a watch. A first screen displays the most recent analyte concentration and units of measurement. For example, glucose concentration is displayed by indicator 910b in mg/dL or mmol/L and is updated every five minutes. A trending arrow indicator 910c shows the relative rate of change as discussed above.

A second screen displays the most recent glucose concentration and units of measurement. Second screen displays plot 911 with analyte concentration data for the previous one hour, where the Y-axis is glucose concentration and the X-axis is time. Upper and lower limits 916a, 916b are displayed in dashed lines. A third screen displays macro timescale 912 with twenty-four hours of acquired data.

Figure 53:
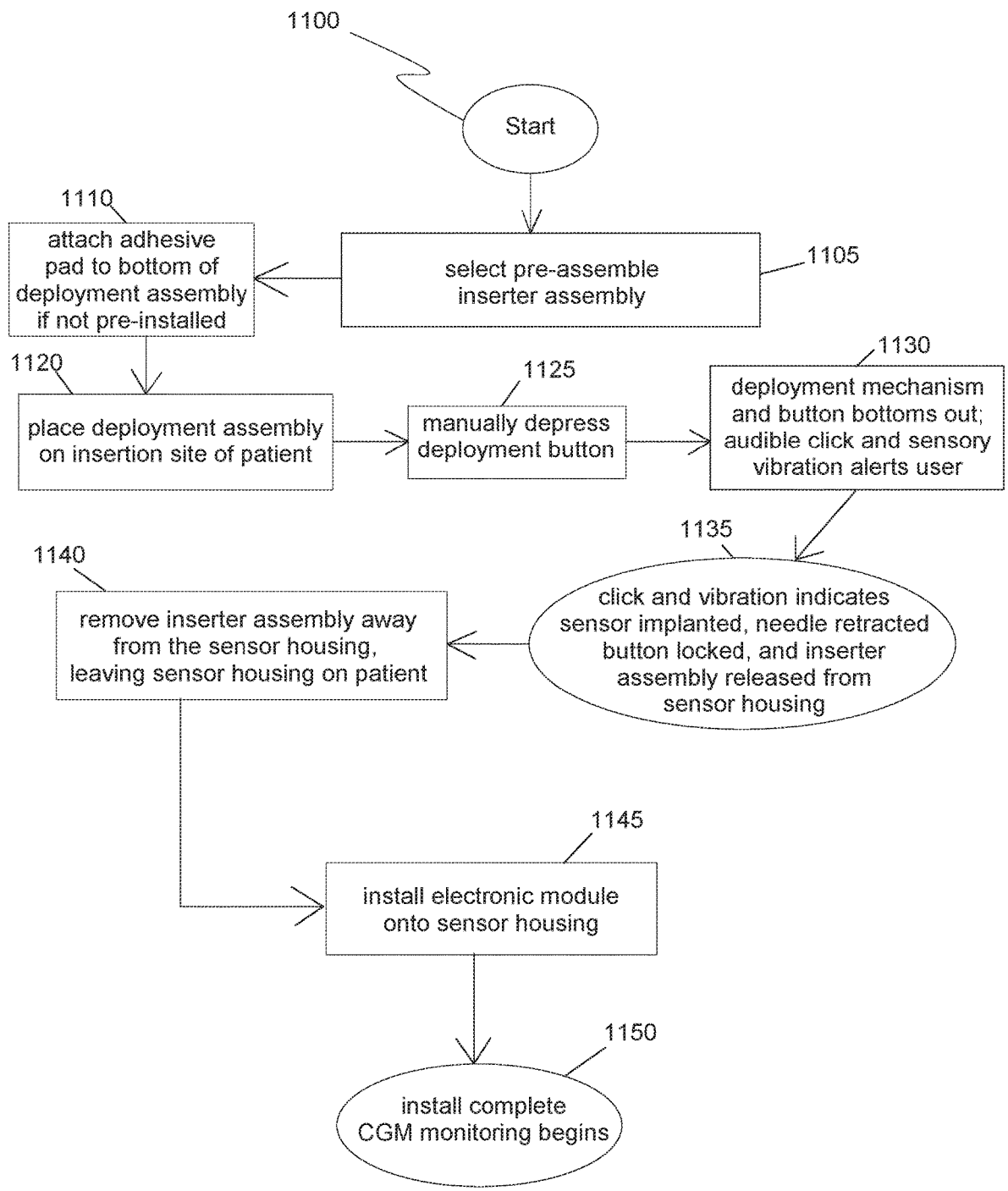
FIG. 53 is a flow chart showing the steps of the process that occurs when an inserter assembly of the present invention is used to implant an analyte sensor subcutaneously in a patient.

Subcutaneous Sensor Implantation Method:

Referring now to FIG. 53, a flow chart illustrates exemplary steps of a method 1100 for continuous analyte measurement such as, for example, glucose. To start, at step 1105 select an pre-assembled inserter assembly 200 that contains sensor deployment assembly 236 with a sensor 120. At step 1110, optionally place a sensor housing adhesive pad 600 configured for use with sensor housing 206 onto the bottom of the sensor housing if adhesive pad is not pre-installed. It is contemplated that adhesive pad 600 may already be attached to the inserter assembly 200 where the user simply removes a backing for attaching the inserter assembly 200 to a user's skin. It is further contemplated that other modes of adhesively securing the sensor housing 206 to the patient may be used, all as is well known in the art.

At step 1120, inserter assembly 200 is placed on the insertion site of the patient with sensor housing 206 and, if optionally attached, sensor housing adhesive pad 600 contacting the patient's skin. In one embodiment, the area of contact is quite small, measuring about 1 inch (25.4 mm) wide by about 1.5 inches (38.1 mm) long. In one embodiment, step 1120 includes fixing inserter assembly 200 to the skin using medical grade adhesive tape or the like.

At step 1125, the user manually presses button 204 down to its second position (down position) to drive the low-force needle/sharp 100 and continuous monitoring sensor 120. Typically, the needle/sharp 100 is inserted about 8 mm into the subcutaneous tissue. Step 1125 has been shown to take about 0.1 lbs. of force and be virtually painless to the patient.

At step 1130, deployment mechanism 208 "bottoms out" or reaches its furthest downward position towards sensor housing 206. An audible "click" along with a sensory vibration alerts the user. At step 1135, the audible click and the sensory vibration indicates to the user that the sensor 120 has been implanted, needle/sharp 100 has retracted back into inserter assembly 200, and inserter assembly 200 has released from sensor housing 206.

During step 1135, deployment mechanism 208 automatically retracts or moves from the pre-insertion needle carrier position (down position) to a released carrier needle position (up position), leaving continuous monitoring sensor 120 inserted about 7 mm into the skin. Needle/sharp 100 is released by the double acting deployment mechanism 208 that quickly retracts needle/sharp 100 and needle carrier 234.

At step 1140, inserter housing 202, deployment button 204, and deployment mechanism 208 (also collectively referred to as the inserter assembly 200) are removed/displaced from sensor housing 206 without requiring any further action to be performed to cause the inserter assembly 200 to release from the sensor housing 206. As previously described, release of inserter assembly 200 from the sensor housing 206 occurs automatically as deployment button 204 "bottoms out" and causes the release of locking mechanism 205 (e.g., pressing a snap feature) on inserter housing 202 away from sensor housing 206. The sensor housing 206 containing the sensor deployment assembly is left on the patient.

At step 1145, the sensor housing cover 850 containing the electronic module 700 and battery 706 is installed onto the sensor housing 206. Attaching sensor housing cover 850 onto sensor housing 206 automatically turns on power to electronic module 700 and the install is complete at step 1150.

At step 1145, the completed sensor housing assembly is now operational. The electronic module 700 begins receiving electrical signals generated by sensor 120. The electrical signals generated by sensor 120 that is implanted subcutaneously in a patient are directly related to the analyte concentration in the subcutaneous tissue. In the case of where a glucose sensor is used, the electrical signals generated by sensor 120 are directly related to the glucose concentration in the subcutaneous tissue. Electronic module 700 contains the electronic and/or electrical components that allows for measuring and recording the analyte of interest, which in the case of continuous glucose monitoring, is glucose. The data obtained from sensor 120 may be stored in electronic circuitry of the electronic and/or electrical components in electronic module 700 for simultaneous or later displays and/or transmission of the generated data. The electronic module may also include an inductive charging capability so that the onboard battery source can be conveniently charged without removal from the sensor housing.

Figure 54:
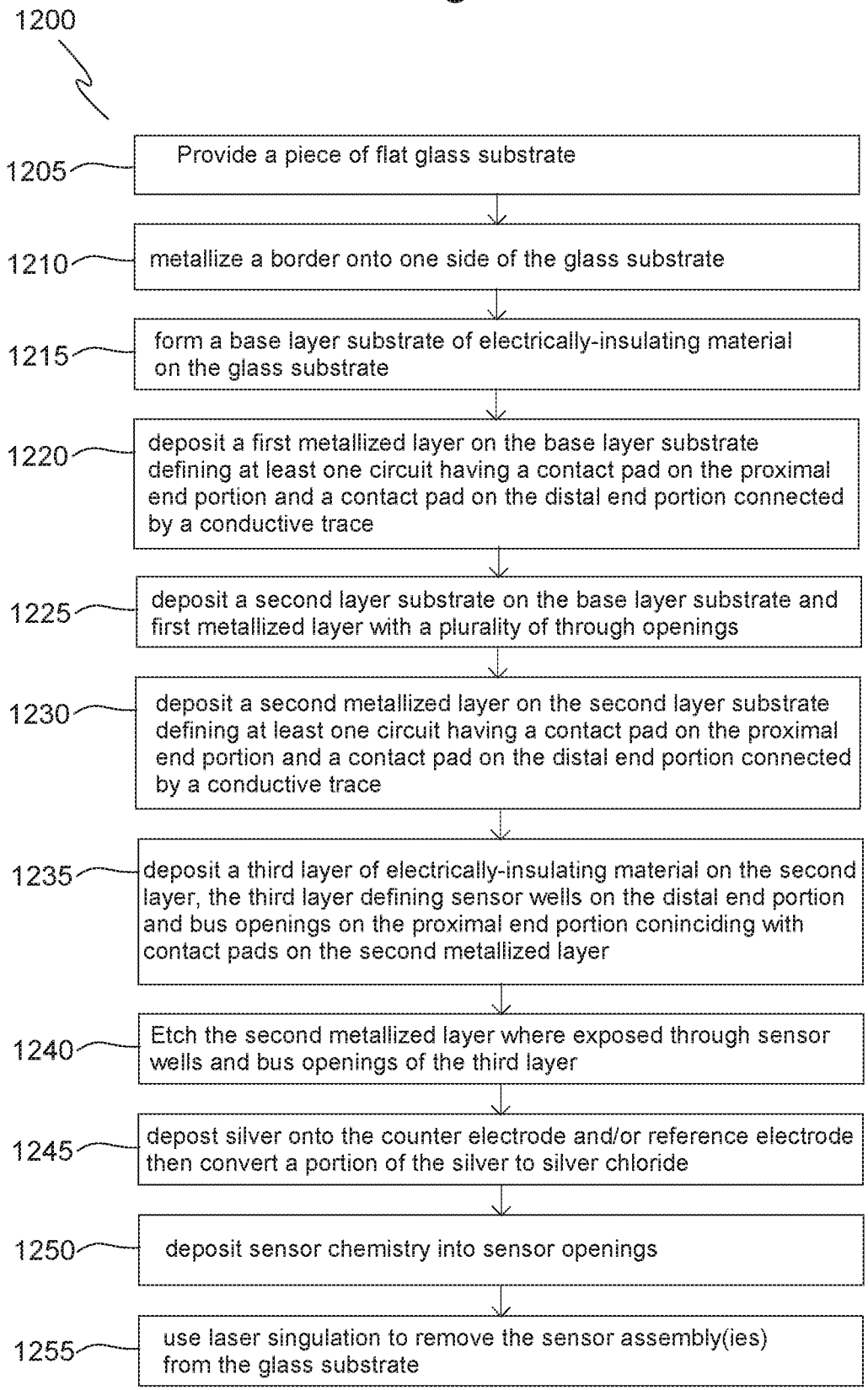
FIG. 54 is a flow chart showing the steps of the process of making the sensor of the present invention.

Sensor Substrate Formation Method:

Referring now to FIG. 54, a flowchart illustrates steps in one method 1200 of making multi-layer sensor substrate 500.

In step 1205, a piece of precision, flat soda-lime float glass substrate is provided with a size of 4"×4" and having a tin coating on the back surface.

In step 1210, a border is metalized onto the glass front side of the glass substrate. In one embodiment, the border has a width of 4 mm. Metalizing the border is performed by first imaging the border into a photoresist layer spin-coated onto the glass substrate. Next, a layer of chromium is deposited on the photoresist using a sputtering machine or thermal deposition. The photoresist is lifted off using acetone, then the surface is washed, baked dry, and plasma cleaned.

In step 1215, a first polyimide insulation layer (base layer substrate 512) is applied and cured. In one embodiment, the first polyimide layer is applied by spin coating and has a thickness of 10.0 μm±2.5 μm after curing. For example, the polyimide is applied by spin coating, followed by soft baking for ten minutes on a hot plate at 100° C. and curing in an oven or furnace by ramping the temperature to 350° C. and holding at temperature for thirty minutes. After curing, the first polyimide insulation layer thickness may be measured and verified.

In step 1220, base metallized layer 520 is applied to base layer substrate 512 and processed. First, an RF etch at 580 W is performed to clean the surface. In one embodiment, the base metallized layer 520 is deposited by sputtering and is a three-part metal layer that includes a first layer of chromium (thickness of 200±150 Å), a second layer of gold (1000±150 Å) sputtered onto the chromium, and a third layer of chromium (200±150 Å) sputtered onto the gold.

The base metallized layer 1220 is then imaged. First, photoresist is spin-coated onto base metallized layer 520 and soft baked on a hotplate as discussed above. Using a mask aligner, the features are aligned and the photoresist is exposed using a first metal layer mask. The photoresist is developed and plasma cleaned. Next, exposed metal of base metallized layer 520 is removed using ion milling, followed by removal of the remaining photoresist with a solvent. Optionally, the resistance of the base layer substrate 512 is checked to ensure all metal was removed. Optionally, conductive traces 528 of the base metallized layer 520 are inspected for shorts and opens and corrected where possible. To confirm operation of the circuit, measurements are taken for the resistance between the "working" and "blank" traces 528 at various locations. In one embodiment, the resistance is at least 10 MΩ, which is the resistance of an open load.

In step 1225, middle layer substrate 552 (e.g., a second polyimide insulative layer) is deposited onto the base layer 510 and processed. After depositing by spin coating, the middle layer substrate 552 is soft-baked, and cured. In one embodiment, the second polyimide insulation layer has a thickness of 10.0 μm±2.5 μm after curing. The second polyimide insulative layer is first soft baked for five minutes on a hot plate at 70° C., then soft baked for ten minutes on a hot plate at 105° C. Curing is performed in an oven or furnace by ramping to 350° C. and holding at temperature for thirty minutes, followed by plasma cleaning. The middle layer substrate 552 is imaged by applying photoresist, followed by alignment and exposing the photoresist using a "via mask" on the mask aligner. The photoresist is developed using a developer and rinsed in a spray develop unit.

In step 1230, a middle metallized layer 570 is deposited on the middle layer substrate 552 (second polyimide insulative layer) and processed. Middle metallized layer may be deposited using a sputtering machine or acceptable substitute. Optionally, this step initially includes an RF etch at 580 W performed prior to metal deposition for cleaning and preparing the surface. In one embodiment, the middle metallized layer 570 is a four-part layer that includes a first part of chromium (200±150 Å), a second part of gold (1000±150 Å) deposited onto the chromium, a third part of platinum (1000±150 Å) deposited onto the gold, and a fourth part of chromium (200±150 Å) deposited onto the platinum.

The middle metallized layer 570 is imaged. First, photoresist is spin-coated onto the middle metallized layer 570 followed by soft baking on a hotplate. Next, the photoresist is aligned and exposed using a second metal layer mask, followed by development of the photoresist and plasma cleaning. Next, the exposed metal of the middle metallized layer 570 is removed by ion milling. The remaining photoresist is then removed. Optionally, a resistance check is performed on the second polyimide insulative layer (middle layer substrate 552) to ensure the excess metal of the middle metallized layer 570 has been adequately removed. Conductive traces 574 of middle layer 550 are inspected for shorts and opens, followed by plasma cleaning.

Optionally, the resistance is checked for the middle metallized layer 570. For example, the resistance is measured between conductive traces 574. Preferably, the resistance is at least 10 MΩ (Open Load).

In step 1235, top layer 580 (e.g., third polyimide insulative layer) is applied to middle layer 550. In one embodiment, top layer 580 is a biocompatible polyimide or an acceptable substitute, where the polyimide is spin coated, soft baked, and cured. Soft baking is performed for five minutes on a hotplate at 70° C., followed by soft baking for ten minutes on a hotplate at 105° C. In one embodiment, top layer 580 has a thickness of 55.0 µm±5.0 µm after curing.

Top layer 580 is imaged to define contact openings 590 and sensor wells 592 that extend through top layer 580 and correspond to contact pads 560, 562, respectively, of middle metallized layer 570. In one embodiment, top layer 580 is polyimide with a thickness of about 55 µm after curing. After spin coating a layer of photoresist, the top layer 580 is aligned and the photoresist is exposed using a "well mask" on the mask aligner. The photoresist is developed using a developer and rinsed in a spray develop unit. Optionally, contact openings 590 and sensor wells 592 are inspected for complete development and then spot checked for a pre-cure height. The top layer 580 is then slow-cured in an oven or furnace by ramping to 550° C., holding at temperature for sixty minutes, then ramping to 350° C. and holding at temperature for thirty minutes. After slowly cooling, the top layer 580 is plasma cleaned and visually inspected using a microscope. Optionally, the depth of contact openings 590 and sensor wells 592 may be checked at various locations.

In step 1240, the middle metallized layer is etched where it is exposed through sensor wells 592 and contact openings 590 of the top layer 580. For example, the fourth chrome layer of the middle metallized layer 570 is chemically removed to expose the third platinum layer on all sensor wells 592 and contact openings 590. The sensor wells 592 and contact openings 590 are inspected for complete chromium removal, followed by plasma cleaning of the sensor assembly 120.

In step 1245, silver is deposited onto the reference electrode 134 defined by the sensor substrate, and subsequently a portion of the silver is converted to silver chloride to create a Ag/AgCl electrode, which will serve as a reference electrode.

In step 1250, the sensor chemistry is deposited into the sensor openings 592 as is discussed, for example, in method 1300 below.

In step 1255, laser singulation is performed to remove the continuous monitoring sensors 120 from the glass substrate and from each other. At this point, the bend or curl of continuous monitoring sensors 120 may be inspected and confirmed for conformance to the desired sensor bend or curl. For example, the sensor bend or curl is measured for a predefined number of sensors 120 per plate using a high-powered microscope. In one embodiment, the maximum bend radius R is no more than 1.375 inches (~35 mm). With this bend radius R, the continuous monitoring sensor 120 is maintained inside the cannula/needle 100 due to frictional forces with the inside wall of the cannula/needle 100.

Exceeding the maximum bend radius may result in the continuous monitoring sensor 120 falling out of the cannula. Bend radius R results in part from the relative thicknesses of layers 500, 510, 550. Bend radius R also results in part from sequentially curing layers 500, 510, 550 of multi-layer sensor substrate 500 starting with base layer 510, followed by middle layer 550, and followed by top layer 580. The polyimide of base layer substrate 512 shrinks about 37% in thickness when cured. The polyimide of middle layer substrate 552 and top layer 580 shrinks about 40% in thickness when cured. Also, since top layer 580 (~55 µm) is approximately ten times as thick as either of base layer 510 (~10 µm) or middle layer 550 (~10 µm)), shrinkage of top layer 550 during curing after base layer 510 and middle layer 550 imparts bend radius R to multi-layer sensor substrate 500.

In one embodiment, continuous monitoring sensor 120 has a length of about 18.42 mm with substrate proximal end portion 501 having a length of about 6.99 mm, substrate distal end portion 502 and assembly middle portion 503 each have a width of about 279 µm, and substrate proximal end portion 501 has a width of about 711 µm. With these dimensions, continuous monitoring sensor 120 is sized for use within a circular 25 gauge thin wall stainless steel tubing or 27 gauge flattened thin wall stainless steel tubing, both of which are shaped into a sharp forming needle 100. The 25 gauge thin wall tubing has an outside diameter of about 0.020 inch (0.51 mm) nominal, and an inside diameter of about 0.015 inch (0.38 mm). The 27 gauge thin wall tubing has an outside diameter of about 0.016 inch (0.41 mm) nominal, and an inside diameter of about 0.012 inch (0.30 mm) nominal. Other gauges of needles are acceptable and dimensions of multi-layer sensor substrate 500 may be adjusted as needed for a tighter or looser fit within a given needle.

An advantage of making continuous monitoring sensor 120 with a plurality of layers (e.g., 510, 550, 580) in multi-layer sensor substrate 500 is the ability to have more circuits (e.g., 522, 572) in a predefined area. As such, continuous monitoring sensor 120 has increased the available placement options for electrodes 130, 132, 133, 134. Also, a plurality of layers increases the ability to have a larger number of electrode circuits in the same predefined area thus permitting a variety of different types of electrodes on a single continuous monitoring sensor 120. It is contemplated within the scope of the present invention that continuous monitoring sensor 120 has additional layers, such as a fourth, fifth, sixth, or other additional layer (i.e. other "middle" layers between base layer 510 and middle layer 550/top layer 580.

Sensor Chemistry Deposition Method:

Referring now to FIG. 55, a flowchart illustrates exemplary steps of one method 1300 for depositing sensor chemistry as noted above in step 1250 of method 1200. In step 1310, a multi-layer sensor substrate 500 is provided as described above in steps 1205-1275 of method 1200, where multi-layer sensor substrate 500 defines two or more electrodes that are at least a first working electrode and a reference electrode and where other electrodes are selected from a counter electrode, a second working electrode, and other analyte working electrodes, all being on one side of sensor substrate 500. Typically, a plurality of multi-layer sensor substrates 500 are provided as a group on the glass substrate.

In step 1315, liquid photoresist is applied to the sensor substrate, such as by spin coating. The photoresist is exposed to UV light in a predefined pattern, and the unexposed areas are removed to define a pattern with openings in the photoresist aligned with sensor openings 590 and/or sensor wells 592 of the sensor substrate. Similarly, if negative photoresist is used, the exposed areas are removed. It should be understood that embodiments of the present invention are discussed as having electrodes 130, 132, 133, 134 on one side of the multi-layer sensor substrate 500; a two-sided sensor is also contemplated as being within the scope of the present invention.

In step 1320, a hydrogel membrane is deposited onto the Ag/AgCl reference electrode 134 and counter electrode 133 by dispensing a predefined amount of hydrogel membrane solution, followed by UV curing and washing.

In step 1325, a layer of photoresist is deposited onto the sensor substrate, exposed to UV light, and stripped to define openings corresponding to the working electrode 130 and blank electrodes 133 defined in the sensor substrate.

In step 1335, a poly-2-hydroxyethyl methacrylate (PHEMA) membrane precursor solution is deposited onto the working electrode 130 and blank electrode 133, UV cured, washed and dried. It should be understood by those skilled in the art that one of the two electrodes is a glucose electrode and, accordingly, the PHEMA membrane precursor solution for this electrode additionally contains a glucose enzyme, preferably glucose oxidase. Optionally, the PHEMA membrane precursor solution that contains the glucose enzyme may also contain a predefined quantity of microspheres in addition to the composite membrane described below. The predefined quantity of microspheres is less than the amount of microspheres in the composite membrane described below.

In step 1340, a composite membrane precursor solution is deposited onto the working electrode 130 (e.g., a glucose electrode) and the blank electrode 133, UV cured, and dried.

The preparation of the composite membrane precursor solution will now be described. Microspheres are prepared from a material having substantially no or little permeability to glucose but a substantially high permeability to oxygen. The microspheres are preferably prepared from PDMS (polydimethylsiloxane). The microspheres are mixed with a hydrogel precursor that allows the passage of glucose. While polyurethane hydrogels work, a PHEMA precursor is preferred. The ratio of microspheres to hydrogel determines the ratio of the glucose to oxygen permeability. Thus, one of ordinary skill in the art can easily determine the ratio that enables the desired dynamic range of glucose measurement at the required low oxygen consumptions. It should be noted that if a polyurethane hydrogel is used, the membrane is cured by evaporating the solvent instead of using ultraviolet light.

In step 1345, additional PHEMA membrane precursor catalase solution is optionally deposited onto the working electrode 130 (e.g., glucose) and blank electrode 133, UV cured, and dried. This optional step adds catalase that prevents release of hydrogen peroxide to the biological environment, reduces the flow rate influence on sensor sensitivity, and prevents direct contact of the microspheres surface to the biological environment.

In step 1350 and after the singulation step described in FIG. 48, the continuous monitoring sensor 120 is installed into a cannula/needle 100 according to the preferred embodiments previously described.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An electrochemical sensor assembly for use as a subcutaneous analyte sensor, the electrode assembly comprising:
   a base layer comprising:
      a base layer substrate of electrically-insulating material defining a base layer proximal end portion, a base layer distal end portion, and a base layer middle portion between the base layer proximal end portion and the base layer distal end portion; and
      a base metallized layer disposed on the base layer substrate and defining at least one circuit extending longitudinally along the base layer substrate wherein the at least one circuit has an electrically-conductive contact pad formed at each of the base layer proximal end portion and the base layer distal end portion with an electrically-conductive trace electrically coupling the electrically-conductive contact pad at the base layer proximal end portion with the electrically-conductive pad at the base layer distal end portion;
   a middle layer disposed over the base layer, the middle layer comprising:
      a middle layer substrate of electrically-insulating material and having a middle layer proximal end portion, a middle layer distal end portion, and a middle layer middle portion, wherein the middle layer is aligned with the base layer and has a plurality of middle layer through openings with side walls, and wherein each of the plurality of middle layer through openings is in communication with a respective one of the electrically-conductive contact pads of the at least one circuit of the base layer; and
      a middle metallized layer disposed on the middle layer substrate and the side walls of the middle layer through openings, the middle metallized layer defining at least two circuits, wherein each of the at least two middle layer circuits has an electrically-conductive contact pad formed at each of the middle layer proximal end portion and the middle layer distal end portion with an electrically-conductive trace electrically coupling the electrically-conductive contact pad at the middle layer proximal end portion with the electrically-conductive pad at the middle layer distal end portion, wherein one of the at least two middle layer circuits is electrically coupled to the at least one circuit of the base layer by way of the plurality of middle layer through openings;
   a top layer of electrically-insulating material disposed over the middle layer, the top layer having a plurality of contact openings that coincide with each electrically-conductive contact pad of the middle layer proximal end portion and a plurality of sensor wells that coincide with each of the electrically-conductive contact pads of the middle layer distal end portion, thereby creating a substrate assembly with a substrate proximal end portion, a substrate distal end portion and an assembly middle portion extending longitudinally between the substrate proximal end portion and the substrate distal end portion;

a sensing layer disposed on at least one electrically-conductive contact pad formed at the middle layer distal end portion forming at least a first working electrode; and a reference layer disposed on at least one electrically-conductive contact pad formed at the middle layer distal end portion forming a reference electrode.

2. The electrochemical sensor assembly of claim 1, wherein the base layer, the at least one circuit of the base layer, the middle layer, the at least two circuits of the middle layer, and the top layer together impart an arcuate shape to the substrate assembly from the substrate proximal end portion to the substrate distal end portion.

3. The electrochemical sensor assembly of claim 2, wherein the arcuate shape has a bend radius of 1.375 inches (34.9 mm) or less.

4. The electrochemical sensor assembly of claim 1, wherein the electrically insulating material of each of the base layer, the middle layer, and the top layer is polyimide that is spun formed and thermally cured.

5. The electrochemical sensor assembly of claim 1, wherein the base layer substrate and the middle layer substrate each have a thickness of about 10 microns.

6. The electrochemical sensor assembly of claim 1, wherein the top layer has a thickness of 55 microns.

7. The electrochemical sensor assembly of claim 1, wherein each of the substrate distal end portion and the assembly middle portion has a width of 279 microns.

8. The electrochemical sensor assembly of claim 1, wherein the base layer includes at least two circuits wherein, one of the at least two circuits has an electrically-conductive pad at the distal end portion of the base layer in combination with the sensing layer on the middle layer distal end portion forms a working electrode circuit and wherein a second one of the at least two circuits has a second electrically-conductive pad at the middle layer distal end portion forms a second working electrode.

9. The electrochemical sensor assembly of claim 1, wherein the sensing layer forming the at least first working electrode includes a base coating layer containing PHEMA and glucose oxidase, a second coating layer over the base coating layer, the second coating layer containing PHEMA and a plurality of microspheres made of a material having no permeability to glucose but a permeability to oxygen, and a third coating layer over the second coating layer, the third coating layer containing PHEMA and a material that prevents release of hydrogen peroxide from the sensing layer.

* * * * *